(12) United States Patent
Gardner

(10) Patent No.: US 10,335,023 B2
(45) Date of Patent: Jul. 2, 2019

(54) ENDOTRACHEAL TUBE INSERTION DEVICE

(71) Applicant: Glenn P. Gardner, Oak Brook, IL (US)

(72) Inventor: Glenn P. Gardner, Oak Brook, IL (US)

( * ) Notice: Subject to any disclaimer, the term of this patent is extended or adjusted under 35 U.S.C. 154(b) by 0 days.

(21) Appl. No.: 15/926,197

(22) Filed: Mar. 20, 2018

(65) Prior Publication Data
US 2018/0242833 A1 Aug. 30, 2018

Related U.S. Application Data

(63) Continuation of application No. 15/399,816, filed on Jan. 6, 2017, now Pat. No. 9,949,629.

(60) Provisional application No. 62/276,035, filed on Jan. 7, 2016.

(51) Int. Cl.

| | | |
|---|---|---|
| *A61B 1/267* | (2006.01) | |
| *A61M 16/04* | (2006.01) | |
| *A61B 1/00* | (2006.01) | |
| *A61B 1/01* | (2006.01) | |
| *A61B 1/05* | (2006.01) | |

(Continued)

(52) U.S. Cl.
CPC .......... *A61B 1/267* (2013.01); *A61B 1/00009* (2013.01); *A61B 1/00016* (2013.01); *A61B 1/0052* (2013.01); *A61B 1/0055* (2013.01); *A61B 1/00078* (2013.01); *A61B 1/00124* (2013.01); *A61B 1/00126* (2013.01); *A61B 1/00154* (2013.01); *A61B 1/01* (2013.01); *A61B 1/051* (2013.01); *A61B 1/0684* (2013.01); *A61M 16/0418* (2014.02); *A61M 16/0434* (2013.01); *A61M 16/0445* (2014.02); *A61M 16/0463* (2013.01); *A61M 16/0486* (2014.02); *A61M 16/0488* (2013.01); *A61M 16/0495* (2014.02)

(58) Field of Classification Search
CPC ................ A61M 3/02; A61M 16/0418; A61M 16/0429; A61M 16/0427
USPC ......................................................... 604/276
See application file for complete search history.

(56) References Cited

U.S. PATENT DOCUMENTS

| | | | | |
|---|---|---|---|---|
| 2,923,299 A | * | 2/1960 | Blackwood ....... | A61M 16/0465 128/207.17 |
| 3,606,669 A | * | 9/1971 | Kemble ............ | A61M 16/0465 128/200.26 |

(Continued)

OTHER PUBLICATIONS

Gain More Control Using the First Articulating Video Laryngoscope. (n.d.). Retrieved Jul. 25, 2018, from https://www.blinkdc.com/flexview.

(Continued)

*Primary Examiner* — David W Bates
(74) *Attorney, Agent, or Firm* — MacMillan, Sobanski & Todd, LLC

(57) ABSTRACT

An intubation assembly rod is configured to have an endotracheal tube carried thereon and includes an elongated body having a distal end and a proximal end. The distal end of the intubation assembly rod body is tapered, rounded, or spherical, and defines a leading end of the intubation assembly rod. The intubation assembly rod includes a longitudinally extending channel configured such that an elongated member of a device to which the intubation assembly rod may be attached may be inserted into the channel.

32 Claims, 42 Drawing Sheets

(51) Int. Cl.
*A61B 1/06* (2006.01)
*A61B 1/005* (2006.01)

(56) References Cited

U.S. PATENT DOCUMENTS

| | | | | |
|---|---|---|---|---|
| 4,068,658 | A | * | 1/1978 | Berman ............ A61M 16/0488 128/200.26 |
| 4,185,639 | A | * | 1/1980 | Linder ............... A61M 16/0488 128/200.26 |
| 4,211,234 | A | * | 7/1980 | Fisher ................ A61M 16/0488 128/200.26 |
| 4,246,897 | A | * | 1/1981 | Muto ................. A61M 16/0463 128/207.15 |
| 4,527,553 | A | * | 7/1985 | Upsher .................... A61B 1/07 600/188 |
| 4,798,193 | A | * | 1/1989 | Giesy ................ A61M 25/0105 600/114 |
| 4,913,139 | A | * | 4/1990 | Ballew ............... A61M 16/0488 128/200.11 |
| 5,163,941 | A | * | 11/1992 | Garth ................ A61M 16/0488 606/108 |
| 5,184,603 | A | * | 2/1993 | Stone ................. A61B 1/2676 600/193 |
| 5,323,771 | A | * | 6/1994 | Fisher ............... A61M 16/0488 128/200.26 |
| 5,443,058 | A | | 8/1995 | Ough |
| 5,489,256 | A | | 2/1996 | Adair |
| 5,551,946 | A | | 9/1996 | Bullard |
| 5,607,386 | A | | 3/1997 | Flam |
| 5,645,519 | A | | 7/1997 | Lee et al. |
| 5,665,052 | A | | 9/1997 | Bullard |
| 5,749,357 | A | * | 5/1998 | Linder ............... A61M 16/0429 128/200.26 |
| 6,146,402 | A | | 11/2000 | Munoz |
| 6,443,156 | B1 | | 9/2002 | Niklason et al. |
| 6,471,643 | B1 | * | 10/2002 | Henderson ............ A61B 1/267 600/185 |
| 6,585,642 | B2 | | 7/2003 | Christopher |
| 6,878,106 | B1 | | 4/2005 | Herrmann |
| 6,929,600 | B2 | | 8/2005 | Hill |
| 7,322,357 | B2 | * | 1/2008 | Nelson .................. A61M 16/04 128/207.14 |
| 7,552,729 | B2 | * | 6/2009 | O'Mara ............ A61M 16/0488 128/200.26 |
| 7,563,227 | B2 | | 7/2009 | Gardner |
| D603,958 | S | | 11/2009 | Schwartz et al. |
| 7,658,708 | B2 | | 2/2010 | Schwartz et al. |
| 7,706,861 | B2 | | 4/2010 | Windheuser et al. |
| 7,771,396 | B2 | | 8/2010 | Stefanchik et al. |
| 7,815,565 | B2 | | 10/2010 | Stefanchik et al. |
| 8,667,966 | B2 | | 3/2014 | Koike |
| 8,777,840 | B2 | | 7/2014 | Belafsky |
| 8,845,525 | B2 | | 9/2014 | McGrath et al. |
| 8,888,683 | B2 | | 11/2014 | Mejia |
| 9,283,342 | B1 | | 3/2016 | Gardner |
| 9,888,832 | B2 | | 2/2018 | Schwartz et al. |
| 2003/0183234 | A1 | * | 10/2003 | Ranzinger ............ A61M 16/04 128/207.15 |
| 2004/0210114 | A1 | | 10/2004 | Simon |
| 2005/0090712 | A1 | * | 4/2005 | Cubb .................. A61B 1/00073 600/120 |
| 2005/0126564 | A1 | * | 6/2005 | Pekar ................ A61M 16/0484 128/200.26 |
| 2006/0258903 | A1 | | 11/2006 | Stefanchik et al. |
| 2006/0258904 | A1 | | 11/2006 | Stefanchik et al. |
| 2007/0066869 | A1 | | 3/2007 | Hoffman |
| 2007/0106122 | A1 | * | 5/2007 | Yokota ............... A61B 1/00048 600/188 |
| 2007/0163596 | A1 | * | 7/2007 | Mikkaichi ............ A61M 16/04 128/207.14 |
| 2007/0225554 | A1 | | 9/2007 | Maseda et al. |
| 2008/0058599 | A1 | * | 3/2008 | Schwartz .......... A61M 16/0488 600/139 |
| 2008/0208000 | A1 | * | 8/2008 | Schwartz .......... A61M 16/0488 600/120 |
| 2009/0125002 | A1 | | 5/2009 | Totz |
| 2009/0322867 | A1 | * | 12/2009 | Carrey ............... A61B 1/00039 348/77 |
| 2013/0023729 | A1 | | 1/2013 | Vazales et al. |
| 2013/0030249 | A1 | | 1/2013 | Vazales et al. |
| 2013/0319406 | A1 | * | 12/2013 | Borrye .................. A61B 1/267 128/200.26 |
| 2014/0150782 | A1 | * | 6/2014 | Vazales ............. A61M 16/0463 128/202.16 |
| 2018/0353260 | A1 | * | 12/2018 | Vazales .................. A61B 90/70 |

OTHER PUBLICATIONS

Ketaminh, "King Vision Bougie Supreme—refining a novel hybrid intubation technique", Pharm: Prehospital and Retrieval Medicine, 2012.

International Search Report and Written Opinion, Application No. PCT/US2017/012440, dated May 4, 2017.

* cited by examiner

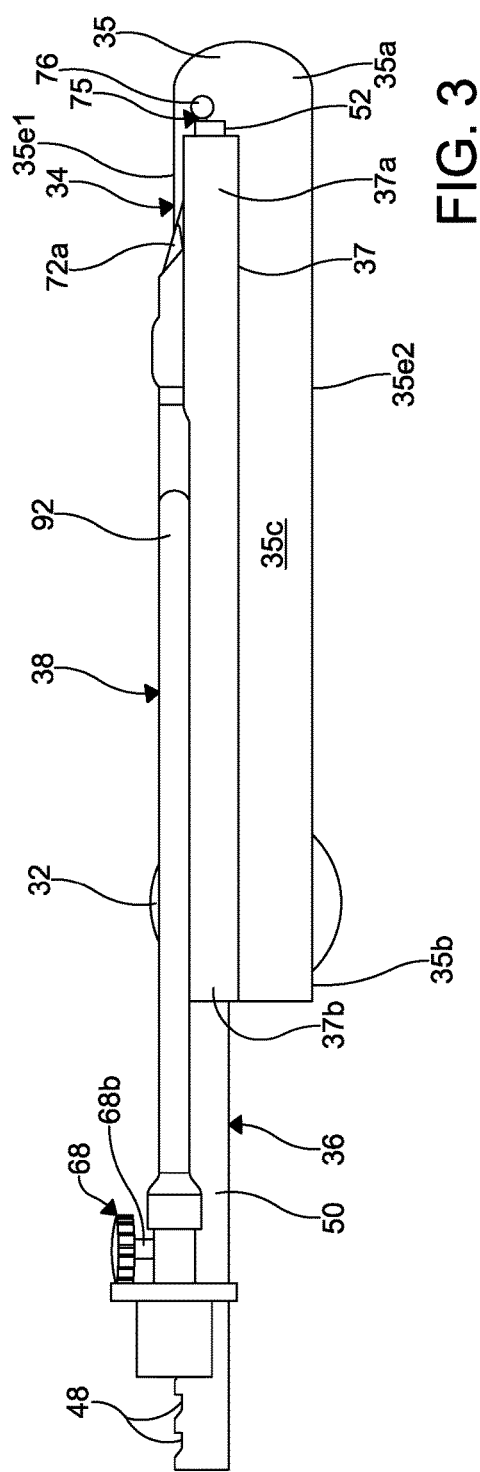
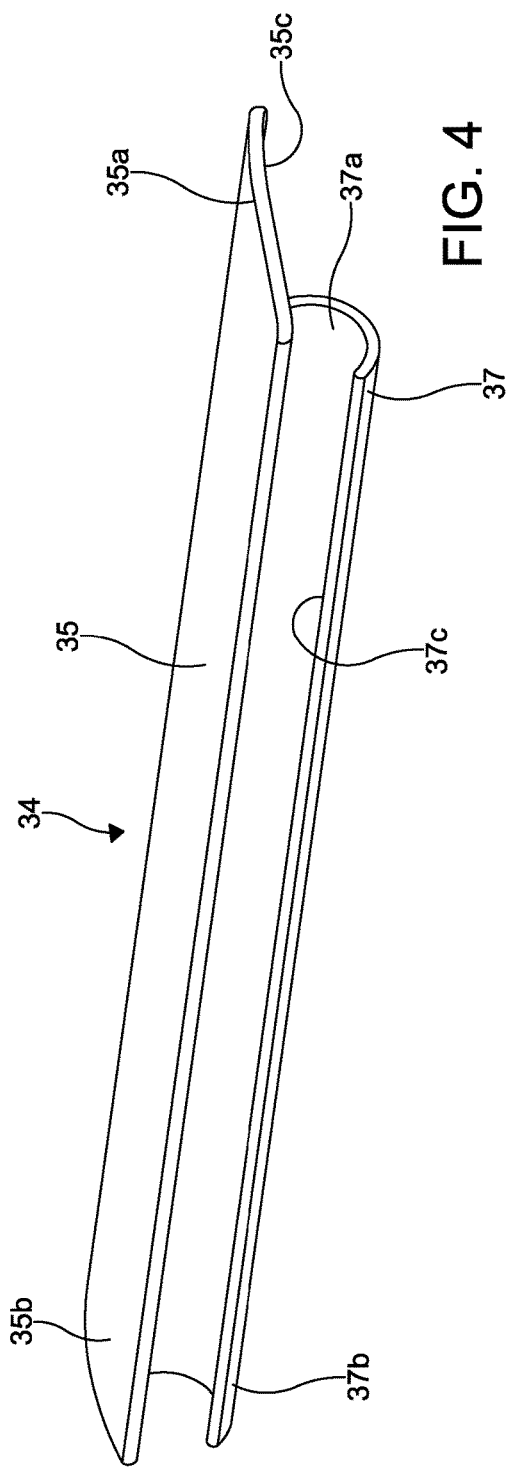

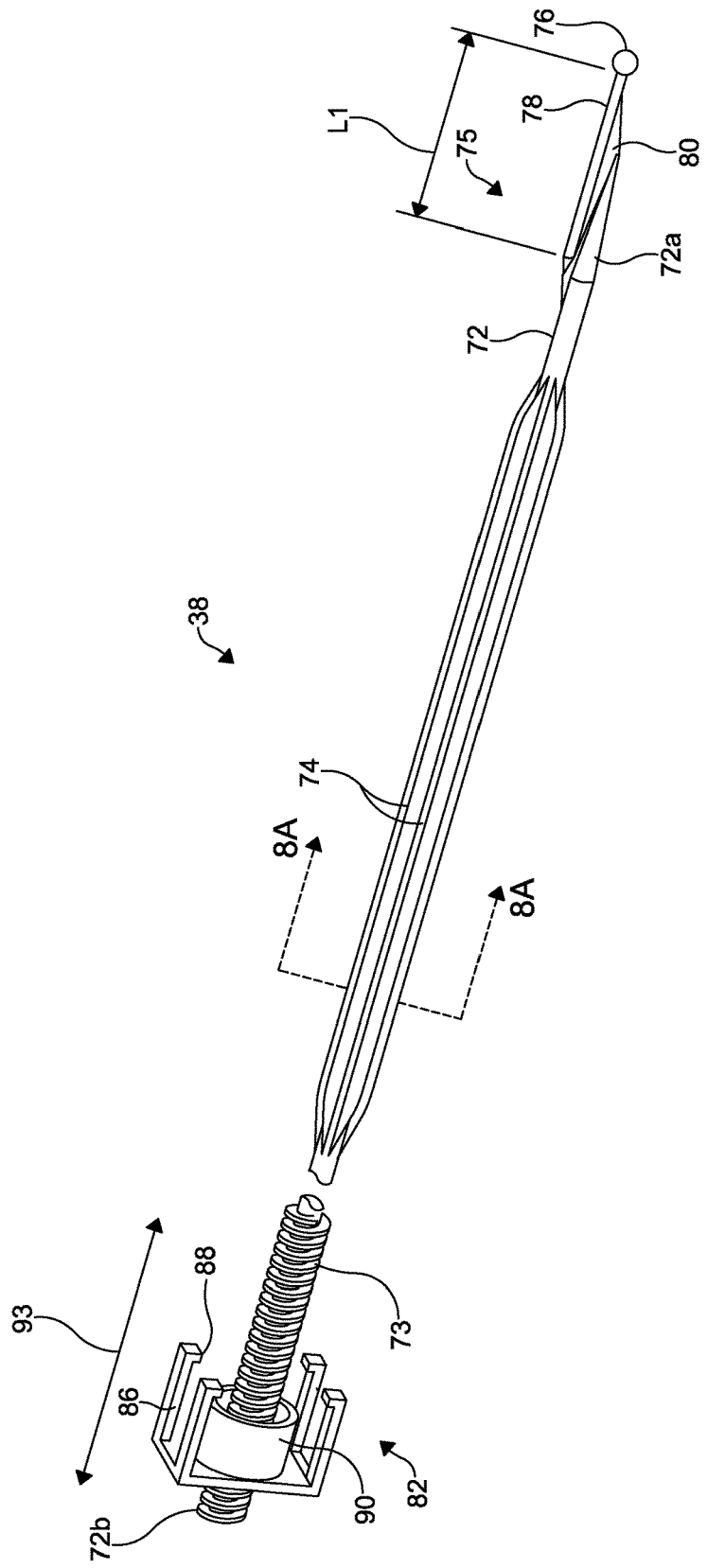

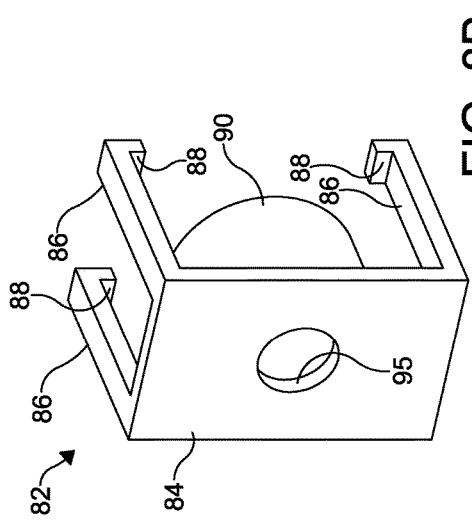
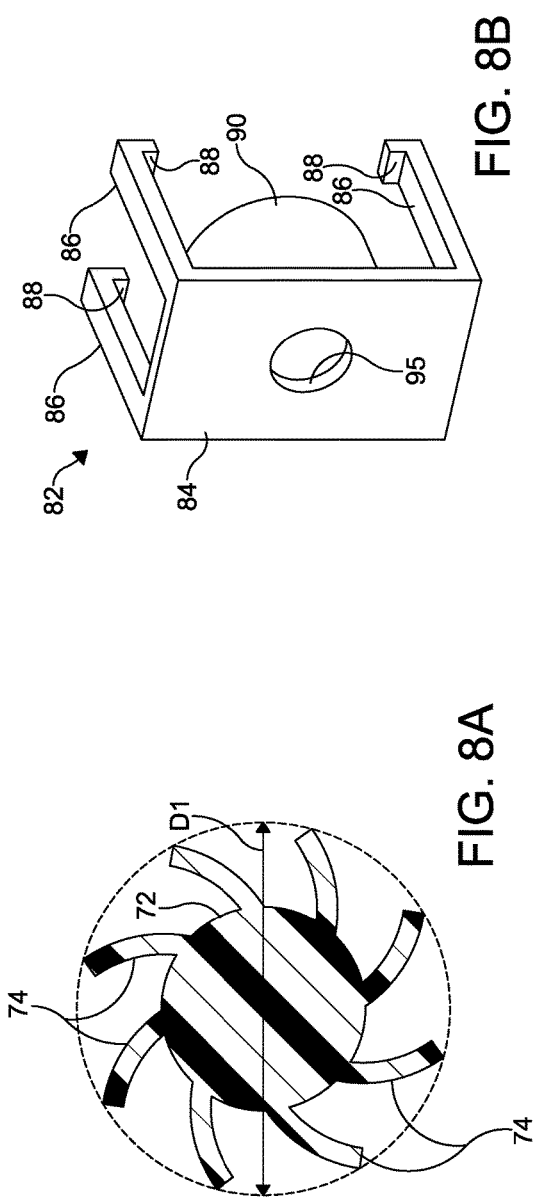
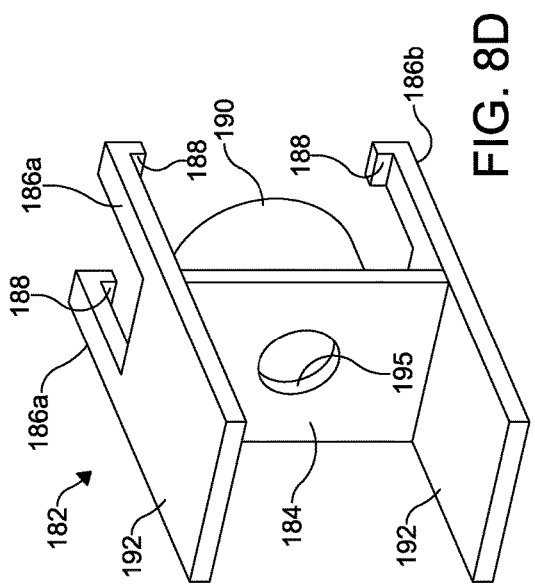
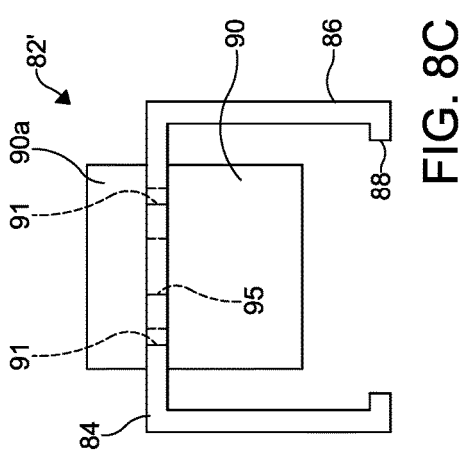

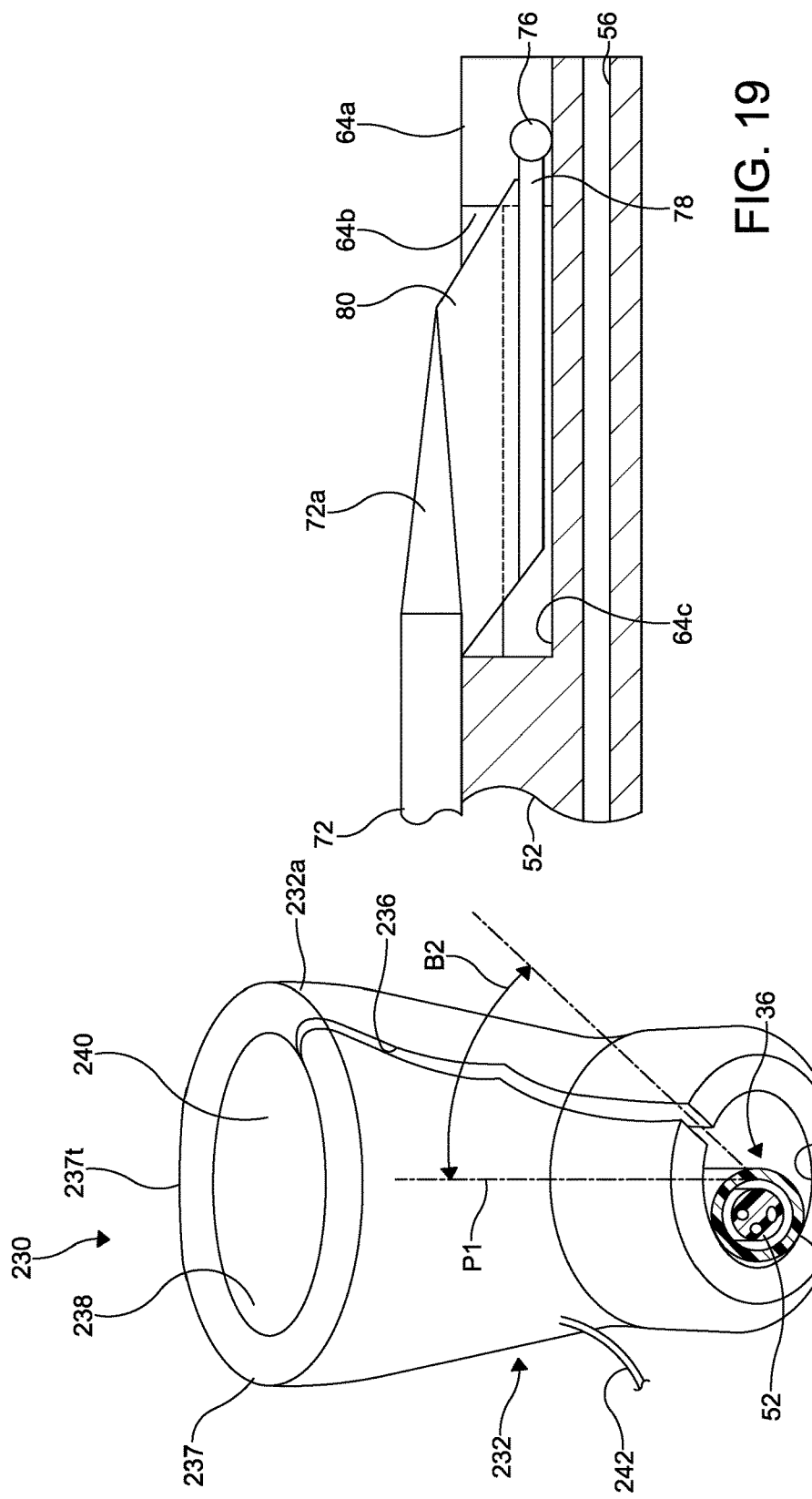

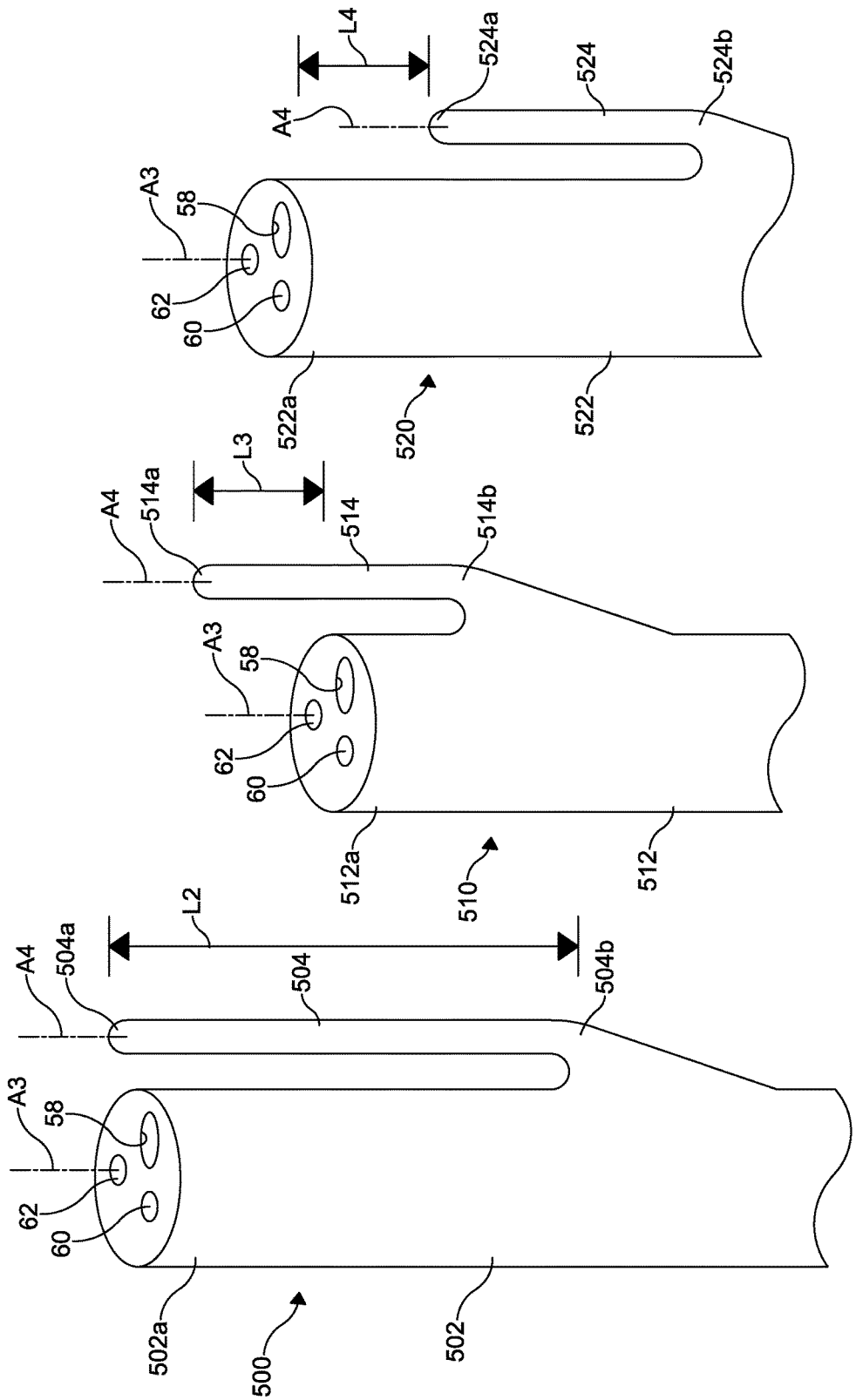

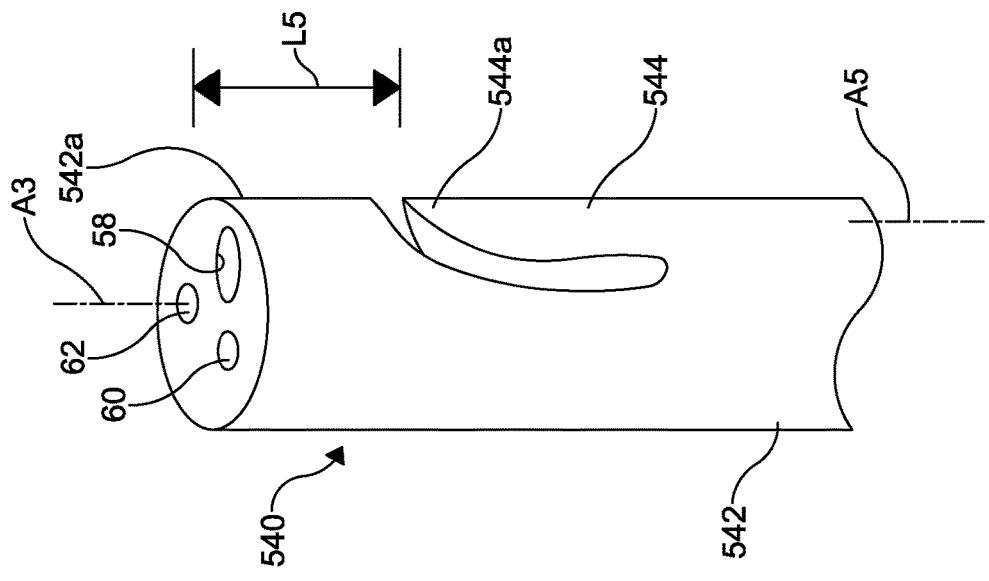
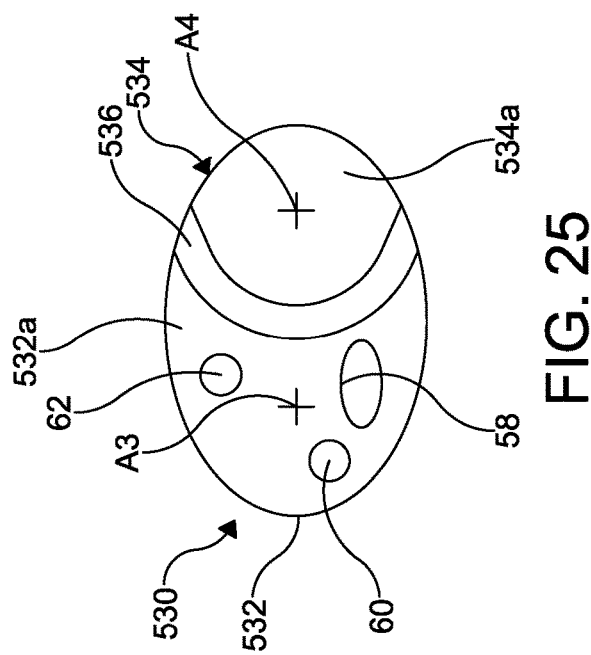

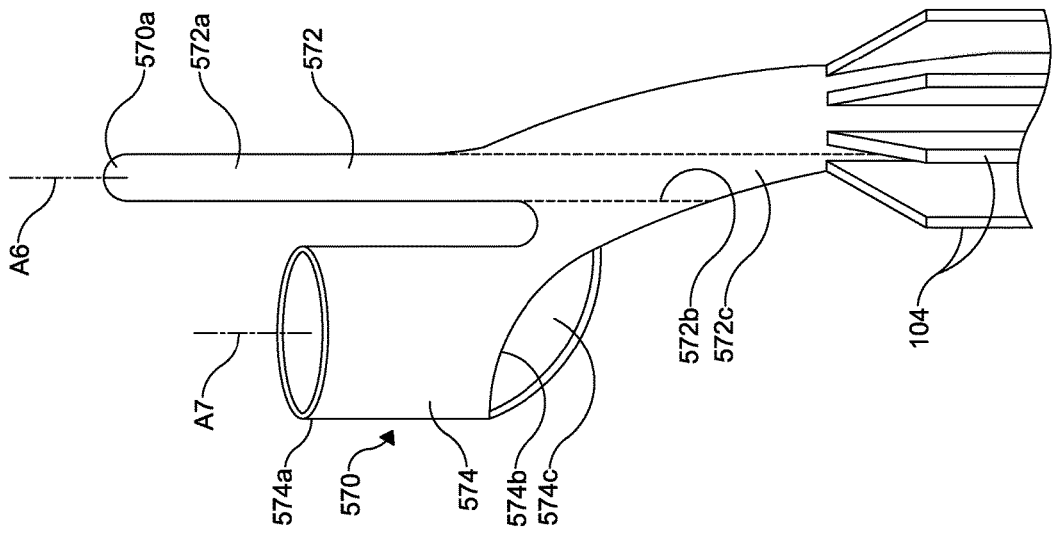
FIG. 29
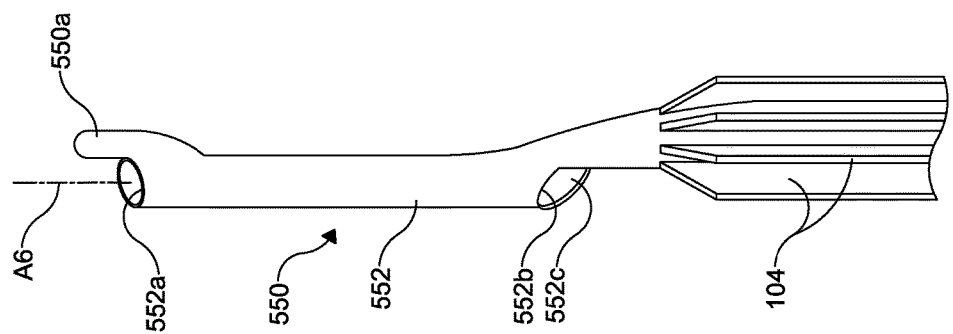
FIG. 28
FIG. 27

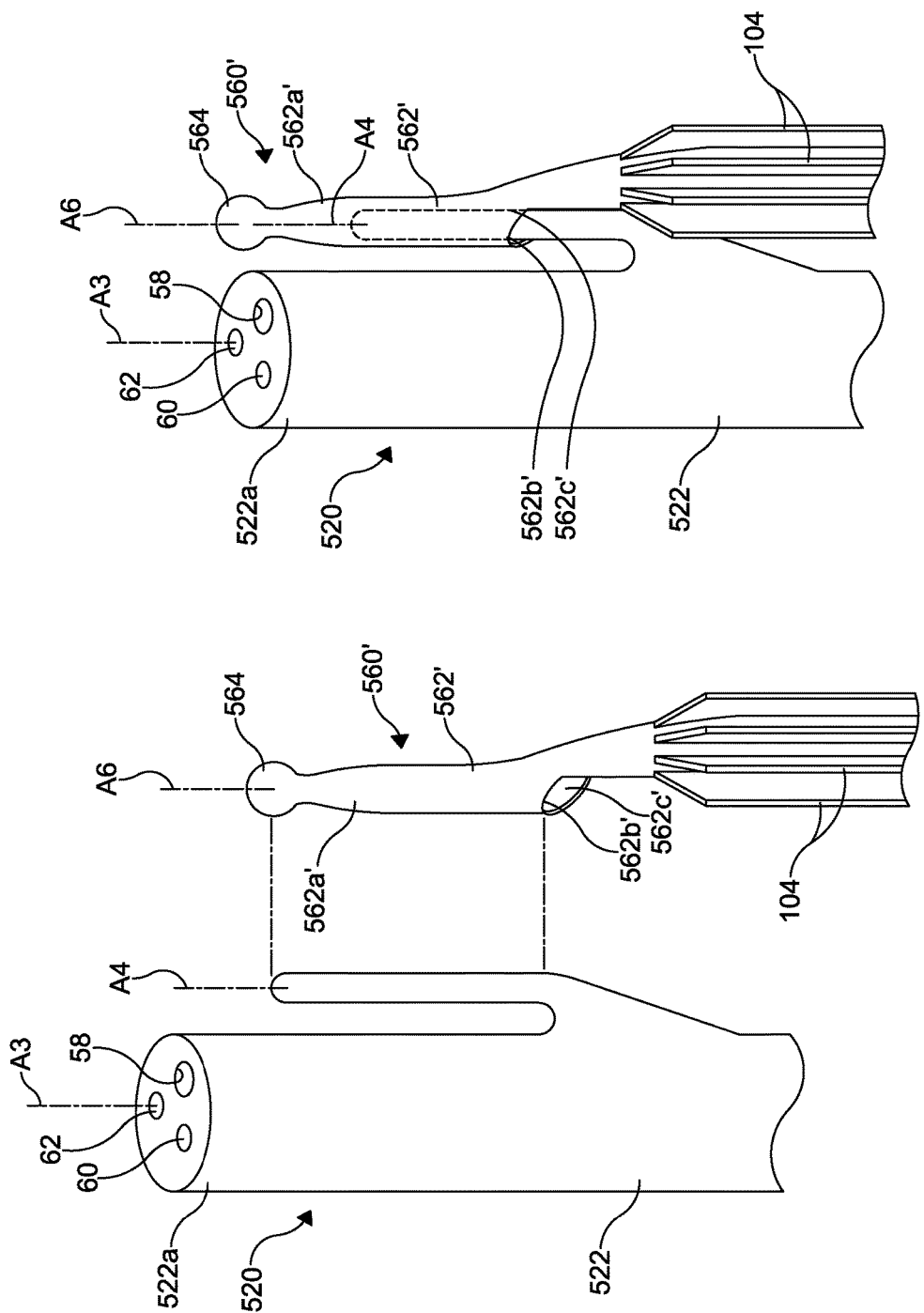

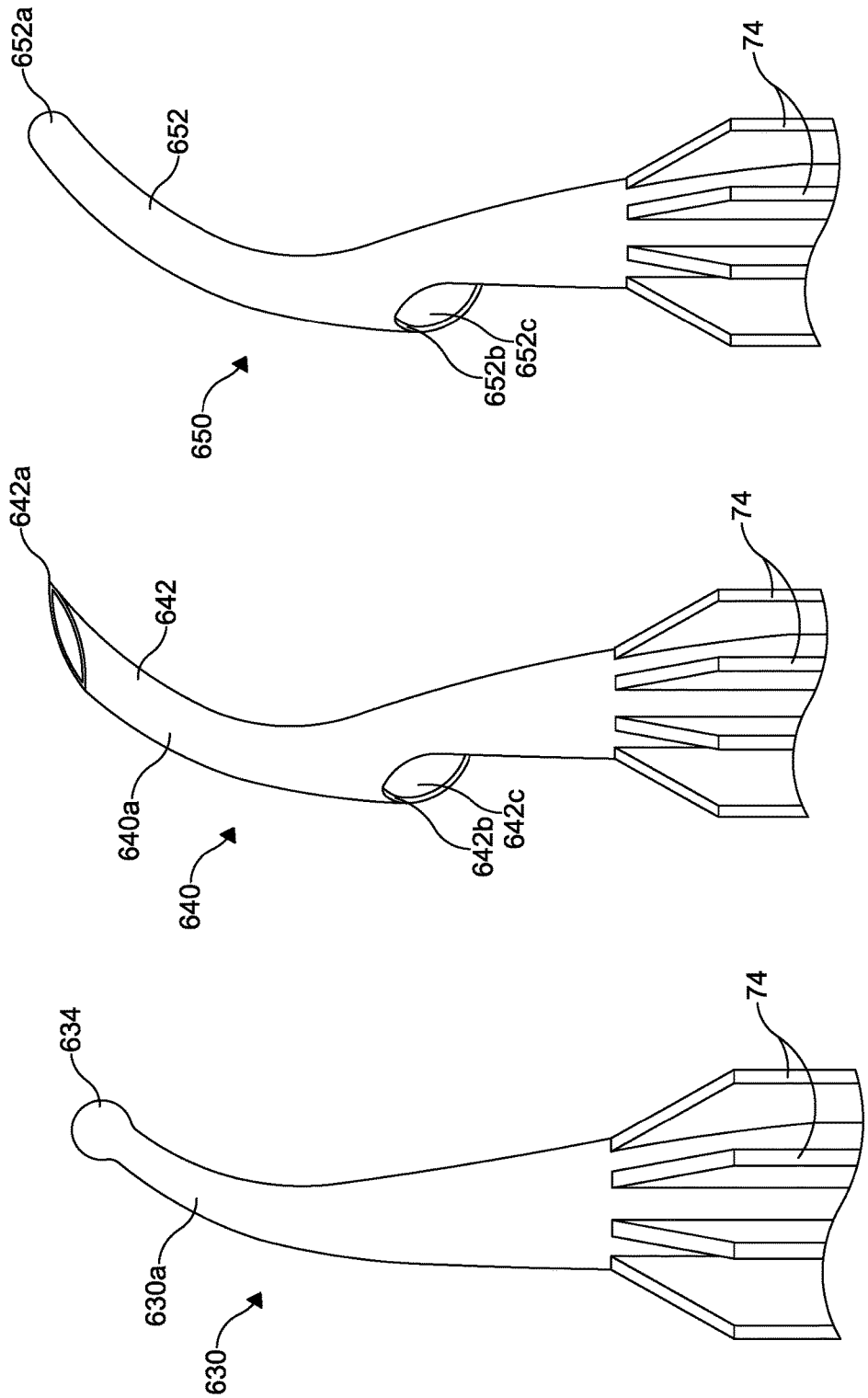

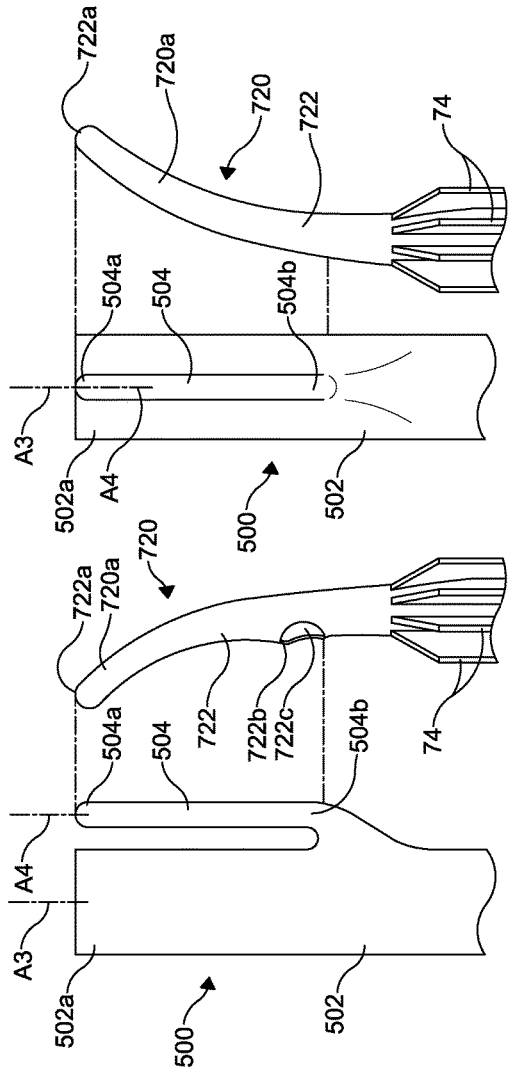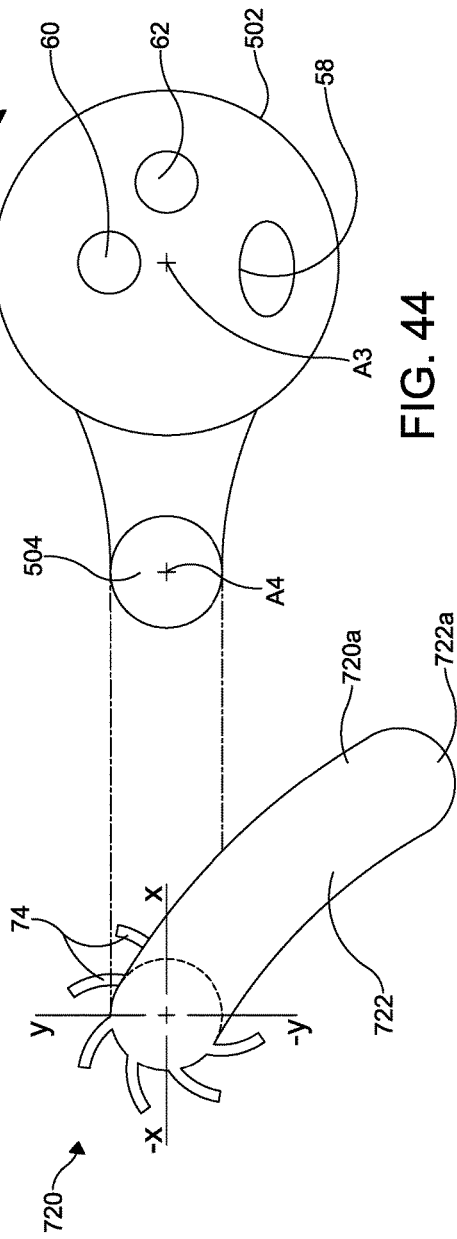
FIG. 43
FIG. 44
FIG. 42

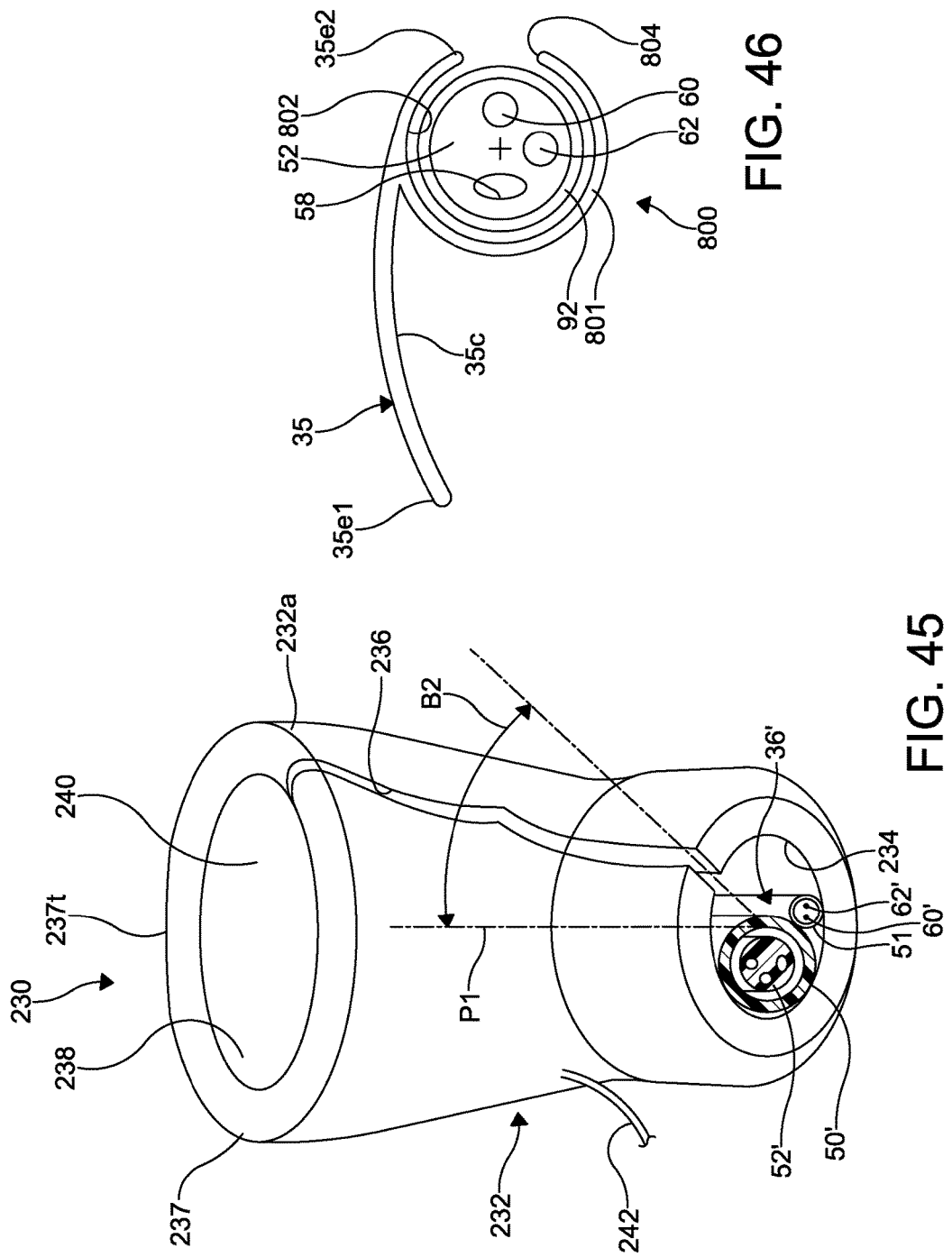

ENDOTRACHEAL TUBE INSERTION DEVICE

BACKGROUND OF THE INVENTION

This invention relates in general to a device for introducing an intubation device, such as an endotracheal tube, into a patient. In particular, this invention relates to an improved endotracheal tube insertion device that allows the user to simultaneously open the airway, view a patient's airway, accurately position an intubation device within the airway, and transmit a video image of the patient's airway to the operator and/or a medical professional located remotely from the patient.

Tracheal intubation typically includes placing a flexible plastic tube into the trachea or windpipe to maintain an open airway or to serve as a conduit through which to administer certain drugs. Tracheal intubation is frequently performed in critically injured, ill, or anesthetized patients to facilitate ventilation of the lungs, including mechanical ventilation, and to prevent the possibility of asphyxiation or airway obstruction. The most widely used method is orotracheal intubation, in which an endotracheal tube is passed through the mouth and vocal cords into the trachea.

Intubation is normally facilitated by using a conventional laryngoscope, a video laryngoscope, a flexible fiber-optic bronchoscope, or a flexible videoscope to identify the glottis and intubate the trachea of a patient, although other devices and techniques may be used. After the trachea has been intubated, a balloon cuff is typically inflated just above the far end of the tube to help secure the endotracheal tube in place, to prevent leakage of respiratory gases, and to protect the tracheobronchial tree from receiving undesirable material such as stomach acid. The endotracheal tube is then secured to the patient's face or neck and connected to a breathing device, such as a mechanical ventilator. Once there is no longer a need for ventilatory assistance and/or protection of the airway, the endotracheal tube is removed.

Many conventional tracheal intubations involve the use of a viewing instrument. For example, a conventional laryngoscope may consist of a handle containing batteries that power a light, and a set of interchangeable rigid blades, which are either straight or curved. This device is designed to allow the laryngoscopist to directly view the larynx.

Video laryngoscopes, flexible fiber-optic bronchoscopes, and flexible videoscopes have also become increasingly available. Video laryngoscopes are specialized rigid blade laryngoscopes that use a digital video camera sensor to allow the operator to view the glottis and larynx on a video monitor. In contrast to the conventional laryngoscope, a video laryngoscope allows the laryngoscopist to indirectly view the larynx. This provides a significant advantage in situations where the operator needs to see around an acute bend in order to see the glottis, and with otherwise difficult intubation procedures. Flexible videoscopes and fiber-optic bronchoscopes are not rigid instruments, and provide an even greater opportunity for visualizing the vocal cords due to their ability to fully manipulate the angle and position of the camera sensor and optics.

Successful endotracheal intubation requires adequate atraumatic laryngeal retraction, visualization of the vocal cords, positioning of the endotracheal tube, and a clear passage of the endotracheal tube into the trachea. Failure to adequately place the endotracheal tube within a few minutes often leads to permanent patient disability and even death. Currently available intubation instruments frequently lack the capability to meet one or more of these requirements.

Visualization of the vocal cords requires retraction of the tongue and laryngeal structures such as the epiglottis. Large tongues, excessive oropharyngeal soft tissue, stiff and immobile necks, and unique patient anatomy can make vocal cord visualization challenging. The ability to retract and physically align the oropharyngeal and laryngeal structures properly for direct or camera assisted viewing with a rigid blade may be difficult or impossible. Flexible videoscopes and fiber-optic bronchoscopes are not able to retract the tongue and laryngeal structures.

Direct rigid blade laryngoscopy allows for adequate retraction of laryngeal structures, but is often limited in providing vocal cord visualization in certain patient populations (e.g., thick, stiff, and/or immobile necks) and can be traumatic when trying to improve the view by manipulating the rigid blade between the teeth and stretching the laryngeal tissues.

Indirect rigid blade videoscopes improve the field of vision over direct rigid blades, but because the camera tip is permanently mounted on a singular site on the rigid blade, practitioners must still use rigid blade manipulation to further improve or achieve visualization of the vocal cords, often resulting in trauma as occurs with direct oral laryngoscopy. Despite manipulating the rigid blade videoscope and its fixed camera, the angle, curvature, and depth is often limited and visualization of the vocal cords may not be achieved.

Flexible videoscopes and fiber optic bronchoscopes provide for multiple angles and depths of view. Unfortunately, they do not provide a means to retract the tongue and laryngeal tissues that allow for visualization of the vocal cords. Instead, one must use a separate airway to retract the tongue and/or a second practitioner to manually retract or displace the tongue or the mandible. Although it is known to use flexible fiber-optic bronchoscopes or flexible videoscopes during intubation when the patient is under general anesthesia, the use of such devices has the disadvantage of typically requiring two skilled individuals to intubate the patient. It is difficult to manipulate soft tissue in the larynx with flexible fiber-optic bronchoscopes and flexible videoscopes, and despite these maneuvers for visualization, the passage, and the delivery of the endotracheal tube into the trachea is often inhibited by the laryngeal structures.

Despite proper tissue retraction and visualization of the vocal cords with currently available instruments such as a direct laryngoscope, indirect video laryngoscope, or a flexible videoscope, the delivery, placement, and passage of the endotracheal tube is often challenging. Stiff, rigid, and potentially traumatic stylets are frequently shaped and placed within the endotracheal tube, to give more control and guidance to the endotracheal tube tip in the direction of the visualized vocal cords. However, once the rigid stylet has been manually shaped, the user must work with that specific curvature and shape. If the curvature and shape is not satisfactory, the user must stop the laryngoscopy, remove all of the equipment, manually reshape the stylet, and start the procedure over from the beginning.

It is often the case with flexible videoscopes, flexible fiber-optic bronchoscopes, and rigid direct or indirect laryngoscopes, that visualization of the vocal cords may be achieved wherein placement of the endotracheal tube tip is at the vocal cords, or the flexible scope is within the trachea, but the passage of the endotracheal tube tip through the larynx between the vocal cords and into the trachea is obstructed. The leading edge of the endotracheal tube tip often collides with laryngeal structures, such as the arytenoids or the anterior wall of the trachea, preventing smooth passage of the endotracheal tube into the trachea.

In urgent and emergency situations, especially in locations remote from a hospital, the use of flexible video laryngoscopy or fiber-optic bronchoscopy may be limited, and personnel experienced in performing direct or indirect laryngoscopy are not always immediately available in settings that require emergency tracheal intubation.

It would therefore be desirable to provide an improved structure for a device for introducing an endotracheal tube into a patient, wherein such an improved device allows the user to simultaneously open the airway, view a patient's airway, accurately position an endotracheal tube or other intubation device within the airway, and if desired, transmit a video image of the patient's airway to the operator and/or a medical professional located remotely from the patient.

SUMMARY OF THE INVENTION

This invention relates to an improved structure for a device for introducing an endotracheal tube into a patient. The improved device is configured to allow the user to simultaneously open the airway, view a patient's airway, accurately position an endotracheal tube or other intubation device within the airway, and transmit a video image of the patient's airway to the operator and/or a medical professional located remotely from the patient.

In one embodiment, an intubation assembly rod is configured to have an endotracheal tube carried thereon and includes an elongated body having a distal end and a proximal end. The distal end of the intubation assembly rod body is tapered, rounded, or spherical, and defines a leading end of the intubation assembly rod. The intubation assembly rod includes a longitudinally extending channel configured such that an elongated member of a device to which the intubation assembly rod may be attached may be inserted into the channel.

In a second embodiment, an intubation assembly rod is configured to have an endotracheal tube carried thereon and includes an elongated body having a distal end and a proximal end, and a longitudinally extending conduit formed within the intubation assembly rod body.

In a third embodiment, an oxygen source cap is configured for use with an endotracheal tube insertion device and includes a body having a circumferentially extending wall defining a generally cylindrical outside surface, a first end, and an open second end defining a collar. An end wall is formed at the first end and a generally cylindrical fluid inlet extends radially outward of the wall, is in fluid communication with the open second end, and is configured for connection to source of oxygen. An intubation assembly rod is mounted within the body and extends to or through the end wall. The intubation assembly rod is configured to have an endotracheal tube carried thereon. The oxygen source cap is movably or fixedly mounted to the intubation assembly rod, and is further configured to be urged into contact with an endotracheal tube connector such that oxygen from the source of oxygen may then flow through the oxygen source cap into the endotracheal tube.

In a fourth embodiment, an intubation assembly rod is configured to have an endotracheal tube carried thereon and includes an elongated body having a distal end and a proximal end. A stop is attached at the proximal end of the body and is configured to retain the intubation assembly rod in a desired position within an endotracheal tube mounted on the intubation assembly rod.

Various aspects of this invention will become apparent to those skilled in the art from the following detailed description of the preferred embodiments, when read in light of the accompanying drawings.

BRIEF DESCRIPTION OF THE DRAWINGS

FIG. 3 is a bottom plan view of a portion of the endotracheal tube insertion device illustrated in FIG. 2.

FIG. 4 is a perspective view of the blade assembly illustrated in FIGS. 2 and 3.

FIG. 8 is an exploded perspective view of the intubation assembly rod illustrated in FIGS. 2 and 3.

FIG. 8A is a cross-sectional view taken along the line 8A-8A of FIG. 8.

FIG. 8B is an enlarged perspective view of a first embodiment of the first connecting member illustrated in FIG. 8.

FIG. 8C is an elevational view of an alternate embodiment of the first connecting member illustrated in FIGS. 8 and 8A.

FIG. 8D is an enlarged perspective view of a second embodiment of the first connecting member illustrated in FIG. 8.

FIG. 18 is a cross-sectional view taken along the line 18-18 of FIG. 17.

FIG. 19 is a cross-sectional view of a portion of the optical assembly illustrated in FIGS. 2 and 3 showing the intubation assembly rod mounted therein.

FIG. 22 is a perspective view of a portion of a second embodiment of the flexible member illustrated in FIG. 2.

FIG. 23 is a perspective view of a portion of a third embodiment of the flexible member illustrated in FIG. 2.

FIG. 24 is a perspective view of a portion of a fourth embodiment of the flexible member illustrated in FIG. 2.

FIG. 25 is a perspective view of a portion of a fifth embodiment of the flexible member illustrated in FIG. 2.

FIG. 26 is a perspective view of a portion of a sixth embodiment of the flexible member illustrated in FIG. 2.

FIG. 27 is a perspective view of a portion of a seventh embodiment of the intubation assembly rod illustrated in FIG. 8.

FIG. 28 is a perspective view of a portion of an eighth embodiment of the intubation assembly rod illustrated in FIG. 8.

FIG. 29 is a perspective view of a portion of a ninth embodiment of the intubation assembly rod illustrated in FIG. 8.

FIG. 36 is a perspective view of an alternate embodiment of the intubation assembly rod illustrated in FIG. 8 having a ball-shaped tip and shown prior to installation on the flexible member illustrated in FIG. 24.

FIG. 37 is a perspective view of the intubation assembly rod and the flexible member illustrated in FIG. 36 shown assembled.

FIG. 38 is a plan view of a portion of a twelfth embodiment of the intubation assembly rod illustrated in FIG. 8.

FIG. 39 is a plan view of a portion of a thirteenth embodiment of the intubation assembly rod illustrated in FIG. 8.

FIG. 40 is a plan view of a portion of a fourteenth embodiment of the intubation assembly rod illustrated in FIG. 8.

FIG. 42 is a top view of a portion of the flexible member illustrated in FIG. 22 and a fifteenth embodiment of the intubation assembly rod.

FIG. 43 is a side view of the portion of the flexible member and the intubation assembly rod illustrated in FIGS. 22 and 42.

FIG. 44 is an end view of the portion of the flexible member and the intubation assembly rod illustrated in FIGS. 22, 42, and 43.

FIG. 45 is a cross-sectional view of the optical assembly illustrated in FIG. 18 showing an alternate embodiment of the optical housing.

FIG. 46 is an end view of a third embodiment of the blade assembly according to the invention.

DETAILED DESCRIPTION OF THE PREFERRED EMBODIMENTS

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

Figure 1:
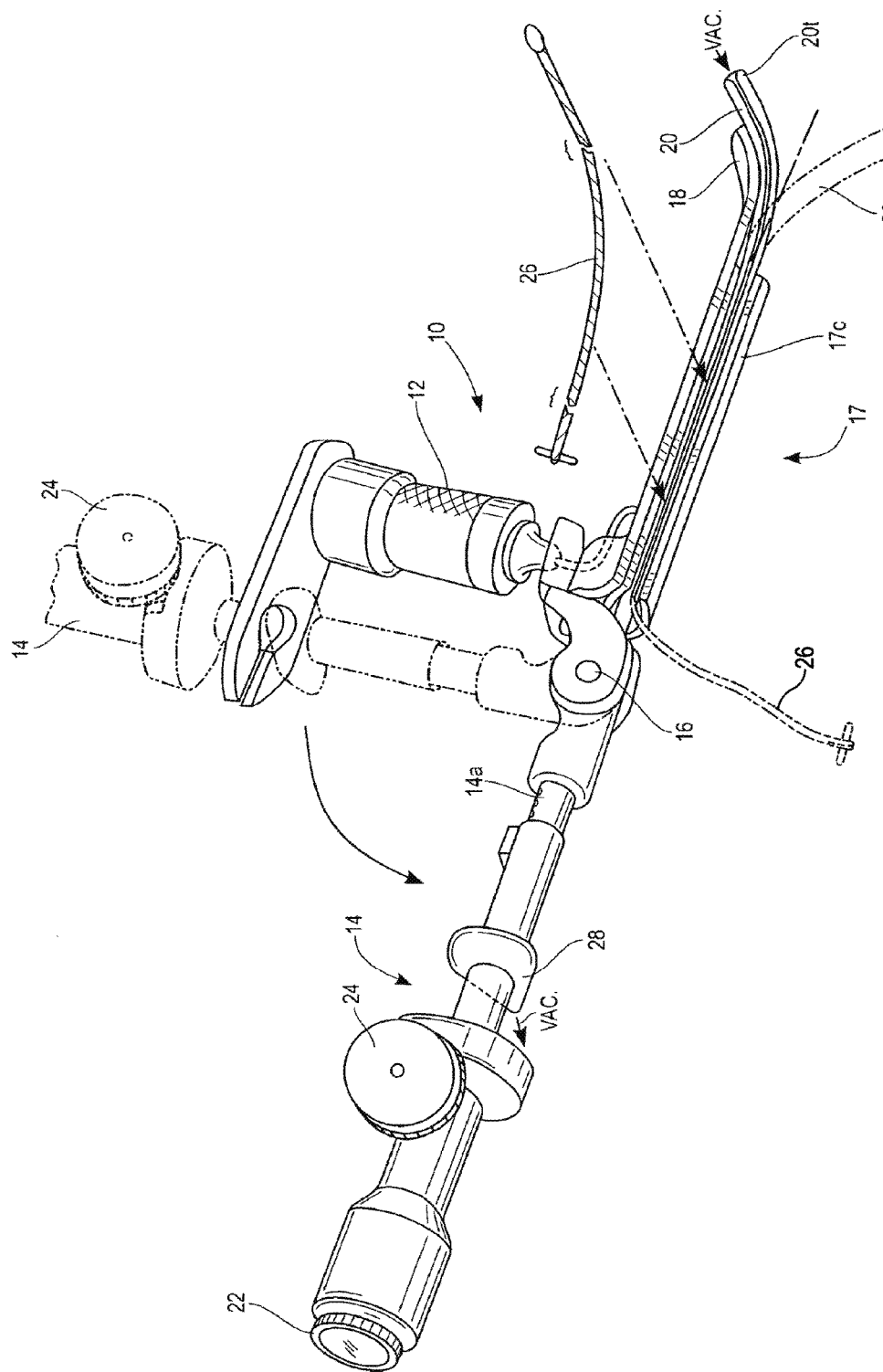
FIG. 1 is a perspective view of a known laryngoscope.

Referring now to the drawings, an embodiment of a known laryngoscope is indicated generally at 10 in FIG. 1. The illustrated laryngoscope 10 is described in detail in U.S. Pat. No. 7,563,227 to Gardner, the disclosure of which in incorporated herein in its entirety.

As shown in FIG. 1, the laryngoscope 10 includes a handle 12 and a viewing member 14. The viewing member 14 is made so that it can telescope between a first extended position and a second contracted position. A telescoping portion 14a is attached at a hinge 16 to a blade portion 17 having a blade 18. The viewing member 14 is configured such that it can be moved to first folded position parallel to the handle 12, as illustrated by phantom lines in FIG. 1.

The laryngoscope 10 also includes a flexible tubular member 20 adjacent to the blade 18. An eyepiece 22 and a ratcheting member 24 are operationally attached to the flexible tubular member 20. A generally C-shaped rigid channel 17c is provided on an underside of the blade 18 and is configured to hold the flexible tubular member 20 and to act as a guide for the flexible tubular member 20 when it is advanced. The flexible tube member 20 is configured such that it can be advanced forward (to the right when viewing FIG. 1) through the channel 17c so that a tip 20t of the flexible tube member 20 is distal of the end of the blade 18, to provide a better view of the patient's anatomy.

The flexible tube member 20 includes a plurality of longitudinally extending channels (not shown in FIG. 1). The channels may be configured for a variety of uses, including as a suction tube, or within which implements such as a fiber optic scope, illumination means, or a guidewire 26 may be mounted. The guidewire 26 is configured to be inserted through a conventional endotracheal tube, not shown in FIG. 1. The suction tube may be attached to a vacuum port 28, which may be further connected to a source of suction (not shown) external to the laryngoscope 10.

FIGS. 2 through 15 illustrate portions of an improved endotracheal tube insertion device, indicated generally at 30. The improved endotracheal tube insertion device 30 is an improved device for introducing an intubation device, such as a conventional endotracheal tube 92, shown in FIG. 9, into a patient. The improved endotracheal tube insertion device 30 is configured to allow the user to simultaneously open the airway, view a patient's airway, accurately position the endotracheal tube 92 within the airway, and transmit a video image of the patient's airway.

The improved endotracheal tube insertion device 30 includes a handle 32 attached to a blade assembly 34, an optical assembly 36, and a guided introducer intubation assembly 38. In the embodiment illustrated in FIGS. 2 and 3, the handle 32 is configured to be gripped by the hand of the user of the endotracheal tube insertion device 30.

A video monitor 40 is attached to a proximal end of the optical assembly 36 and is operationally connected to a video imaging device 60, shown in FIG. 7 and described below, within the optical assembly 36. In the illustrated embodiment, the video monitor 40 is mounted to a flexible optical assembly member or flexible member 52, described in detail below, such that it is movable or adjustable to any desired angle for ease in viewing. The video monitor 40 may also be releasably attached to the optical assembly 36 for remote viewing at a distance from the patient. Further, one or more additional video monitors 40 (not shown) may be positioned remotely from the endotracheal tube insertion device 30 and connected thereto by a wired or a wireless connection. Alternatively, the video monitor 40 may also be attached, including releasably attached, to the handle 32. In the illustrated embodiment, the video monitor has a substantially rectangular shape. Alternatively, the video monitor 40 may have any desired shape and size.

The handle 32 may also include a processor or controller 33 with Wi-Fi, or local area wireless technology that allows the endotracheal tube insertion device 30 to participate in computer networking. The processor or controller 33 may also have Bluetooth capability to allow a medical specialist to view, via the internet, any video images captured by the optical assembly 36. If desired, the controller 33 may be provided as a part of the video monitor 40, or at any other desired location in the improved endotracheal tube insertion device 30. Alternatively, in lieu of the handle 32, the handle and viewing member described in U.S. Pat. No. 7,563,227 may be provided.

The blade assembly 34 has an insertion member configured as an elongated blade body 35 attached to a channel member 37, as best shown in FIGS. 3 and 4. The elongated blade body 35 includes a first or distal end 35a, a second or proximal end 35b attached to the handle 32. As shown in FIGS. 3 and 4, the blade body 35 is substantially straight in the longitudinal direction and has an arcuate cross-sectional shape.

The channel member 37 includes a first or distal end 37a, and a second or proximal end 37b, defines a longitudinally extending channel 37c, and is attached to a first side 35c (lower side when viewing FIGS. 2 and 4) of the blade body 35. As also shown in FIG. 4, the channel member 37 is substantially C-shaped when viewed in cross-section and defines an elongated slot 37b that provides access to the channel 37c. Alternatively, the channel member 37 may have any desired cross-sectional shape, such as substantially oval, and substantially rectangular.

When viewed from the bottom of the blade body 35, as shown in FIG. 3, the channel 37c of the channel member 37 opens toward a first edge 35e1 of the blade body 35 (the upper edge when viewing FIG. 3). Alternatively, the channel 37c of the channel member 37 may open in any desired direction, such as toward a second edge 35e2 of the blade body 35 (the lower edge when viewing FIG. 3). As also shown in FIG. 3, the channel member 37 is positioned near the first edge 35e1 of the blade body 35 (the upper edge when viewing FIG. 3). Alternatively, the channel member 37 may be positioned near the second edge 35e2 of the blade body 35 (the lower edge when viewing FIG. 3), or at any position intermediate the first edge 35e1 and the second edge 35e2.

The blade body 35 may have any desired length, such as a length within the range of from about 8 cm to about 20 cm. Alternatively, the blade body 35 may be shorter than about 8 cm or longer than about 20 cm. The blade body 35 and the channel member 37 may be formed from any desired rigid or semi-rigid material, such as stainless steel and polyvinyl chloride (PVC). In the illustrated embodiment, the distal end 37a of the channel member 37 is spaced a short distance apart from the distal end 35a of the blade body 35, and the proximal end 37b of the channel member 37 terminates at the proximal end of the 35b of the blade body. The distal end 37a of the channel member 37 may be positioned at any desired distance from the distal end 35a of the blade body 35. If desired, the proximal end 37b of the channel member 37 may terminate prior to the proximal end of the 35b of the blade body (to the right of the proximal end of the 35b of the blade body when viewing FIG. 3) or may extend beyond the proximal end of the 35b of the blade body (to the left of the proximal end of the 35b of the blade body when viewing FIG. 3). The illustrated blade assembly 34 includes the substantially straight blade body 35. Alternatively, the blade assembly 34 may be formed with the curved blade body 44, described in detail below.

Figure 2:
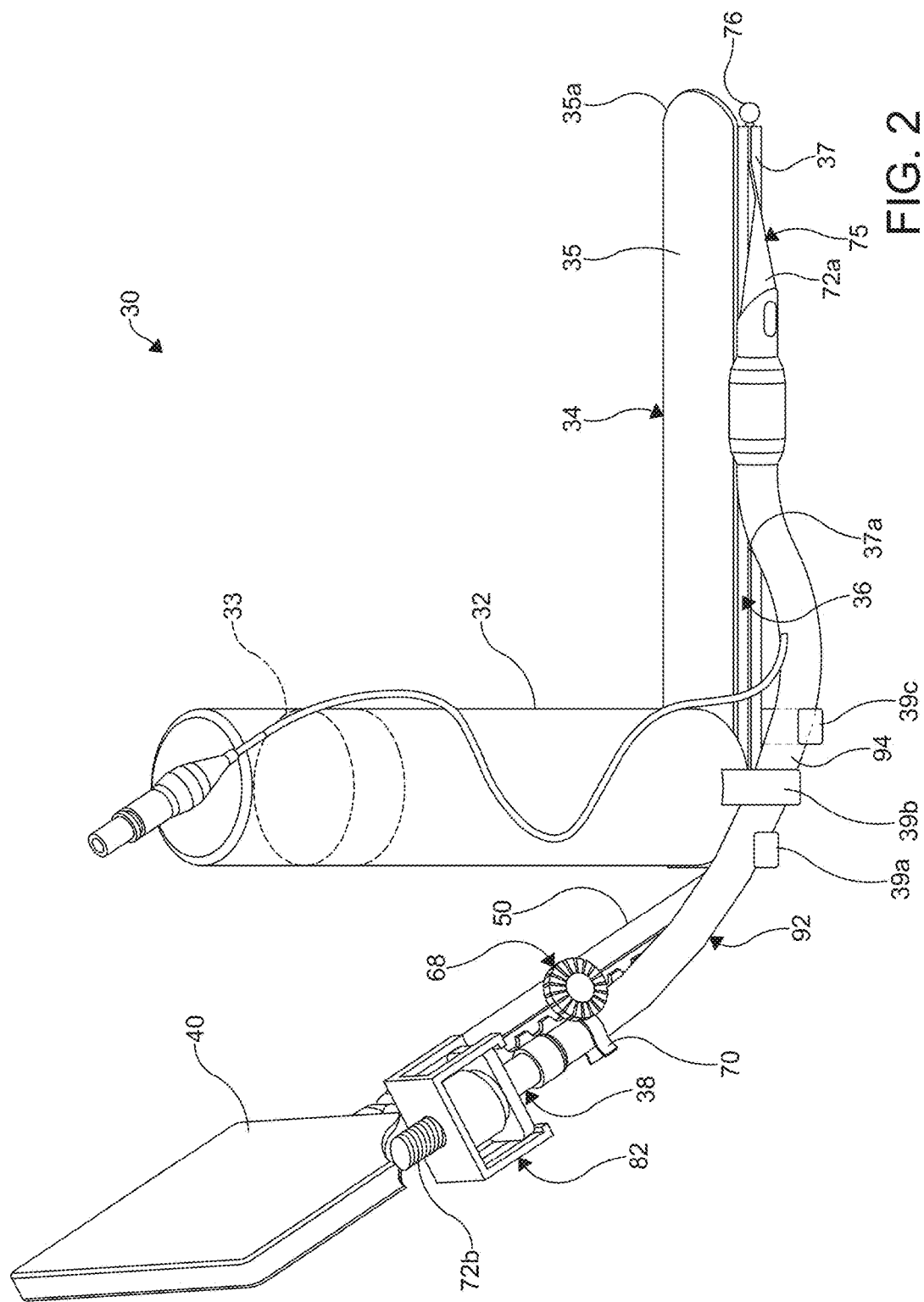
FIG. 2 is a perspective view of an embodiment of an improved endotracheal tube insertion device according to this invention.

If desired, endotracheal tube retention tabs may be provided on the blade assembly 34 of the endotracheal tube insertion device 30. For example, as shown in FIG. 2, two endotracheal tube retention tabs 39a extend outwardly and upwardly (when viewing FIG. 2) from the channel member 37 and one endotracheal tube retention tab 39b extends outwardly and downwardly (when viewing FIG. 2) from the handle 32. The endotracheal tube retention tabs 39a and 39b have a generally arcuate shape and are configured to allow the endotracheal tube 92 to be temporarily positioned and retained between the endotracheal tube retention tabs 39a and the endotracheal tube retention tab 39b. Alternatively, the tracheal tube retention tabs 39a and 39b may have any other desired shape suitable for retaining the endotracheal tube 92. Like the blade body 35 and the channel member 37, the endotracheal tube retention tabs 39a and 39b may be formed from any desired rigid or semi-rigid material, such as stainless steel and polyvinyl chloride (PVC). It will be understood that any desired number of endotracheal tube retention tabs 39a and 39b may be provided. Further, the endotracheal tube retention tabs 39a and 39b may be provided at any desired location on the blade assembly 34 and/or the handle 32.

Figure 11:
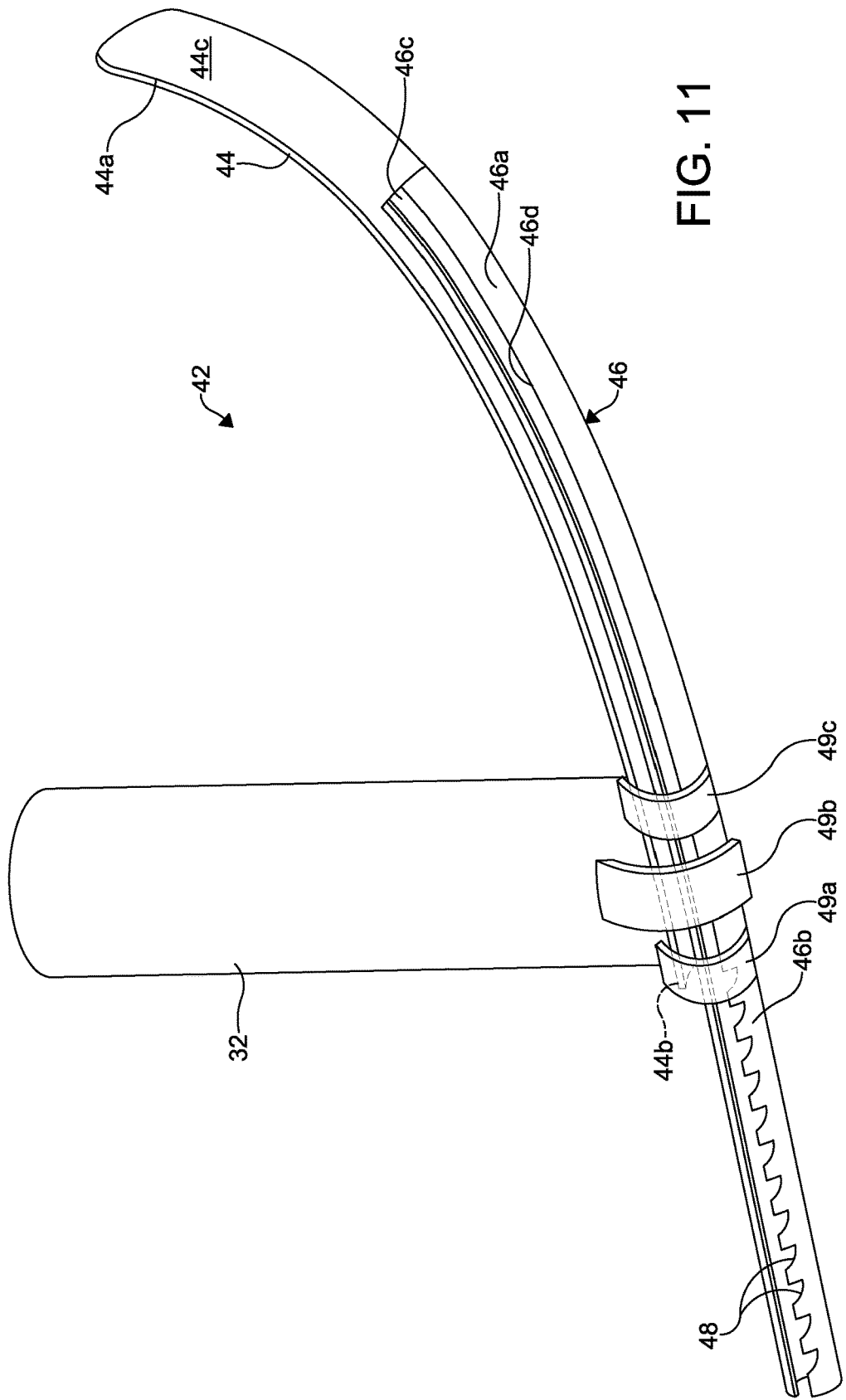
FIG. 11 is a perspective view of a second embodiment of the blade assembly illustrated in FIG. 4.

Referring to FIG. 11, a second embodiment of the blade assembly is shown at 42 attached to the handle 32. The blade assembly 42 has an elongated and upwardly curved blade body 44 attached to a channel member 46. The blade body 44 includes a first or distal end 44a, and a second or proximal end 44b attached to the handle 32. Like the blade body 35, the blade body 44 has an arcuate cross-sectional shape.

The channel member 46 is attached to a first side 44c (lower side when viewing FIG. 11) of the blade body 44, includes a first portion 46a and a second portion 46b, and defines a longitudinally extending channel 46c. The channel member 46 is substantially C-shaped when viewed in cross-section and defines an elongated slot 46d that provides access to the channel 46c. Alternatively, the channel member 46 may have any desired cross-sectional shape, such as substantially oval, and substantially rectangular. The second portion 46b of the channel member 46 extends beyond the proximal end 44b of the blade body 44 any desired distance, and includes a plurality of notches 48 formed in at least one side of the elongated slot 46d. A distal end of the first portion 46a of the channel member 46 may be positioned at any desired distance from the distal end 44a of the blade body 44. Like the channel 37c of the channel member 37, the channel 46c of the channel member 46 may open in any desired direction relative to the blade body 44, and may be laterally positioned near either longitudinal edge of the blade body 44, or any position intermediate thereof. The illustrated blade assembly 42 includes the curved blade body 44. Alternatively, the blade assembly 42 may be formed with the substantially straight blade body 35, described in detail above.

If desired, endotracheal tube retention tabs may also be provided on the blade assembly 42. For example, as shown in FIG. 11, two endotracheal tube retention tabs 49a extend outwardly and upwardly (when viewing FIG. 11) from the channel member 46 and one endotracheal tube retention tab 49b extends outwardly and downwardly (when viewing FIG. 11) from the handle 32. The endotracheal tube retention tabs 49a and 49b have a generally arcuate shape and are configured to allow the endotracheal tube 92 to be temporarily positioned and retained between the endotracheal tube retention tabs 49a and the endotracheal tube retention tab 49b. Alternatively, the endotracheal tube retention tabs 49a and 49b may have any other desired shape suitable for retaining the endotracheal tube 92. Like the endotracheal tube retention tabs 39a and 39b, the endotracheal tube retention tabs 49a and 49b may be formed from any desired rigid or semi-rigid material, such as stainless steel and polyvinyl chloride (PVC). It will be understood that any desired number of endotracheal tube retention tabs 49a and 49b may be provided. Further, the endotracheal tube retention tabs 49a and 49b may be provided at any desired location on the blade assembly 42 and/or the handle 32.

Figure 5:
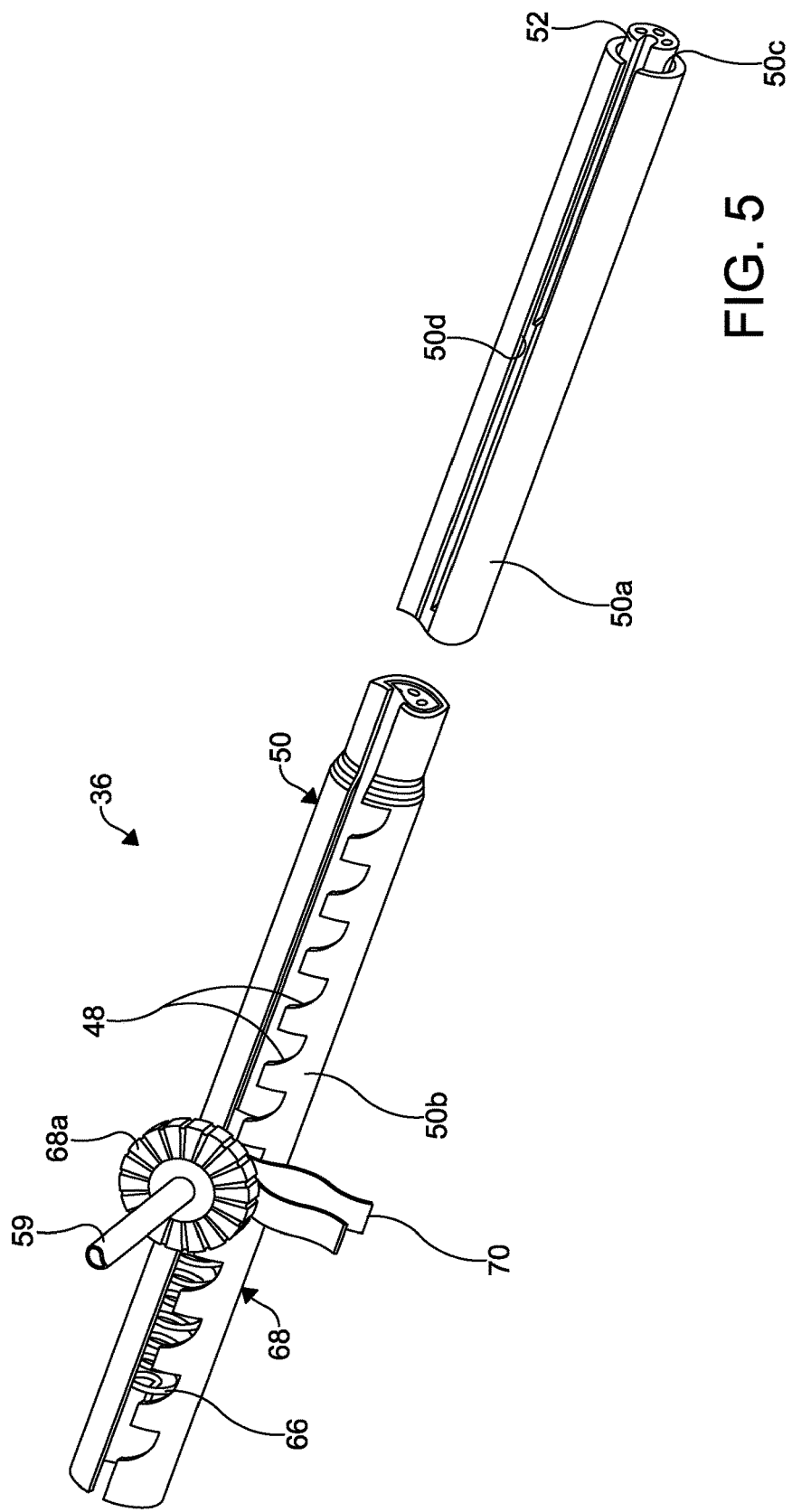
FIG. 5 is a perspective view of the optical assembly illustrated in FIGS. 2 and 3.
Figure 6:
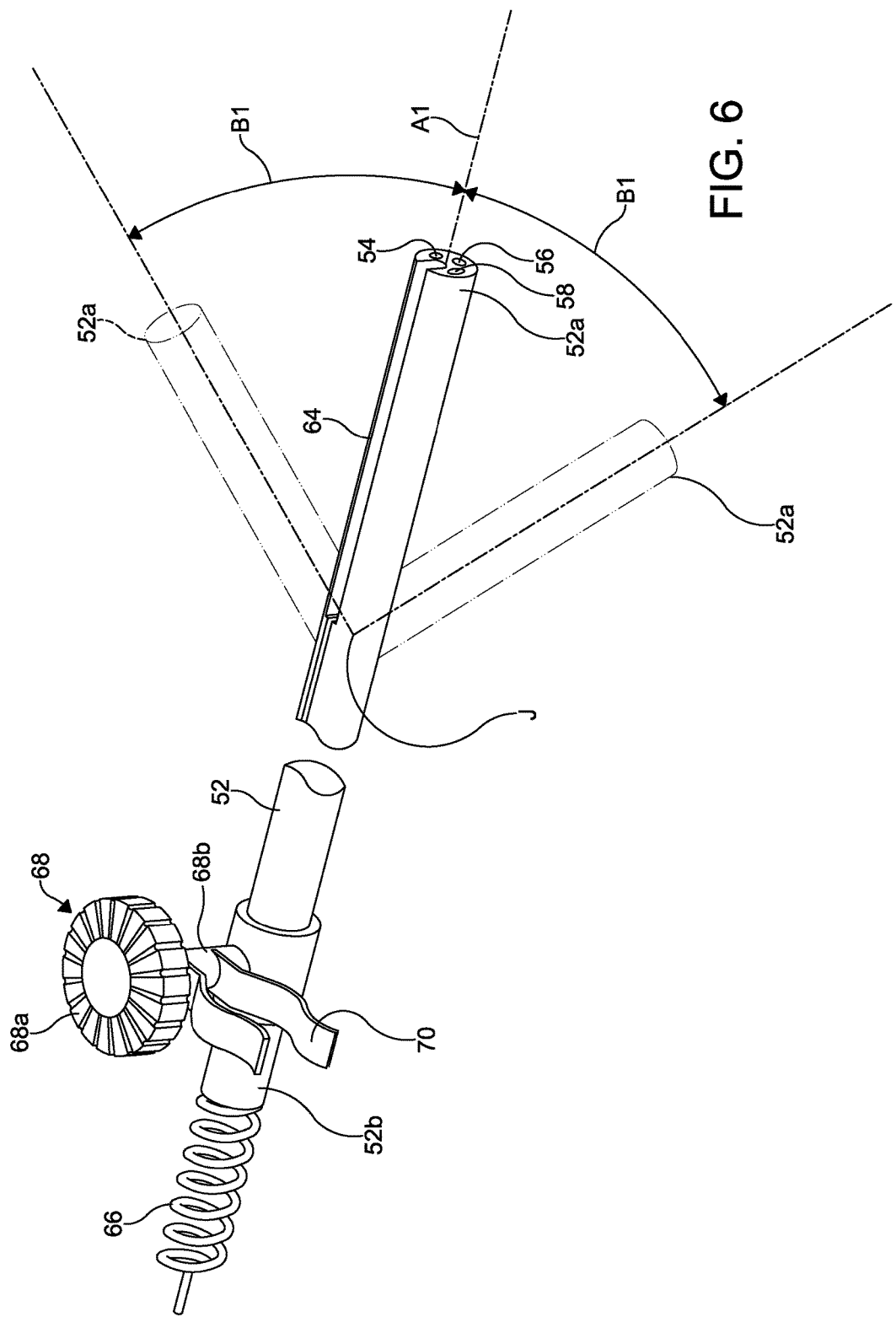
FIG. 6 is a perspective view of the optical assembly illustrated in FIG. 5 showing the optical housing removed.

As shown in FIG. 2, the optical assembly 36 is disposed within the channel 37c of the channel member 37. As best shown in FIGS. 5 through 7, the optical assembly 36 includes an optical housing 50 and the flexible member 52. The illustrated optical housing 50 includes a first portion 50a and a second portion 50b, and defines a longitudinally extending channel 50c. The optical housing 50 is substantially circular when viewed in cross-section and defines an elongated slot 50d that provides access to the channel 50c. Alternatively, the optical housing 50 may have any desired cross-sectional shape, such as substantially oval. In the illustrated embodiment of the optical housing 50, an inside diameter of the second portion 50b of the optical housing 50 is larger than an inside diameter of the first portion 50a. Alternatively, the inside diameter of the second portion 50b may be smaller than or equal to the inside diameter of the first portion 50a. The second portion also includes a plurality of the notches 48 formed in at least one side of the elongated slot 50d. The optical housing 50 may be formed from any desired rigid or semi-rigid material, such as PVC, wire-reinforced silicon, and stainless steel. Additionally, the optical housing 50 may be configured to be relatively more flexible at a portion of the optical housing 50 between the first and second portions 50a and 50b, thus allowing the user to bend the portion of the optical housing 50 that extends between the channel member 37 and the video monitor 40, as shown in FIG. 2.

Although the blade assembly 34 of the illustrated improved endotracheal tube insertion device 30 is shown having the channel member 37 attached thereto, the channel member 37 is not required. For example, the first portion 50a of the optical housing 50 illustrated in FIG. 5 may be attached to the first side 35c (lower side when viewing FIGS. 2 and 4) of the blade body 35 in the same manner that the channel member 37 is attached. In such an embodiment, the longitudinally extending channel 50c would function in the same manner as the longitudinally extending channel 37c of the channel member 37.

Figure 7:
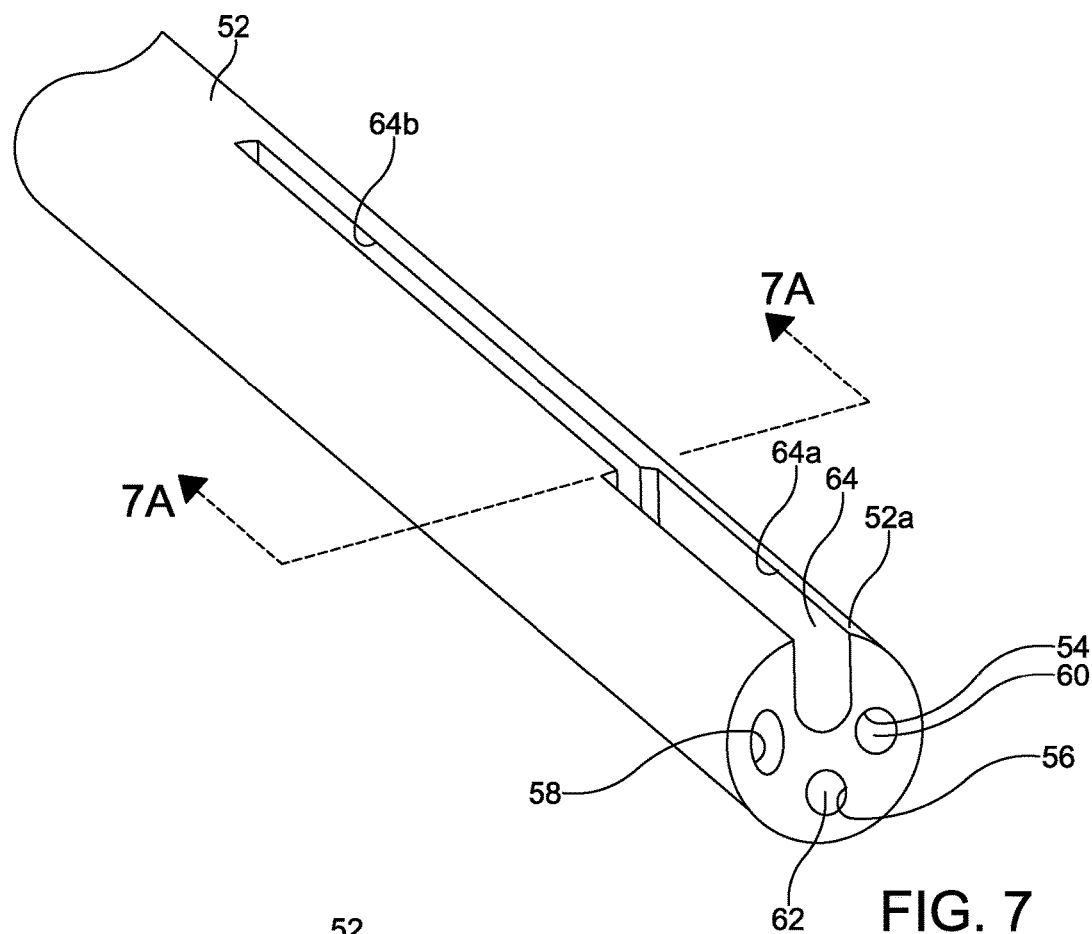
FIG. 7 is an alternate perspective view of the optical assembly illustrated in FIG. 6.

As best shown in FIGS. 6 and 7, the flexible member 52 is an elongated member having an axis A1, a substantially cylindrical shape and includes a first or distal end 52a and a second or proximal end 52b. Alternatively, the flexible member 52 may have any other desired cross-sectional shape, such as substantially oval, substantially hexagonal, and substantially rectangular. A plurality of longitudinally extending conduits is formed within the flexible member 52. As shown in FIG. 7, the flexible member 52 includes a first longitudinally extending conduit 54, a second longitudinally extending conduit 56, and a third longitudinally extending conduit 58. The video imaging device 60 is disposed in the first longitudinally extending conduit 54. In the illustrated embodiment, the video imaging device 60 is a Complementary Metal Oxide Silicon (CMOS) camera. Alternatively, the video imaging device 60 may be any desired video imaging device, such as a Charge-Coupled Device (CCD), fiber optic camera, and any other direct or indirect imaging device.

A light source 62 is disposed in the second longitudinally extending conduit 56. In the illustrated embodiment, the light source 62 is an LED lamp or an incandescent bulb mounted at the distal end 52a of the flexible member 52. Alternatively, the light source 62 may be any other source of light. Additionally, the light source 62 may be a fiber optic cable connected at its proximal end to a source of illumination (not shown), such as an LED lamp, an incandescent bulb, or any other desired light source. The video imaging device 60 and the light source 62 are operationally connected to the video monitor 40 and/or the controller 33 by one or more flexible electrical and/or optical connectors, shown at 66 in FIG. 6.

The third longitudinally extending conduit 58 is configured as a suction tube and is connected to a vacuum port, such as a vacuum port 59 extending outward of the knob 68a, as shown in FIG. 5. Although described as a suction tube, the conduit 58 may also be used to provide oxygen to a patient. The conduit 58 may further be used to introduce tools, such as medical instruments (not shown) into the patient. In the illustrated embodiment, the flexible member 52 has an outside diameter of about 4 mm. Alternatively, the flexible member 52 may have any other outside diameter.

Figure 7A:
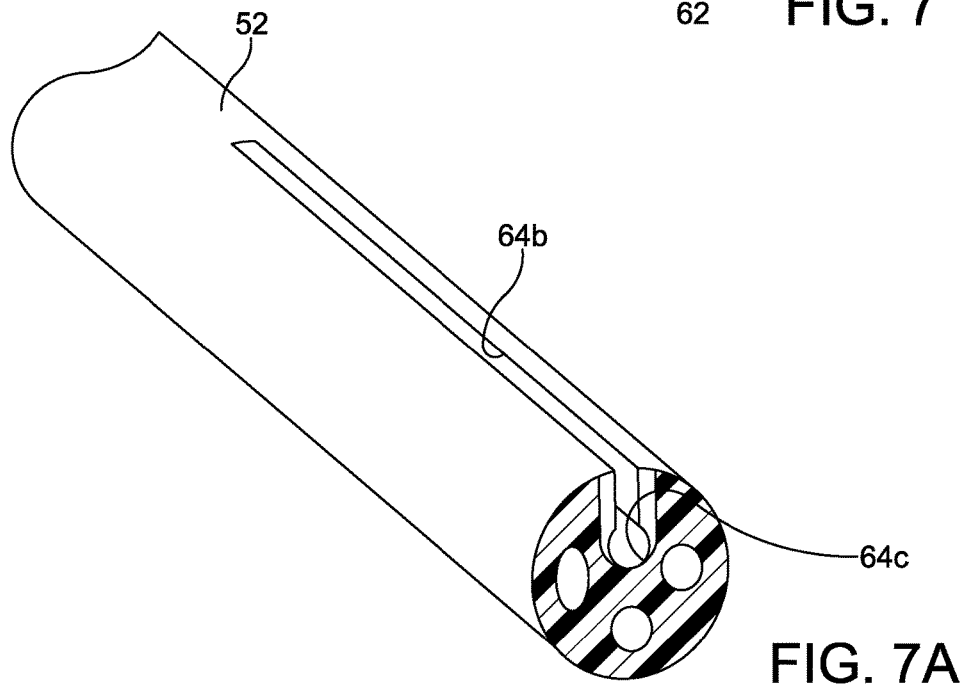
FIG. 7A is a cross-sectional view taken along the line 7A-7A of FIG. 7.

The distal end 52a of the flexible member 52 also includes an intubation assembly guide channel 64, the purpose for which will be described below. The illustrated intubation assembly guide channel 64 includes a first portion 64a, a second portion 64b proximal of the first portion 64a, and a third portion 64c adjacent to, and radially inward of, the second portion 64b, as shown in FIG. 7A. In the illustrated embodiment, the third portion 64c is wider than the second portion 64b for reasons that will be described below. Specifically, the third portion 64c is substantially cylindrical and has an inside diameter about the same size at an outside diameter of an elongated guide member portion 78 of a guide rail 75, described below. Alternatively, the third portion 64c may have any other desired cross-sectional shape, such as substantially oval, substantially hexagonal, and substantially rectangular. If desired, the third portion 64c may have any desired inside diameter, such as an inside diameter larger than the outside diameter of the guide member portion 78 of the guide rail 75. Additionally, the first portion 64a has a relatively wide longitudinal opening and the second portion 64b has a longitudinal opening smaller than the longitudinal opening of the first portion 64a.

In the illustrated embodiment, the intubation assembly guide channel 64 has a length within the range of about 3 cm to about 7 cm, the first portion 64a has a length within the range of about 0.5 cm to about 2 cm, and the second and third portions 64b and 64c have a length within the range of about 2 cm to about 5 cm. Alternately, the intubation assembly guide channel 64, and each of the first, second, and third portions 64a, 64b, and 64c may have any desired length and width.

Further, it will be understood that the flexible member 52 maybe formed without the relatively wide first channel portion 64a, and with only the second and third portions 64b and 64c, such as shown in FIG. 7A. In an embodiment of the flexible member 52 having only the second and third portions 64b and 64c of the intubation assembly guide channel 64, each of the second and third portions 64b and 64c may have any desired length, such as a length within the range of about 2 cm to about 7 cm.

In the illustrated embodiment, the first and second longitudinally extending conduits 54 and 56 have a circular cross sectional shape, and the third longitudinally extending conduit 58 has an oval cross sectional shape. Alternatively, the first, second, and third longitudinally extending conduits 54, 56, and 58 may have any desired cross sectional shape. The flexible member 52 may be formed from any desired flexible or semi-flexible material, such as silicon, rubber, wire-reinforced silicon, wire-reinforced rubber, and polymers. Additionally, the flexible member 52 may be configured to be relatively more flexible at its distal end 52a and relatively less flexible at its proximal end 52b, thus providing greater flexibility within a patient's airway, and less flexibility, and therefore greater control, for the user when handling the proximal end 52b.

The distal end 52a of the flexible member 52 also includes a mechanism (not shown) for moving a portion of the distal end 52a, so as to view desired portions of the patient's air passage. The mechanism (not shown) defines a joint J, may be mechanically or electrically actuated, and is configured to move the distal end 52a through an angle B1. In the illustrated embodiment, the angle B1 is about +/−90 degrees from the axis A1 of the flexible member 52. Additionally, the distal end 52a of the flexible member 52 may be articulating so as to be configured to move in any radial direction, thus the joint J may be configured as an articulating joint.

The mechanism for moving a portion of the distal end 52a may be controlled by a control device 68 at the proximal end 52b of the flexible member 52. The illustrated control device 68 includes the rotatable knob 68a and a mounting post 68b. Alternatively, the control device 68 may located at any other desired location on the flexible member 52 or any other desired location on the improved endotracheal tube insertion device 30. The mechanism for moving a portion of the distal end 52a, and therefore the movement of the distal end 52a of the flexible member 52, may be controlled by the control device 68, thus allowing the user to move the distal end 52a of the flexible member 52 to a desired location and to lock or retain the distal end 52a in the position selected by the user. As shown in FIGS. 5 through 7, an attachment member 70 is attached to the mounting post 68b of the control device 68. The attachment member 70 may be any device configured to retain the guided introducer intubation assembly 38 and its attached endotracheal tube 92, described below, relative to the improved endotracheal tube insertion device 30, and more specifically relative to the flexible member 52. Alternatively, the attachment member 70 may be mounted to any desired portion of the improved endotracheal tube insertion device 30, including the handle 32 and the video monitor 40.

The guided introducer intubation assembly 38 includes an intubation assembly body configured as a rod 72, best shown in FIGS. 8 and 8A, which defines an introducer or bougie. The rod 72 is substantially cylindrical and has an elongated body having a first or distal end 72a and a second or proximal end 72b. Alternatively, the rod 72 may have any other desired cross-sectional shape, such as substantially oval, substantially hexagonal, and substantially rectangular. The distal end 72a of the rod 72 is tapered or substantially cone-shaped and defines a leading end of the rod 72. The rod 72 includes a plurality of longitudinally and radially outwardly extending ribs 74. In the illustrated embodiment, the rod 72 is shown prior to being inserted into the endotracheal tube 92, such as the endotracheal tube 92 shown in FIG. 9. As shown, the ribs 74 have an arcuate cross-sectional shape. The ribs 74 may extend for any desired length of the rod 72 and taper toward the distal end 72a.

The illustrated rod 72 includes a guide system configured to guide the endotracheal tube 92 into the trachea, and configured for releasable attachment to the flexible member 52 of the optical assembly 36. In the illustrated embodiment, the guide system is a guide rail 75. The illustrated guide rail 75 includes a substantially spherical tip 76 at a distal end of the guide member portion 78. The guide member portion 78 may be attached to the rod 72 by a substantially flat bridge 80 that extends between the rod 72 and the guide member portion 78. Alternatively, the guide member portion 78 may be attached directly to the rod 72 without the bridge 80. Although illustrated as spherical, the tip 76 may have other shapes, such as substantially ovoid, or having the shape of a rectangular prism or a triangular prism. It will be understood that the tip 76 is not required, and the distal end of the guide member portion 78 may have a rounded or tapered surface. Additionally, the tip 76 may be of any size and have any shape that fits within the first portion 64a. Further, the guide member portion 78 is configured to fit within the third portion 64c, and has a diameter large enough that it is laterally retained, i.e., that it cannot fall or be otherwise laterally removed through the second portion 64b of the guide channel 64. In the illustrated embodiment, the guided introducer intubation assembly 38 has an overall length within the range of about 40 cm to about 50 cm. Alternatively, the guided introducer intubation assembly 38 may have any other desired length.

As best shown in FIG. 8, the guide member portion 78 has a substantially cylindrical shape and a length L1, measured from the spherical tip 76, of about 5 cm. Alternatively, the guide member portion 78 may have any other desired cross-sectional shape, such as substantially oval, substantially hexagonal, and substantially rectangular. Further, the guide member portion 78 may have any desired length L1, such as a length from about 4 cm to about 6 cm. The illustrated bridge 80 extends from a point near the spherical tip 76 to a point near a proximal end of the guide member portion 78. The bridge 80 may have any width and length, and may be attached to the guide member portion 78 at any point proximal to the spherical tip 76 or proximal to a distal end of the guide member portion 78 if the guide member portion 78 is formed without the tip 76. Alternatively, the bridge 80 may be located at any desired portion of the rod 72. The substantially cylindrically shaped portion of the rod 72 thus begins at a point about 7 cm from the spherical tip 76. Alternatively, the substantially cylindrically shaped portion of the rod 72 may begin at any desired distance from the spherical tip 76, such as a distance from about 6 cm to about 8 cm. The bridge 80 may have any desired thickness such that the bridge 80 may extend through the second portion 64b of the guide channel 64, as described in detail below.

The rod 72 and the ribs 74 formed thereon, and the guide rail 75 and its component parts; i.e., the guide member portion 78, the substantially spherical tip 76, and the bridge 80, may be formed from any flexible or semi-flexible material, such as silicon, rubber, wire-reinforced silicon, wire-reinforced rubber, and polymers. Additionally, the rod 72 may be configured to be relatively more flexible at its distal end 72a and relatively less flexible at its proximal end 72b, thus providing greater flexibility within a patient's airway, and less flexibility, and therefore greater control, for the user when handling the proximal end 72b.

If desired, in lieu of the ribs 74, the ribbed portion of the rod 72 may be configured to include a solid, an expandable, or a hollow inflatable portion, a leading edge of which may be formed with a tapered or substantially frusto-conical shaped transition segment where the ribs 74 would otherwise begin. This solid, expandable, or inflatable portion of the rod 72 may have, or may be inflated to have a desired outside diameter corresponding to inside diameter of an endotracheal tube 92.

Alternatively, the improved endotracheal tube insertion device 30 may be provided with a plurality of rods 72, each with ribs 74 having a different outside diameter corresponding to the inside diameter of one of a plurality of endotracheal tubes 92 having different inside diameters. Additionally, the improved endotracheal tube insertion device 30 may be provided with a plurality of rods 72 formed without ribs, each of the plurality of rods having a different outside diameter corresponding to the inside diameter of one of a plurality of endotracheal tubes 92 having different inside diameters. It will be understood that each embodiment of the rod described herein, including the embodiment of the rod having the hollow inflatable member described above, may be formed with the tapered or substantially cone-shaped leading end as described above and illustrated, for example, at 72a in FIG. 8.

The flexible or semi-flexible material and arcuate cross-sectional shape of the ribs 74 allow the ribs to be generally flexible; i.e., radially compressible such that the outside diameter of the ribs may vary and such that the rod 72 may be used in endotracheal tubes 92 having varying inside diameters, such as inside diameters from about 3.0 mm, or the size of a conventional pediatric endotracheal tube 92, to about 9.0 mm, or the size of a convention adult endotracheal tube 92. Alternatively, the endotracheal tube 92 may have an inside diameter smaller than about 3.0 mm or larger than about 9.0 mm. Preferably, the ribs 74 will engage the inside surface of the endotracheal tube 92 in which the rod 72 has been inserted, whether the inside surface has a small inside diameter, such as about 3.0 mm or a larger inside diameter, such as about 9.0 mm.

The proximal end 72b of the rod 72 includes threads 73 configured for connecting the rod 72 to a first connecting member 82, shown in FIGS. 8 and 8B. The first connecting member 82 includes a base 84 having a plurality of arms 86 extending outward therefrom. The arms 86 include inwardly extending flanges or locking members 88. A substantially cylindrical body 90 also extends outwardly from the base 84 between the arms 86. A longitudinally extending threaded channel 95 is formed at least through the base 84. The first connecting member 82 is configured to be attached to the threads 73 of the rod 72. This threaded connection allows the user to adjust the longitudinal position of the first connecting member 82 relative to the rod 72, i.e., in the direction of the arrow 93 in FIG. 8, by rotating the attachment first connecting member 82 clockwise or counterclockwise. This threaded connection further allows the user to shorten or lengthen the rod 72 relative to the length of the tube body 94 of the endotracheal tube 92 that will be mounted on the rod 72. If desired, a portion of the proximal end 72b of the rod 72 that extends outward of the first connecting member 82 may be removed by the user, such as by cutting. It will be understood that the rod 72 may be shortened or lengthened relative to the length of the tube body 94 by any other means.

Referring to FIG. 8C, a first alternate embodiment of the first connecting member is shown at 82'. The first connecting member 82' is similar to the first connecting member 82, however, the cylindrical body 90 of the first connecting member 82' includes a portion 90a extending outward of the base 84 for connection to a source of oxygen for example. The portion 90a may have any desired inside and outside diameter, and may have any desired length, which may include a length equal to a length of the cylindrical body 90. Alternatively, the portion 90a may have a length shorter or longer than a length of the cylindrical body 90. The portion 90a may be configured for attachment to a source of oxygen or air, in the same manner that the cylindrical body 98b of the conventional connector 98 shown in FIG. 9 is configured for attachment to a source of oxygen or air.

If desired, air flow passageways 91 may be formed through base 84 within the portion 90a, as shown in FIG. 8C. The air flow passageways 91 define a flow path for oxygen or air from the source of oxygen or air to the endotracheal tube 92.

Referring to FIG. 8D, a second alternate embodiment of the first connecting member is shown at 182. The first connecting member 182 is similar to the first connecting member 82, and includes a base 184 having a plurality of arms 186 extending outward therefrom. The illustrated embodiment of the first connecting member 182 includes a first pair of arms 186*a* and a second pair of arms 186*b*, only one of which is shown in FIG. 8D, opposite the first pair of arms 186*a*. Each of the arms 186*a* and 186*b* include inwardly extending locking members 188. A substantially cylindrical body 190 also extends outwardly from the base 184 between the arms 186*a* and 186*b*. A longitudinally extending threaded channel 195 is formed in the base 184. Side walls 192 extend outwardly from the base 184 in a direction away from the arms 186*a* and 186*b* at side edges of the base 184. The side walls 192 are extensions of the arms 186*a* and 186*b* and define opening tabs that, when compressed or urged toward one another, such as by the user, the first pair of arms 186*a* and the second pair of arms 186*b* are urged away from each other, thus allowing the user to more easily attach and detach the flange 98*a* of the connector 98 from the first connecting member 182. If desired, the side walls 192 may be formed on any of the embodiments of the first connecting member, such as the first connecting members 82 and 82'.

Figure 9:
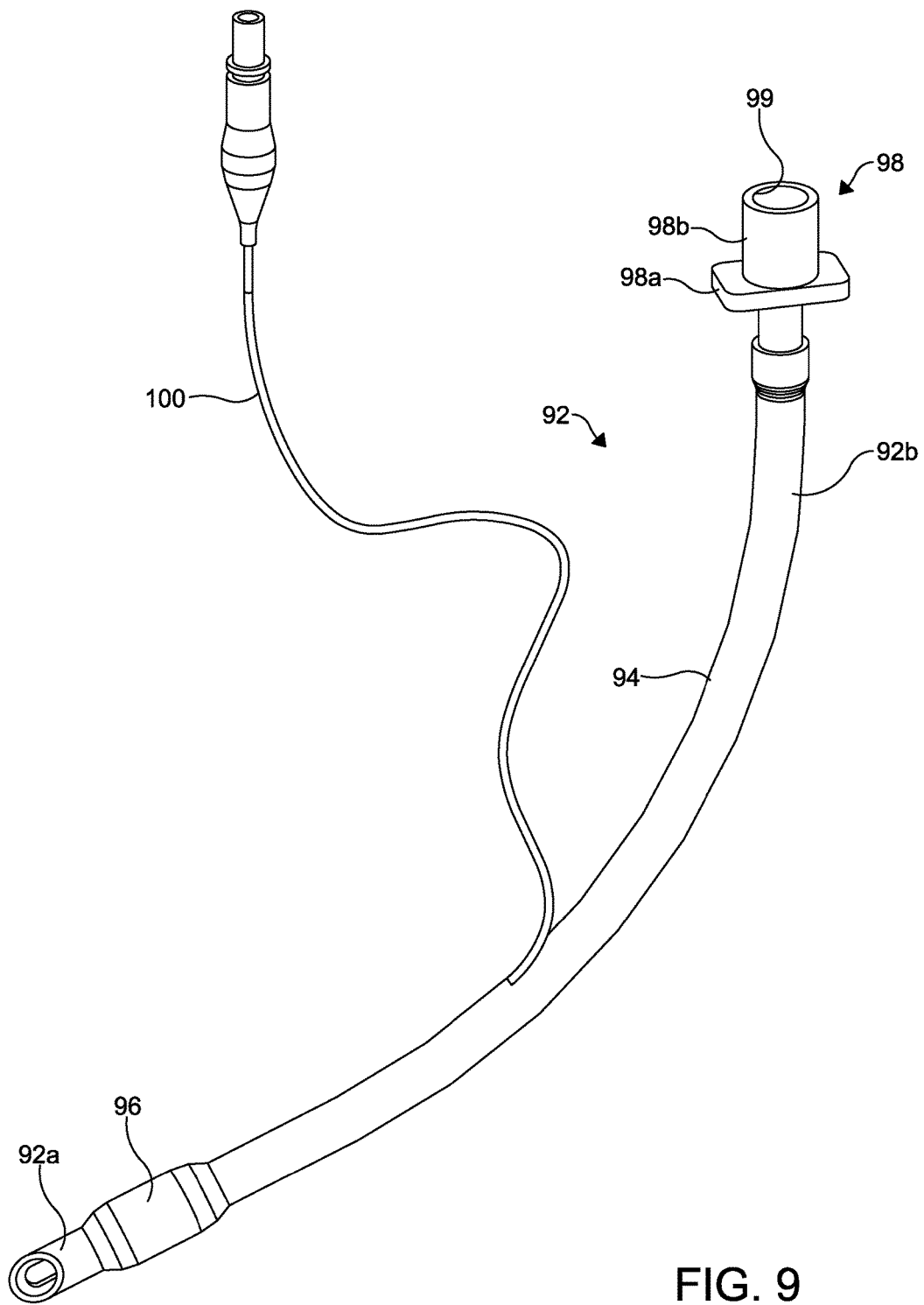
FIG. 9 is a perspective view of the conventional endotracheal tube illustrated in FIGS. 2 and 3.

The guided introducer intubation assembly 38 further includes a conventional endotracheal tube, such as shown at 92 in FIG. 9. The endotracheal tube 92 is configured for attachment to the rod 72, as best shown in FIG. 2. The endotracheal tube 92 has a first or distal end 92*a* and a second or proximal end 92*b*. The endotracheal tube 92 further includes a tube body 94 having balloon cuff 96 at the distal end 92*a*, and a conventional connector 98 at the proximal end 92*b* thereof. As described in detail above, the tube body 94 of the endotracheal tube 92 may have an inside diameter of from about 3.0 mm to about 9.0 mm.

The connector 98 includes a flange 98*a* having a substantially cylindrical body 98*b* extending outwardly from the flange 98*a*. The body 98*b* has a longitudinally extending channel 99 formed therethrough. An air inflation tube 100 is attached to the balloon cuff 96 and configured for attachment to a source of air, such as a syringe.

The connector 98 is configured for attachment to the first connecting member 82. When attached, the body 98*b* is inserted into the body 90 of the first connecting member 82 and the flange 98*a* is snap fit between the arms 86 and retained between the arms 86 by the locking members 88. The body 98*b* of the connector 98 has an outside diameter of about 15 mm. Alternatively, the body 98*b* may have any other outside diameter. If desired, the conventional connector 98 and the first connecting member 82 may be configured such that the body 90 of the first connecting member 82 is smaller than, and may be inserted into the body 98*b* of the connector 98.

When the guided introducer intubation assembly 38 is assembled, the rod 72 is inserted through the channel 99 of the connector 98 and into the tube body 94 of the conventional endotracheal tube 92 until the guide member portion 78 extends outward of the distal end 92*a* of the endotracheal tube 92. When the rod 72 is mounted within the tube body 94 of the endotracheal tube 92, the longitudinally extending spaces between the ribs 74 define flow paths for oxygen from a source of oxygen (not shown) to the patient during intubation and before the guided introducer intubation assembly 38 is removed.

Although not illustrated, the rod 72 may be formed as a hollow member and may also have one or more radially extending holes or perforations along its length to facilitate the delivery and flow of oxygen from the proximal end 72*b* of the rod 72.

Advantageously, the improved endotracheal tube insertion device 30, and particularly the shape and tapered leading edge of the ribs 74 (or the alternative ribbed portion of the rod 72 configured as a hollow inflatable member), the smooth, tapered or cone-shaped leading end 72*a* of the rod 72. The spherical tip 76, and the guide member portion 78 of the improved guided introducer intubation assembly 38 is configured to avoid being caught on laryngeal structures as the guided introducer intubation assembly 38 and the leading edge or distal end 92*a* of the endotracheal tube 92 is advanced into the patient's airway, thus facilitating the delivery of the endotracheal tube 92 between the vocal cords and preventing trauma or injury to the vocal cords and other parts of the airway.

Figure 10:
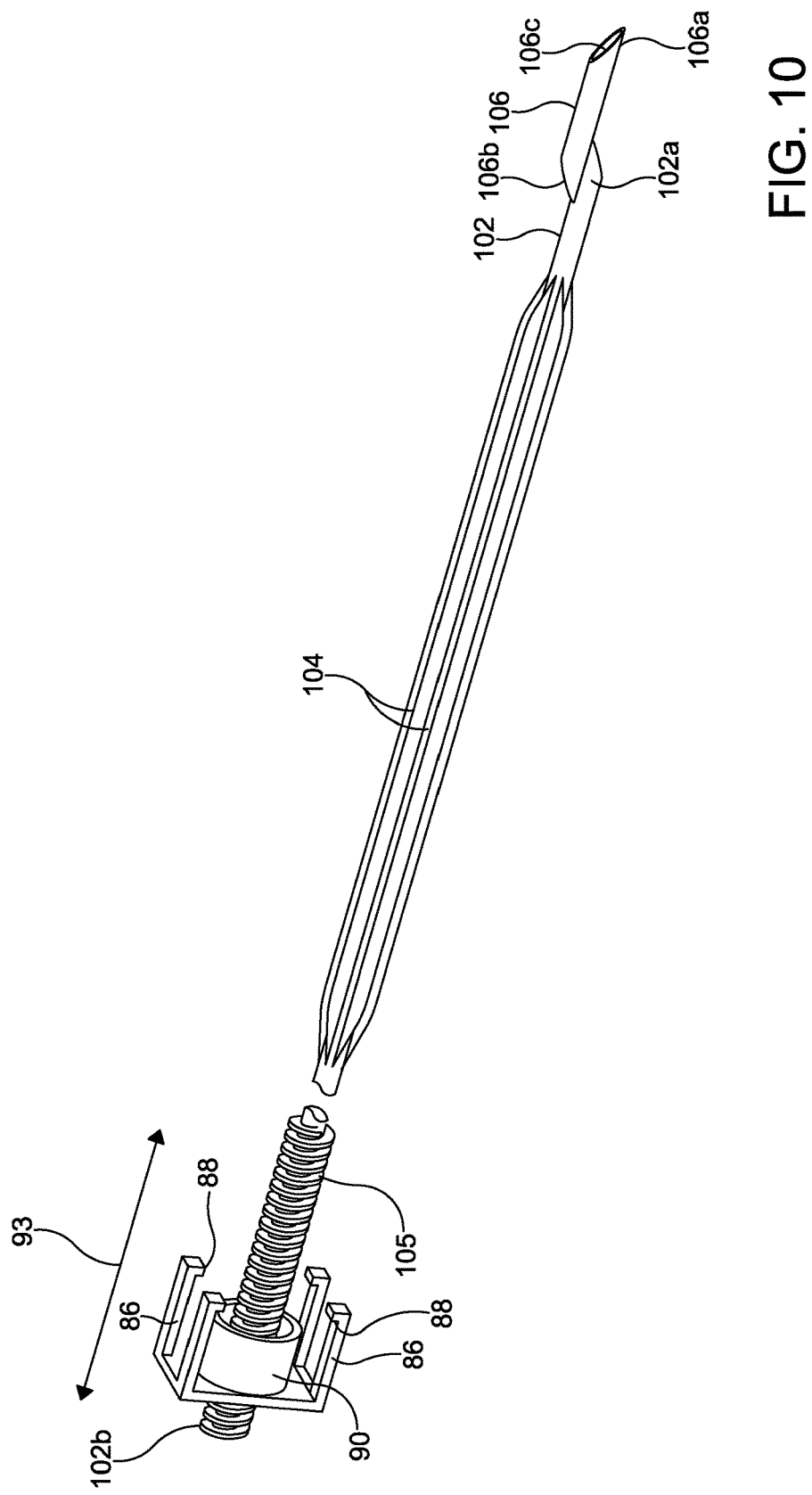
FIG. 10 is a plan view of a second embodiment of the intubation assembly rod illustrated in FIG. 8.

A second embodiment of the intubation assembly rod is shown at 102 in FIG. 10. The rod 102 is similar to the rod 72 and includes the plurality of longitudinally and radially outwardly extending ribs 104. The proximal end 102*b* of the rod 102 also includes threads 105 configured for connecting the rod 102 to the first connecting member 82, described above.

The distal end 102*a* of the rod 102 is tapered or substantially cone-shaped and defines a leading end of the rod 102, and includes a guide system configured as a guide sleeve 106 in lieu of the guide member portion 78 and the spherical tip 76 of the guide rail 75. The guide sleeve 106 includes a first or distal end 106*a*, a second or proximal end 106*b*, and has a longitudinally extending substantially cylindrical channel 106*c* formed therethrough. The illustrated guide sleeve 106 is mounted directly to the rod 102 and a bridge, such as the bridges 80 and 112, are not required, but may be provided if desired.

Figure 12:
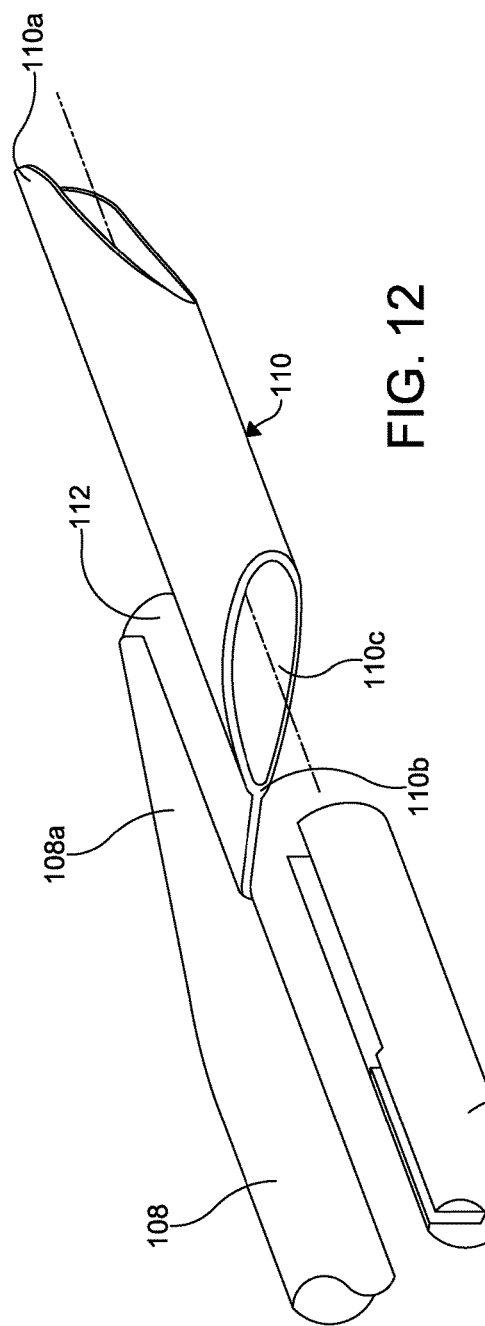
FIG. 12 is a perspective view of a third embodiment of the intubation assembly rod illustrated in FIG. 8.

In the illustrated embodiment, the distal and proximal ends 106*a* and 106*b* are tapered. The guide sleeve 106 is configured such that either the optical housing 50 or the flexible member 52, as best shown in FIG. 12, may be inserted through the channel 106*c* and that the guide sleeve 106 can be slidably mounted within the channel member 37. Advantageously, the tapered leading or distal end 106*a* of the guide sleeve 106 is also configured for easy and atraumatic advancement into the patient's airway; i.e., configured to avoid being caught on laryngeal structures as the guided introducer intubation assembly 38 and the leading edge or distal end 92*a* of the endotracheal tube 92 is advanced into the patient's airway, thus facilitating the delivery of the endotracheal tube 92 between the vocal cords and preventing trauma or injury to the vocal cords and other parts of the airway.

A third embodiment of the intubation assembly rod is shown at 108 in FIG. 12. The distal end 108*a* of the rod 108 is tapered or substantially cone-shaped and defines a leading end of the rod 108. The rod 108 includes a guide sleeve 110. The guide sleeve 110 includes a first or distal end 110*a*, a second or proximal end 110*b*, and has a longitudinally extending substantially cylindrical channel 110*c* formed therethrough. The guide sleeve 110 is attached to the rod 108 by a substantially flat bridge 112 that extends between the rod 108 and the guide sleeve 110. The rod 108 is otherwise substantially the same as the rod 102. Like the bridge 80, the bridge 112 may be located at any desired portion of the rod 108. The bridge 112 may have any width and length, and may be attached to the guide sleeve 110 at any point proximal to the distal end 110*a* of the guide sleeve 110. Further, the guide sleeve 110 may be attached to the rod 108 at any other longitudinal location or at any other desired distance from the distal end 108*a* of the rod 108. The guide sleeve 110 is configured such that the distal end 52*a* of the flexible member 52, as shown in FIG. 12, may be inserted through the channel 110*c*. The guide sleeve 110 is further configured for insertion through the channel 50*c* of the optical housing 50, the channel 37c of the channel member 37, and the channel 46c of the channel member 46. Like the bridge 80, the bridge 112 may have any desired thickness such that the bridge 112 may extend through the slot 50d of the channel 50c, the slot 37b of the channel 37c, and the slot 46d of the channel 46c.

Figure 12A:
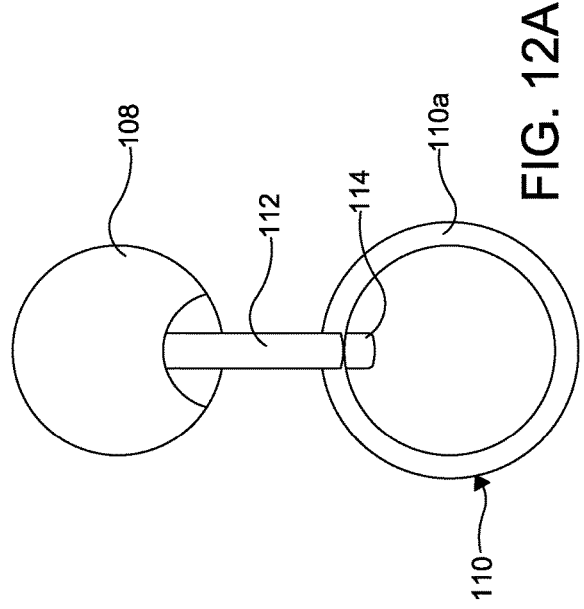
FIG. 12A is an end view of the third embodiment of the intubation assembly rod illustrated in FIG. 12.

FIG. 12A is an end view of the rod 108 and shows a radially inwardly extending stop member 114 formed at the distal end 110a of the guide sleeve 110. The stop member 114 may be provided to assist in retaining the flexible member 52 within the guide sleeve 110 during insertion of the endotracheal tube insertion device 30 into the patient's airway. Alternatively, the distal end 110a of the guide sleeve 110 may include two or more of the stop members 114. Although shown formed at the distal end 110a of the guide sleeve 110, the stop members 114 may be formed at the proximal end 110b of the guide sleeve 110, or at any location between the distal and proximal ends 110a and 110b. Additionally, the stop members 114 may have any desired shape and size.

Like the guide rail 75 and its component parts, the guide sleeve 110 and the bridge 112 may be formed from any flexible or semi-flexible material, such as silicon, rubber, wire-reinforced silicon, wire-reinforced rubber, and polymers.

Figure 13:
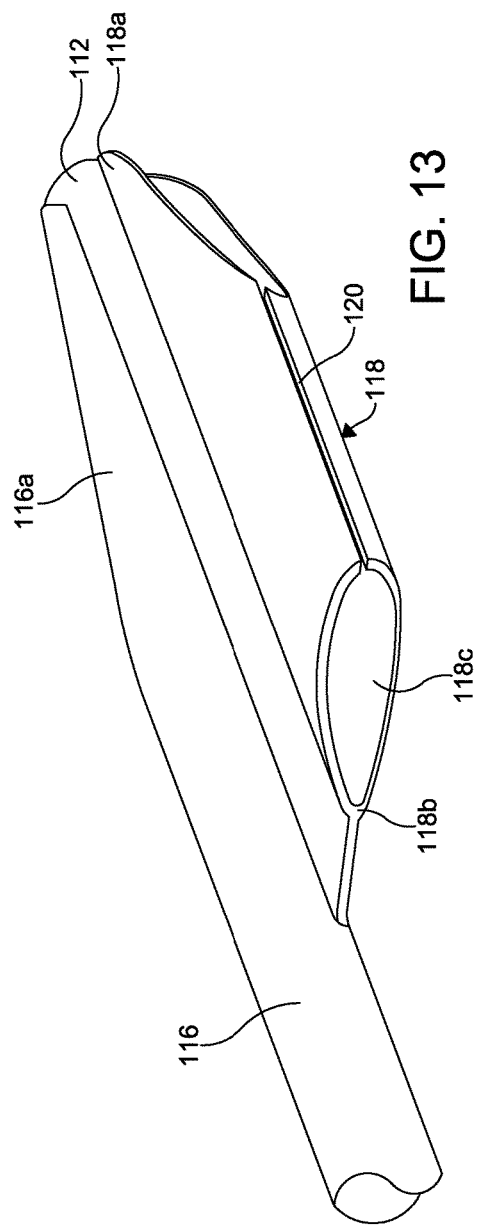
FIG. 13 is a perspective view of a fourth embodiment of the intubation assembly rod illustrated in FIG. 8.

A fourth embodiment of the intubation assembly rod is shown at 116 in FIG. 13. The distal end 116a of the rod 116 is tapered or substantially cone-shaped and defines a leading end of the rod 116. The rod 116 includes a guide sleeve 118. The guide sleeve 118 includes a first or distal end 118a, a second or proximal end 118b, and has a longitudinally extending substantially cylindrical channel 118c formed therethrough. The guide sleeve 118 is attached to the rod 116 by the substantially flat bridge 112 that extends between the rod 116 and the guide sleeve 118. The illustrated guide sleeve 118 also includes a longitudinally extending slot 120 formed therethrough. The rod 116 is otherwise substantially the same as the rod 102.

Figure 14:
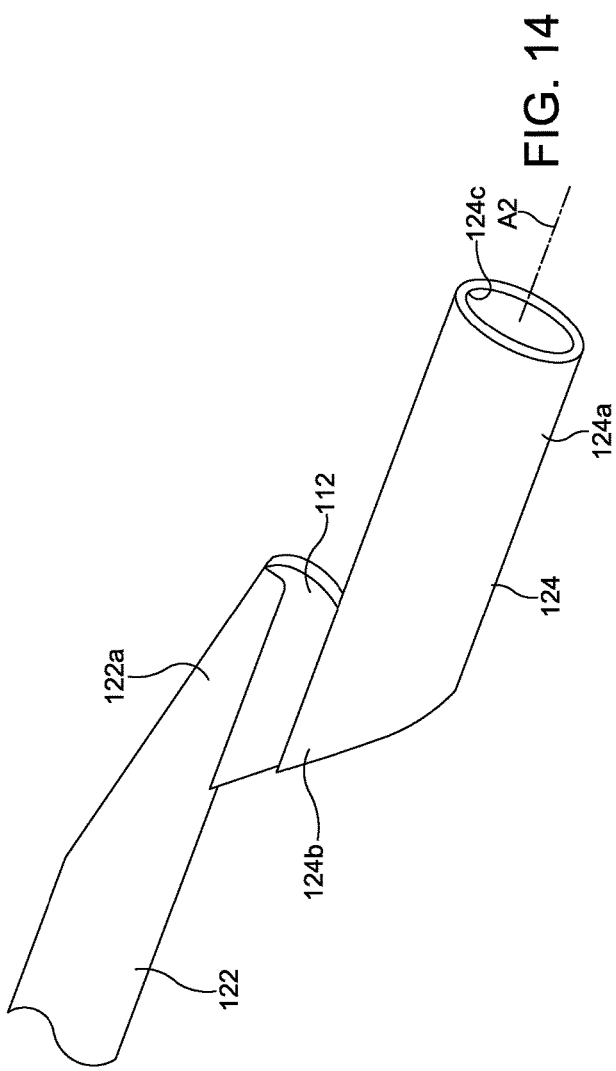
FIG. 14 is a perspective view of a fifth embodiment of the intubation assembly rod illustrated in FIG. 8.

A fifth embodiment of the intubation assembly rod is shown at 122 in FIG. 14. The distal end 122a of the rod 122 is tapered or substantially cone-shaped and defines a leading end of the rod 122. The rod 122 includes a guide sleeve 124. The guide sleeve 124 is similar to the guide sleeve 118 and includes a first or distal end 124a, a second or proximal end 124b, and has a longitudinally extending substantially cylindrical channel 124c formed therethrough. The guide sleeve 124 is attached to the rod 122 by the substantially flat bridge 112 that extends between the rod 122 and the guide sleeve 124. Unlike the guide sleeve 118, the distal end 124a of the guide sleeve 124 is not tapered. Rather, an end surface of the distal end 124a is substantially perpendicular to an axis A2 of the guide sleeve 124. The rod 122 is otherwise substantially the same as the rod 102.

Figure 14B:
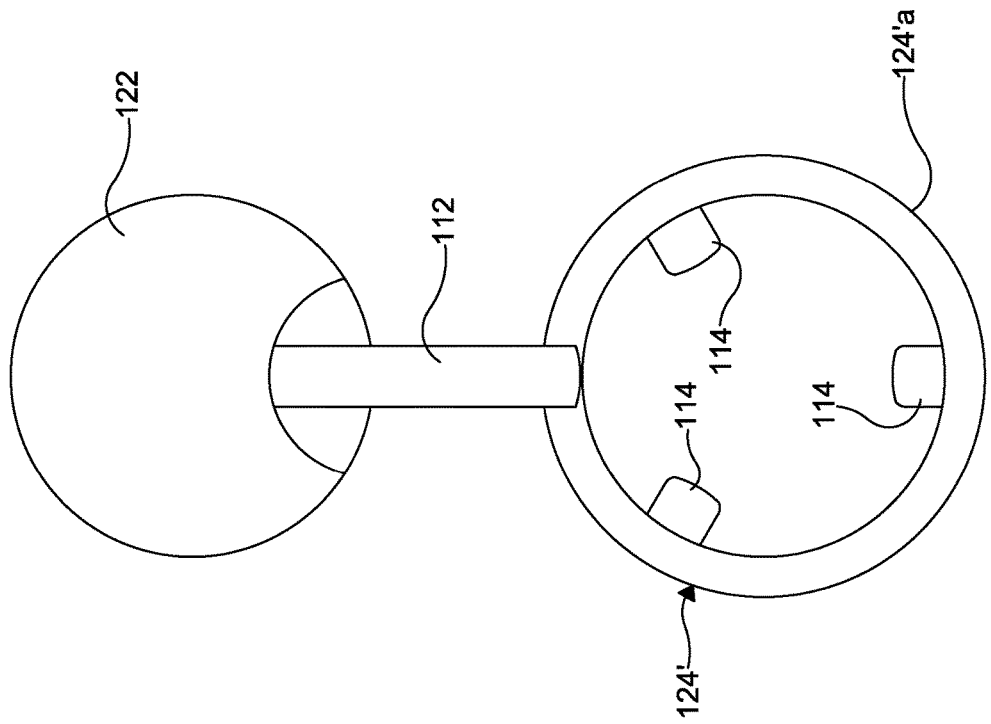
FIG. 14B is an end view of the fifth embodiment of the intubation assembly rod illustrated in FIG. 14 showing a second embodiment of the sleeve and a stop member.
Figure 14A:
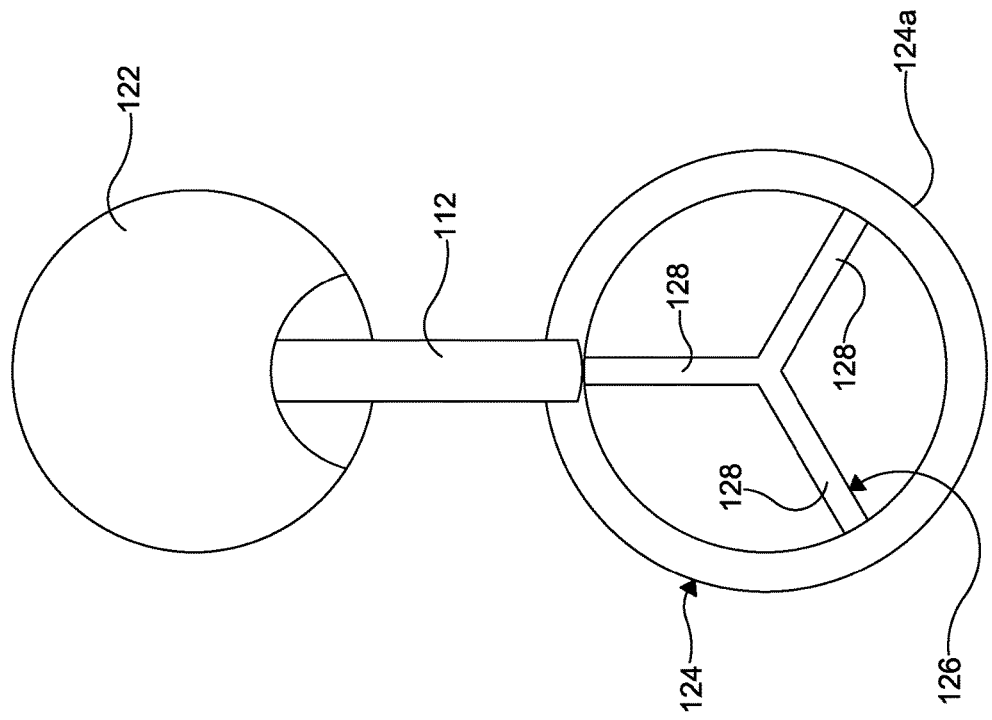
FIG. 14A is an end view of the fifth embodiment of the intubation assembly rod illustrated in FIG. 14 showing a first embodiment of the sleeve and a stop member.

FIG. 14A is an end view of the rod 122 and shows a first embodiment of a stop member 126 formed at the distal end 124a of the guide sleeve 124. The illustrated stop member 126 includes three radially inwardly extending legs 128. The stop member 126 may be provided to assist in retaining the flexible member 52 within the guide sleeve 124 during insertion of the endotracheal tube insertion device 30 into the patient's airway. Alternatively, the distal end 124a of the guide sleeve 124 may include any desired number of the legs 128, such as one, two, or more than three legs 128. Although shown formed at the distal end 124a of the guide sleeve 124, the stop member 126 may be formed at the proximal end 124b of the guide sleeve 124, or at any location between the distal and proximal ends 124a and 124b. Additionally, the legs 128 may have any desired shape and size.

FIG. 14B is an end view of the rod 122 and shows a second embodiment of the guide sleeve 124', wherein the distal end 124'a thereof includes three of the radially inwardly extending stop members 114. As described above, the stop members 114 may be provided to assist in retaining the flexible member 52 within the guide sleeve 124 during insertion of the endotracheal tube insertion device 30 into the patient's airway. Alternatively, the distal end 124'a of the guide sleeve 124' may include two of the stop members 114 or more than three of the stop members 114. Although shown formed at the distal end 124'a of the guide sleeve 124', the stop members 114 may be formed at the proximal end 124'b of the guide sleeve 124', or at any location between the distal and proximal ends 124'a and 124'b. Additionally, the stop members 114 may have any desired shape and size. If desired, an outside surface of the distal end 52a of the flexible member 52 may be formed with guide grooves (not shown) corresponding to the stop members 114. The flexible member 52 would therefore be slidably movable within the guide sleeve 124' and the stop members 114 would slidably engage the flexible member 52 within the grooves.

Figure 15:
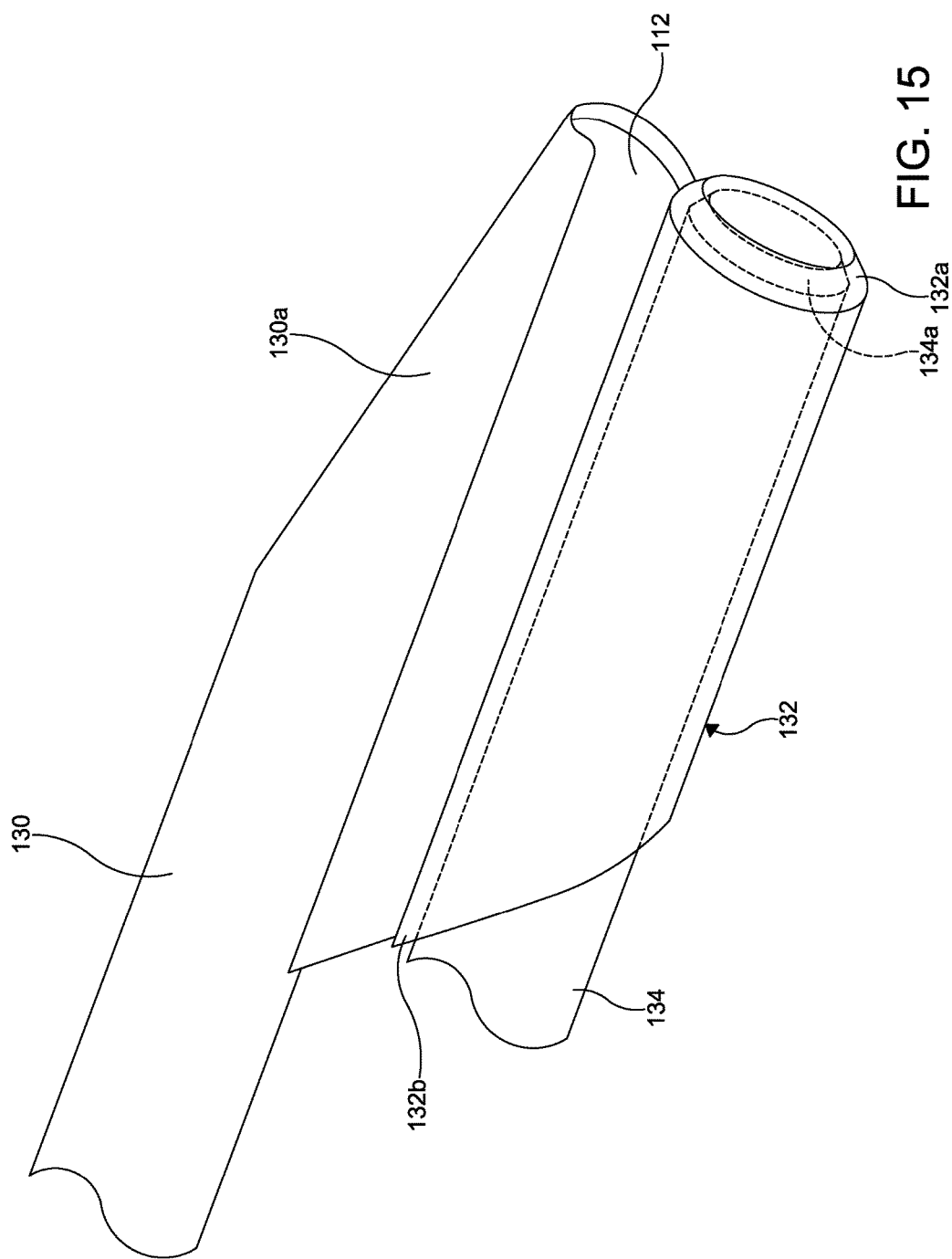
FIG. 15 is a plan view of a sixth embodiment of the intubation assembly rod illustrated in FIG. 8.

A sixth embodiment of the intubation assembly rod is shown at 130 in FIG. 15. The distal end 130a of the rod 130 is tapered or substantially cone-shaped and defines a leading end of the rod 130. The rod 130 includes a guide sleeve 132 having a first or distal end 132a, a second or proximal end 132b, and has a longitudinally extending substantially cylindrical channel 132c formed therethrough. The guide sleeve 132 is attached to the rod 130 by the substantially flat bridge 112 that extends between the rod 130 and the guide sleeve 132. The distal end 132a of the guide sleeve 132 has a frusto-conical shape. The guide sleeve 132 is configured to retain a second embodiment of the flexible member, a portion of which is shown at 134. A distal end 134a of the flexible member 134 also has a frusto-conical shape, such that the distal end 134a of the flexible member 134 is retained within the distal end 132a of the guide sleeve 132. Alternatively, the distal end 134a of the flexible member 134 may be rounded, tapered, or substantially cone-shaped and defines a leading end of the flexible member 134. Advantageously, the tapered leading or distal end 134a of the flexible member 134 is also configured for easy and atraumatic advancement into the patient's airway; i.e., configured to avoid being caught on laryngeal structures like the guided introducer intubation assembly 38 shown in FIG. 8, as the leading edge or distal end 92a of the endotracheal tube 92 is advanced into the patient's airway, thus facilitating the delivery of the endotracheal tube 92 between the vocal cords and preventing trauma or injury to the vocal cords and other parts of the airway. The rod 130 is otherwise substantially the same as the rod 102.

It will be understood that each embodiment of a rod and a guide sleeve described herein, including the rod 108 and the guide sleeve 110, the rod 116 and the guide sleeve 118, the rod 122 and the guide sleeve 124, and the rod 130 and the guide sleeve 132, may be formed without the substantially flat bridge 112. In such embodiments, the sleeves, 110, 118, 124, and 132 are mounted directly to the rods 108, 116, 122, and 130, respectively. The bridge 112 may have any width and length, and may be attached to the guide sleeves 110, 118, 124, and 132 at any point proximal to the distal ends of the guide sleeves 110, 118, 124, and 132, respectively.

Prior to use, the guided introducer intubation assembly 38 is secured to the optical assembly 36 by inserting the guide member portion 78 of the guide rail 75 into the intubation assembly guide channel 64 via the first portion 64a until the guide member portion 78 is seated within the second portion 64c of the intubation assembly guide channel 64, the tip 76 is seated within the first portion 64a of the intubation assembly guide channel 64, and the bridge 80 extends through the second portion 64b of the intubation assembly guide channel 64, as shown in FIGS. 2 and 19. The flexible member 52 of the optical assembly 36 may be locked or fixedly positioned relative to the optical housing 50 by manually moving the mounting post 68b of the control device 68 into one of the notches 48.

Alternatively, a mechanical or electro-mechanical movement device (not shown) may be attached to the flexible member 52, between the flexible member 52 and the optical housing 50, or between the flexible member 52 and any desired portion of the endotracheal tube insertion device 30, and configured to selectively move the flexible member 52 longitudinally within the optical housing 50.

Prior to being inserted into the patient's airway, the guided introducer intubation assembly 38 and attached endotracheal tube 92 may be releasably attached to the endotracheal tube insertion device 30 within the attachment member 70, as best shown in FIG. 2.

In use, one operator or user may insert the blade assembly 34, with the attached optical assembly 36 and guided introducer intubation assembly 38, into the airway of a patient, until the distal end 35a of the blade body 35 is at the epiglottis. The distal end 52a of the flexible member 52 may then be moved outward of a distal end of the channel member 37 to gain a view of the vocal cords. The mounting post 68b of the control device 68 is moved out of the notch 48 within which it has been positioned, and the distal end 52a of the flexible member 52 may be moved outwardly in increments, such as about 0.5 cm increments, up to a distance of about 7 cm. As described above, the distal end 52a of the flexible member 52 may be moved relative to its axis A1 to gain a better view of the vocal cords, and may be locked or retained in a position selected by the user.

The user may then remove the endotracheal tube 92 from within the attachment member 70. Subsequently, the user may slide the guided introducer intubation assembly 38 forwardly into the trachea and outwardly of the guide channel 64 until the tip 76 is about 12 cm below or beyond the vocal cords, and the balloon cuff 96 is below the vocal cords. The balloon cuff 96 may then be inflated in a conventional manner. The blade assembly 34 and the optical assembly 36 may be removed from the patient. The guided introducer intubation assembly 38 may then be disconnected from the endotracheal tube 92 and also removed from the patient.

Advantageously, the improved endotracheal tube insertion device 30 includes the guided introducer intubation assembly 38, the optical assembly 36, and the blade assembly 34, that are interconnected and function as a single unit during endotracheal tube 92 positioning.

As a further advantage, the improved endotracheal tube insertion device 30 is a relatively simple tool that allows a user to gain and maintain full control of a patient or accident victim's airway without the experience of one who has performed hundreds or thousands of endotracheal intubation procedures. Users, such as first responders, without such significant experience may use the improved endotracheal tube insertion device 30 to intubate the airway of a patient with or without the assistance of a physician airway specialist who may be viewing remotely, but in real-time, the video of the procedure.

Advantageously, video of the airway may be transmitted via the internet in real time to a specialist anywhere in the world. This allows the specialist to provide advice and guidance to a less experienced or less knowledgeable user, whether the user and patient are in a hospital or at a remote accident site.

Although not illustrated, the optical assembly 36 may be formed with a longitudinally extending rail, similar to the guide member portion 78, and the guided introducer intubation assembly 38 may be formed with a corresponding longitudinally extending slot or groove within which the rail may be slidably mounted. A stop member, including but not limited to a retaining ball, such as similar to the spherical tip 76, may be provided on either a distal or proximal end of the rail or the groove to prevent proximal or rearward movement of the guided introducer intubation assembly 38 along the rail.

Figure 16:
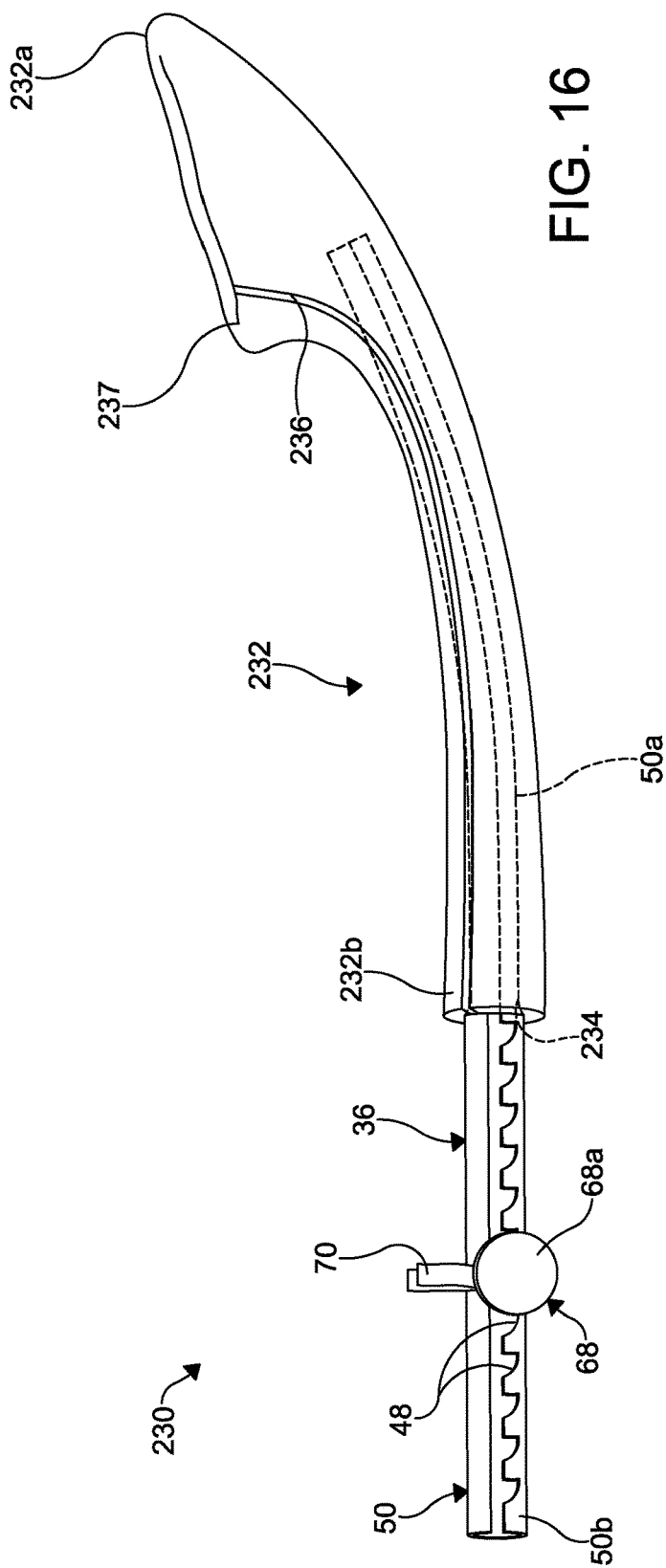
FIG. 16 is an elevational view of a portion of a second embodiment of a known endotracheal tube insertion device.
Figure 17:
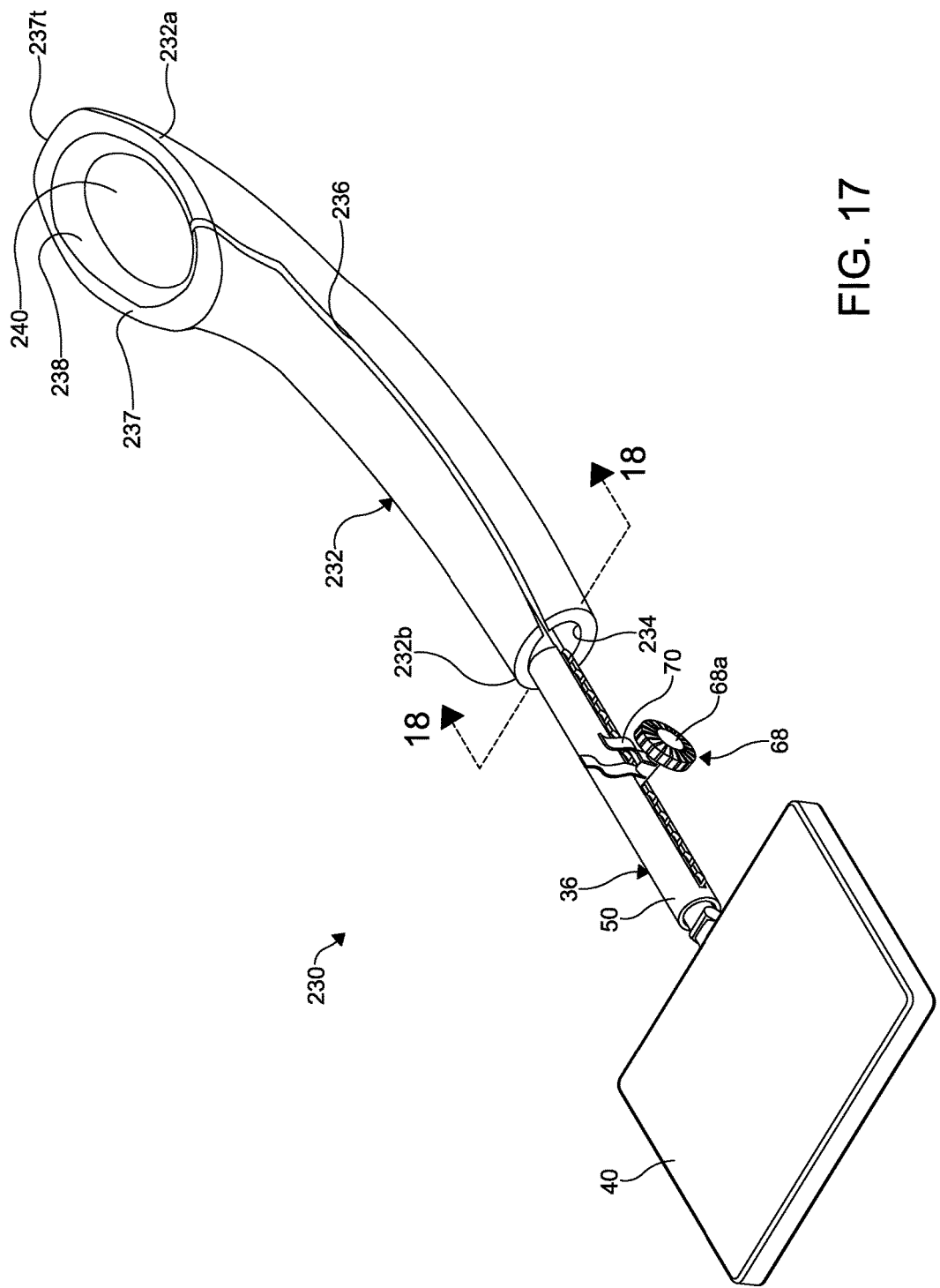
FIG. 17 is a perspective view of the second embodiment of the endotracheal tube insertion device illustrated in FIG. 16.

A second embodiment of the endotracheal tube insertion device is shown at 230 in FIGS. 16 through 18. In FIG. 16, the endotracheal tube insertion device 230 is shown with the guided introducer intubation assembly 38 and the video monitor 40 removed for clarity. The endotracheal tube insertion device 230 also includes the optical assembly 36, described above.

Unlike the improved endotracheal tube insertion device 30, the improved endotracheal tube insertion device 230 does not include the blade assembly 34. If desired, the endotracheal tube insertion device 230 may include the handle 32. As shown in FIG. 16, the improved endotracheal tube insertion device 230 includes an insertion member configured as a supraglottic member 232 in lieu of the blade 35. The supraglottic member 232 includes a first or distal end 232a, a second or proximal end 232b, has a longitudinally extending passageway 234 formed therethrough, and a longitudinally extending slot 236 formed through a wall thereof. The slot 236 may have any desired length and width. In addition to the generally straight shape of the slot 236 shown, the slot 236 may have any other desired shape, such as a generally serpentine or wavy pattern (not shown) to assist in retaining the guided introducer intubation assembly 38 within the passageway 234.

The slot 236 facilitates removal of the guided introducer intubation assembly 38, as described below. In the illustrated embodiment, the passageway 234 has a substantially oval cross-sectional shape, as best shown in FIG. 18, providing space for the illustrated optical assembly 36 and the guided introducer intubation assembly 38, not shown in FIGS. 16 through 18. In the illustrated embodiment, the optical housing 50 of the optical assembly 36 is attached or mounted within the passageway 234. It will be understood that the optical housing 50 may be integrally formed with the supraglottic member 232, or attached by any desired means included with adhesive, by welding, or in a snap-fit arrangement to ensure that the optical housing 50 does not move relative to the supraglottic member 232 during use.

The guided introducer intubation assembly 38 is described as extending into and through the passageway 234 as best shown in FIGS. 17 and 18. Alternatively however, the passageway 234 may be configured large enough to only allow the optical assembly 36 to fit therein. In such an embodiment, the guided introducer intubation assembly 38 may be attached to the flexible member 52, but routed outside of the supraglottic member 232.

In the illustrated embodiment, and as best shown in FIG. 18, the longitudinally extending slot 236 is formed at an angle B2 from a plane P1 that vertically bisects the supraglottic member 232 (when viewing the cross-sectional view of the supraglottic member 232 in FIG. 18). In the illustrated embodiment, the angle B2 is within the range of about 30 degrees to about 60 degrees from the plane P1. Alternatively, the angle B2 may be any angle from 0 degrees to 360 degrees from the plane P1.

The supraglottic member 232 includes a generally bowl-shaped supraglottic cuff 237 formed at the distal end 232a thereof. The supraglottic cuff 237 may be conventional in the art and includes a cuff wall 238 and a cuff opening 240 into which the optical assembly 36 and the guided introducer intubation assembly 38 (not shown in FIGS. 16 through 18) extend. The illustrated passageway 234 has a substantially oval cross-sectional shape, however the passageway 234 may have any desired cross-sectional shape, such as substantially circular, and substantially rectangular. Additionally, the passageway 234 may have any other desired diameter or cross-sectional size.

The supraglottic cuff 237 may be a non-inflatable cuff, such as the i-Gel® supraglottic airway manufactured by Intersurgical Ltd. The non-inflatable supraglottic cuff 237 may be formed of any gel-like or other substantially soft material designed to provide an anatomical, impression fit over the laryngeal inlet. Preferably, the shape, softness, and contours of the supraglottic cuff 237 accurately mirror the perilaryngeal anatomy. Alternatively, the supraglottic cuff 237, or any one or more portions thereof, may be inflatable and therefore include a conventional air inflation tube 242, such as shown in FIG. 18. The air inflation tube 242 may be attached to the supraglottic cuff 237 and configured for attachment to a source of air, such as a syringe. Although illustrated in one location, the air inflation tube 242 may be attached to the supraglottic cuff 237 at any desired location. It will be understood that the supraglottic cuff 237 may have any desired shape, including a shape configured to displace the epiglottis and laryngeal structures to optimize the user's view of the vocal cords. Advantageously, the inflatable supraglottic cuff 237 allows the user to more easily displace laryngeal structures such as the epiglottis.

In use, the improved endotracheal tube insertion device 230 differs from the improved endotracheal tube insertion device 30 in its position in the larynx for operation. For example, the improved endotracheal tube insertion device 230 is designed and configured to be inserted blindly into the mouth of a patient and advanced along the hard and soft palates until a distal tip cuff 237t of the supraglottic cuff 237 is seated in the hypopharynx with the cuff opening 240 facing the supraglottic structures. The flexible member 52 may then be advanced within the optical housing 50, carrying with it the guided introducer intubation assembly 38 in a manner similar to the method described above for use of the improved endotracheal tube insertion device 30 having the rigid blade body 35. Once the optical assembly 36 is optimally positioned and locked facing the vocal cords, the guided introducer intubation assembly 38 is advanced forward and off the optical assembly 36, as described above, such that the guided introducer intubation assembly 38 is positioned between the vocal cords and into the trachea.

The endotracheal tube 92 is positioned below the vocal cords and remains in the trachea. The flexible member 52, optical housing 50, and the supraglottic member 232 may then be removed together. Advantageously, the slot 236 in the supraglottic member 232 allows the supraglottic member 232, the flexible member 52, and the optical housing 50 to be removed from around the endotracheal tube 92, thus allowing the endotracheal tube 92 to remain in a desired position below the vocal cords. Finally, the guided introducer intubation assembly 38 may be removed from within the endotracheal tube 92.

Figure 20:
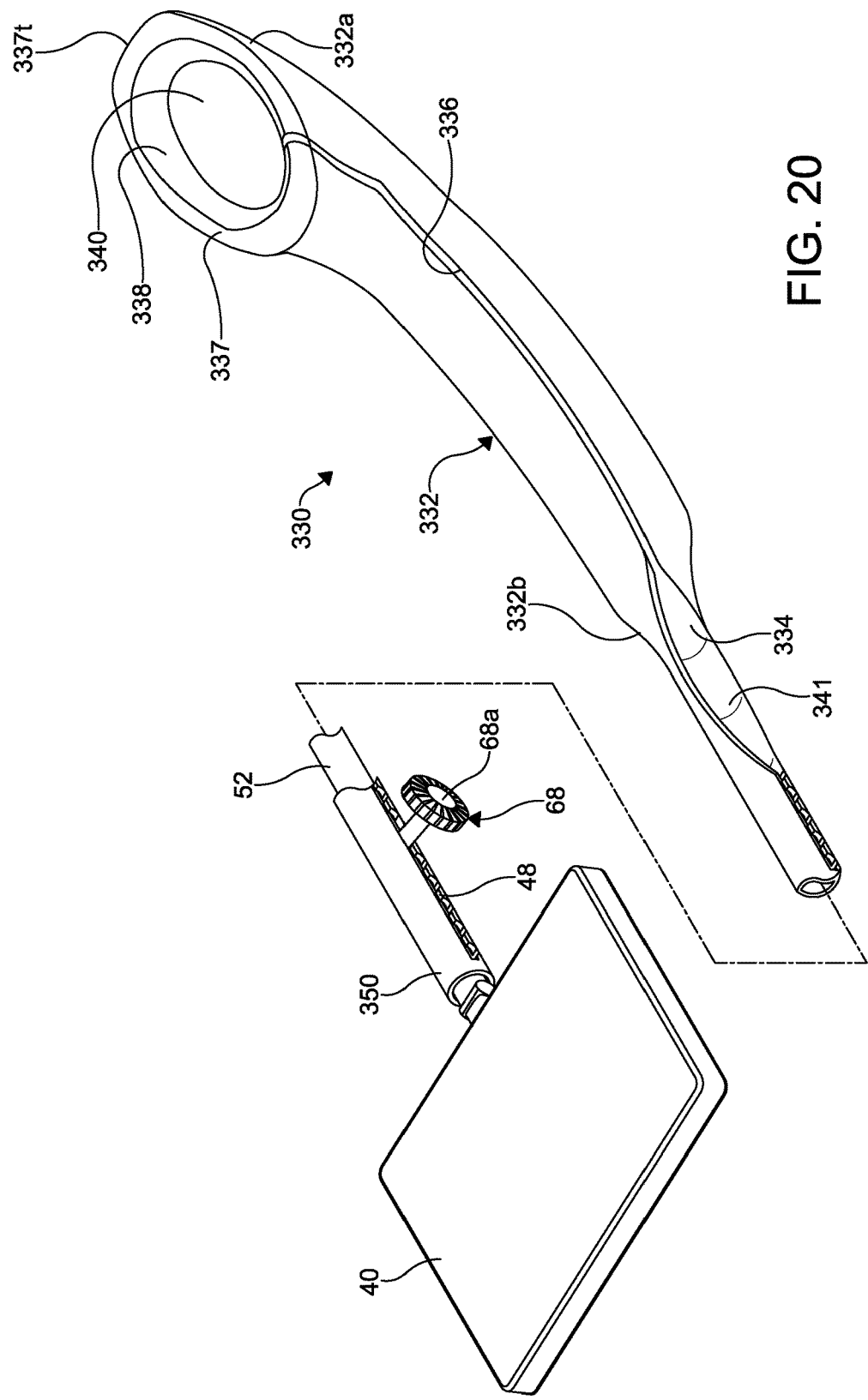
FIG. 20 is a perspective view of a third embodiment of a known endotracheal tube insertion device.
Figure 21:
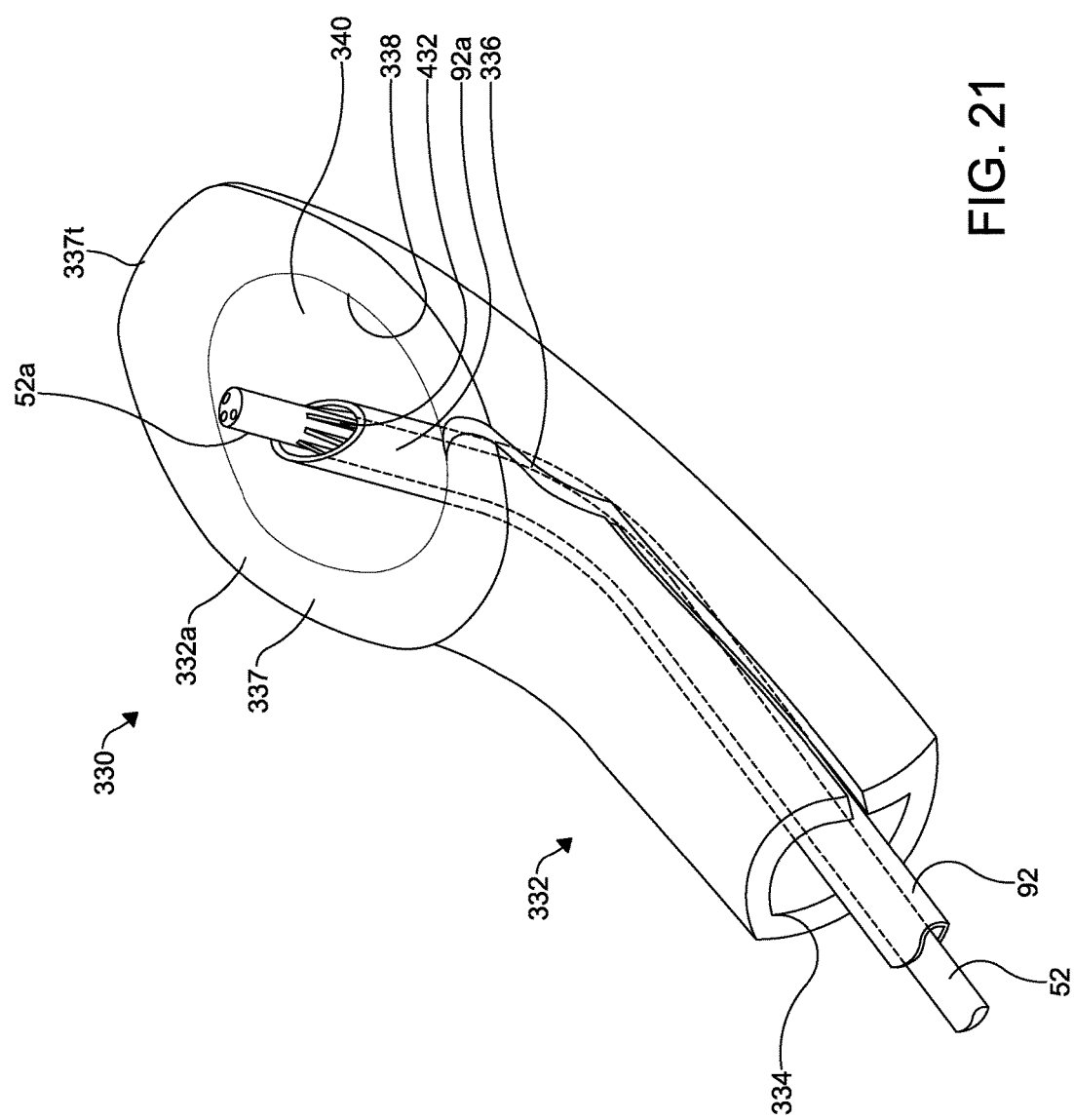
FIG. 21 is an enlarged perspective view of a portion of the third embodiment of the endotracheal tube insertion device illustrated in FIG. 20.

A third embodiment of the endotracheal tube insertion device is shown at 330 in FIGS. 20 and 21. The endotracheal tube insertion device 330 is similar to the endotracheal tube insertion device 230, includes the video monitor 40, and is configured to be used with the endotracheal tube 92 and the flexible member 52.

As shown in FIG. 20, the improved endotracheal tube insertion device 330 includes a supraglottic portion 332. The supraglottic portion 332 includes a first or distal end 332a, a second or proximal end 332b, has a longitudinally extending passageway 334 formed therethrough, and a longitudinally extending slot 336 formed through a wall thereof. Like the slot 236 described above, the slot 336 may have any desired length and width and may have any other desired shape, such as a generally serpentine or wavy pattern (not shown) to assist in retaining the endotracheal tube 92 within the passageway 334. The passageway 334 may have any desired shape, such as a substantially oval cross-sectional shape or a substantially cylindrical shape. It will be understood that the passageway 334 must be large enough to allow the endotracheal tube 92 to be inserted therein.

The supraglottic portion 332 includes a generally bowl-shaped supraglottic cuff 337 formed at the distal end 332a thereof. The supraglottic cuff 337 may be conventional in the art and includes a cuff wall 338 and a cuff opening 340 into which the concentrically arranged flexible member 52 and endotracheal tube 92 (best shown in FIG. 21) extend. Like the supraglottic cuff 237, the supraglottic portion 332 may include a non-inflatable supraglottic cuff 337, as described above. The supraglottic cuff 337, or any one or more portions thereof, may be inflatable, and thus may include the conventional air inflation tube 242 as shown in FIG. 18 and described above. The supraglottic cuff 337 may have any desired shape, including a shape configured to displace the epiglottis and laryngeal structures to optimize the user's view of the vocal cords. Advantageously, the inflatable supraglottic cuff 337 allows the user to more easily displace laryngeal structures such as the epiglottis.

An optical housing portion 350 extends outward of the proximal end 332b of the supraglottic portion 332. A large opening or sled area 341 is defined in the optical housing portion 350 adjacent the proximal end 332b of the supraglottic portion 332. The sled area 341 may be any desired size sufficient to allow the concentrically arranged flexible member 52 and endotracheal tube 92 to be inserted therein. The optical housing portion 350 may be attached to the supraglottic portion 332 by any desired means, such as with an adhesive, by a threaded connection, or by welding. Alternatively, the optical housing portion 350 may be integrally formed with the supraglottic portion 332, as shown in FIG. 20.

In the embodiment illustrated in FIG. 20, the flexible member 52 is inserted within the endotracheal tube 92. The endotracheal tube 92 with the flexible member 52 mounted therein is then inserted through the sled area 341 and into the passageway 334. The proximal end of the flexible member 52 may be secured within the optical housing portion 350 in the same manner that the flexible member 52 is secured within the second portion 50b of the optical housing 50, described above. The proximal end 92b of the endotracheal tube 92 and the attached connector 98 remain within the sled area 341, and may be releasably attached to the optical housing portion 350 or the flexible member 52.

As described above, the flexible member 52 and the concentrically mounted endotracheal tube 92 extend longitudinally through the passageway 334 of the supraglottic portion 332. In use, the endotracheal tube insertion device 330 may be inserted into the airway, and the flexible member 52 and the concentrically mounted endotracheal tube 92 may then be advanced below the vocal cords. Once the endotracheal tube 92 is positioned below the vocal cords, the flexible member 52 and the supraglottic portion 332 are removed. The flexible member 52 may be removed from the proximal end 92b of the endotracheal tube 92. The slot 336 in the supraglottic portion 332 allows the supraglottic portion 332 to be removed from around the endotracheal tube 92, thus allowing the endotracheal tube 92 to remain in a desired position below the vocal cords.

Referring to FIG. 21, the flexible member 52 and endotracheal tube 92 are shown within a portion of the supraglottic portion 332. As shown, the flexible member 52 and endotracheal tube 92 are concentrically arranged wherein the flexible member 52 is inserted within the endotracheal tube 92, and the endotracheal tube 92 is inserted into the passageway 334 as described above.

If desired, the distal end 52a of the flexible member 52 may have retention features such as ribs 432 having tapered leading edges similar to the ribs 74 on the rod 72, to retain the distal end 92a of the endotracheal tube 92 about the distal end 52a of the flexible member 52 during insertion into the airway. Alternatively, the distal end 52a of the flexible member 52 may have a frusto-conical shape, as shown in FIG. 15, thus also retaining the distal end 92a of the endotracheal tube 92 about the distal end 52a of the flexible member 52 during insertion into the airway. Additionally, the distal end 52a of the flexible member 52, in an area generally the same as the area in which the tapered leading edges of the ribs 432 shown in FIG. 21 are formed, may be configured to include a solid, an expandable, or a hollow inflatable portion, a leading edge of which may be formed with a tapered or substantially frusto-conical shaped transition segment where the ribs 432 would otherwise begin. Significantly, the ribs 432, particularly the shape and tapered leading edges of the ribs 432, or the alternative distal end 52a having the solid, expandable, or inflatable portion and the corresponding tapered or substantially frusto-conical shaped transition segment of the flexible member 52 of the improved endotracheal tube insertion device 330 are configured to prevent the leading edge or distal end 52a of the flexible member 52 from catching on laryngeal structures as the flexible member 52 and surrounding endotracheal tube 92 is advanced into the patient's airway, thus facilitating the delivery of the endotracheal tube 92 between the vocal cords and preventing trauma or injury to the vocal cords and other parts of the airway.

It will be understood that each of the improved endotracheal tube insertion devices 30, 230, and 330, illustrated and described herein, may be manufactured in any desired size. For example, the improved endotracheal tube insertion devices 30, 230, and 330 may be relatively small so as to be configured for use with pediatric patients, may be relatively large so as to be configured for use with adult patients.

FIG. 22 is a second embodiment of the flexible member 500. The flexible member 500 is similar to the flexible member 52 and is configured as an elongated member having an axis A3. The flexible member 500 includes a body 502 having a substantially cylindrical shape, a first or distal end 502a and a second or proximal end (not shown, but substantially the same as the proximal end 52b of the flexible member 52). Like the flexible member 52, the flexible member body 502 may alternatively have any other desired cross-sectional shape, such as substantially oval, substantially hexagonal, and substantially rectangular. The flexible member body 502 includes the video imaging device 60 and the light source 62 disposed in first and second longitudinally extending conduits, described above, and the third longitudinally extending conduit 58 configured as a suction tube.

The flexible member 500 also includes an intubation assembly rod receptor 504. The intubation assembly rod receptor 504 is configured as an elongated member having an axis A4, has a substantially cylindrical shape, and includes a first or distal end 504a. A proximal end 504b of the intubation assembly rod receptor 504 extends radially outwardly and longitudinally from the body 502 of the flexible member 500 such that the axis A4 is parallel to the axis A3 of the flexible member body 502. The intubation assembly rod receptor 504 has a length L2 within the range of about 1 cm to about 5 cm such that the distal end 504a of the intubation assembly rod receptor 504 is substantially coplanar with the distal end 502a of the flexible member body 502.

Alternatively, the intubation assembly rod receptor 504 may have any other desired cross-sectional shape, such as substantially oval, substantially hexagonal, and substantially rectangular. Further, the intubation assembly rod receptor 504 may have any desired length L2, such as a length from about 0.5 cm to about 10 cm.

FIG. 23 is a third embodiment of the flexible member 510. The flexible member 510 includes a body 512 having a substantially cylindrical shape, a first or distal end 512a, a second or proximal end (not shown, but substantially the same as the proximal end 52b of the flexible member 52), and the axis A3. Like the flexible member body 502, the flexible member body 512 may alternatively have any other desired cross-sectional shape, such as substantially oval, substantially hexagonal, and substantially rectangular. The flexible member body 512 includes the video imaging device 60 and the light source 62 disposed in first and second longitudinally extending conduits, described above, and the third longitudinally extending conduit 58 configured as a suction tube.

The flexible member 510 also includes an intubation assembly rod receptor 514. The intubation assembly rod receptor 514 is configured as an elongated member having the axis A4, has a substantially cylindrical shape, and includes a first or distal end 514a. A proximal end 514b of the intubation assembly rod receptor 514 has any desired length and extends radially outwardly and longitudinally from the body 512 of the flexible member 510 such that the axis A4 parallel to the axis A3 of the flexible member body 512. The distal end 514a of the intubation assembly rod receptor 514 extends beyond the distal end 512a of the body 512 a distance L3 within the range of about 0.5 cm to about 2.5 cm. Alternatively, the distal end 514a of the intubation assembly rod receptor 514 may extend beyond the distal end 512a of the body 512 any desired distance L3, such as a distance from about 0.1 cm to about 5 cm.

FIG. 24 is a fourth embodiment of the flexible member 520. The flexible member 520 includes a body 522 having a substantially cylindrical shape, a first or distal end 522a and a second or proximal end (not shown, but substantially the same as the proximal end 52b of the flexible member 52), and the axis A3. Like the flexible member body 502, the flexible member body 522 may alternatively have any other desired cross-sectional shape, such as substantially oval, substantially hexagonal, and substantially rectangular. The flexible member body 522 includes the video imaging device 60 and the light source 62 disposed in first and second longitudinally extending conduits, described above, and the third longitudinally extending conduit 58 configured as a suction tube.

The flexible member 520 also includes an intubation assembly rod receptor 524. The intubation assembly rod receptor 524 is configured as an elongated member having the axis A4, has a substantially cylindrical shape, any desired length, and includes a first or distal end 524*a*. A proximal end 524*b* of the intubation assembly rod receptor 524 extends radially outwardly and longitudinally from the body 522 of the flexible member 520 parallel to the axis A3 of the flexible member body 522. The distal end 524*a* of the intubation assembly rod receptor 524 does not extend all the way to the distal end 522*a* of the body 522, but is spaced apart from the distal end 522*a* of the body 522 a distance L4 within the range of about 0.5 cm to about 2.5 cm. Alternatively, the distal end 524*a* of the intubation assembly rod receptor 524 may be spaced apart from the distal end 522*a* of the body 522 any desired distance L4, such as a distance from about 0.1 cm to about 7 cm.

FIG. 25 is a fifth embodiment of the flexible member 530. The flexible member 530 is similar to the flexible member 52 and is configured as an elongated member having the axis A3. The flexible member 530 includes a body 532 having a substantially oval cross-sectional shape, a first or distal end 532*a* and a second or proximal end (not shown, but substantially the same as the proximal end 52*b* of the flexible member 52). Like the flexible member 52, the flexible member body 532 may alternatively have any other desired cross-sectional shape, such as substantially hexagonal, substantially rectangular, and substantially circular. The flexible member body 532 includes the video imaging device 60 and the light source 62 disposed in first and second longitudinally extending conduits, described above, and the third longitudinally extending conduit 58 configured as a suction tube.

The flexible member 530 also includes an intubation assembly rod receptor 534. The intubation assembly rod receptor 534 is configured as an elongated member having the axis A4, has a substantially oval cross-sectional shape, and includes a first or distal end 534*a*. The intubation assembly rod receptor 534 extends radially outwardly and longitudinally from the body 532 of the flexible member 500 parallel to the axis A3 of the flexible member body 532. The intubation assembly rod receptor 534 is spaced apart from the body 532 by an arcuate slot or groove 536. The intubation assembly rod receptor 534 may have any desired length, such as the length L2 (see FIG. 22), and may be configured such that the distal end 534*a* of the intubation assembly rod receptor 534 is substantially coplanar with the distal end 532*a* of the flexible member body 532. Alternatively, the distal end 534*a* may extend beyond the distal end 532*a* of the body 532, such as the length L3 (see FIG. 23), or may be spaced apart from the distal end 532*a*, such as the distance L4 (see FIG. 24), such that the distal end 534*a* of the receptor 534 does not extend all the way to the distal end 532*a* of the body 532. Additionally, the intubation assembly rod receptor 534 may have any other desired cross-sectional shape, such as substantially hexagonal and substantially rectangular, and may also be substantially cylindrical.

FIG. 26 is a sixth embodiment of the flexible member 540. The flexible member 540 is similar to the flexible member 52 and is configured as an elongated member having the axis A3. The flexible member 540 includes a body 542 having a substantially cylindrical shape, a first or distal end 542*a* and a second or proximal end (not shown, but substantially the same as the proximal end 52*b* of the flexible member 52). Like the flexible member body 532, the flexible member body 542 may alternatively have any other desired cross-sectional shape, such as substantially oval, substantially hexagonal, and substantially rectangular. The flexible member body 542 includes the video imaging device 60 and the light source 62 disposed in first and second longitudinally extending conduits, described above, and the third longitudinally extending conduit 58 configured as a suction tube.

The flexible member 540 also includes an intubation assembly rod receptor 544. The intubation assembly rod receptor 544 is configured as an elongated member having an axis A5, and includes a first or distal end 544*a*. The intubation assembly rod receptor 544 is formed from the body 542 and is separated therefrom by an arcuate slot or groove 546. The distal end 544*a* of the intubation assembly rod receptor 544 does not extend all the way to the distal end 542*a* of the body 542, but is spaced apart from the distal end 542*a* of the body 542 a distance L5 within the range of about 1 cm to about 2.5 cm. Alternatively, the distal end 544*a* of the intubation assembly rod receptor 544 may be spaced apart from the distal end 542*a* of the body 542 any desired distance L5, such as a distance from about 0.5 cm to about 5 cm.

It will be understood that the illustrated intubation assembly rod receptors, such as the receptors 504, 514, 524, 534, and 544 may be formed at any desired location on the distal ends of the flexible members 500, 510, 520, 530, and 540, and are not limited to the locations illustrated in the Figures.

It will be also understood that the distal ends 504*a*, 514*a*, 524*a*, 534*a*, and 544*a* of the receptors 504, 514, 524, 534, and 544, respectively, may be formed from, or reinforced with, a substantially rigid material, such as a rigid or semi-rigid polymer, metal, composite, or like material, to provide improved rigidity during use.

FIG. 27 is a seventh embodiment of the intubation assembly rod 550 of the guided introducer intubation assembly 38. The intubation assembly rod 550 is similar to the intubation assembly rod 102 shown in FIG. 10, and may include the plurality of longitudinally and radially outwardly extending ribs 104. Although not shown in FIG. 27, a proximal end of the intubation assembly rod 550 may also include the threads 105 configured for connecting the intubation assembly rod 550 to the first connecting member 82, described above.

It will be understood that each embodiment of the intubation assembly rod described herein may have features other than the ribs 74 and 104. For example, in lieu of the ribs 74 and 104, the ribbed portion of the intubation assembly rods, including the intubation assembly rod 550 and each embodiment of the intubation assembly rod described herein, may be configured to include a solid, an expandable, or a hollow inflatable portion, a leading edge of which may be formed with a tapered or substantially frusto-conical shaped transition segment where the ribs 74 or 104 would otherwise begin. This solid, expandable, or inflatable portion of the intubation assembly rod 550 may have, or may be inflated to have a desired outside diameter corresponding to inside diameter of an endotracheal tube 92. The ribs 74 and 104, and the structures providing an alternative to the ribs 74 and 104, i.e., the solid, expandable, or inflatable portion and the corresponding tapered or substantially frusto-conical shaped transition segment, are configured to avoid being caught on laryngeal structures as the guided introducer intubation assembly 38 and the leading edge or distal end 92a of the endotracheal tube 92 is advanced into the patient's airway, thus facilitating the delivery of the endotracheal tube 92 between the vocal cords and preventing trauma or injury to the vocal cords and other parts of the airway.

A distal end 550a of the rod 550 may be rounded, as illustrated, or tapered, and defines a leading end of the rod 550. The distal end 550a of the rod 550 may also include a guide system configured as a guide sleeve 552. The guide sleeve 552 includes an open first or distal end 552a, an open second or proximal end 552b, and has a longitudinally extending substantially cylindrical channel 552c formed therethrough and defining an axis A6. The illustrated guide sleeve 552 is configured such that the receptors 504, 514, 524, 534, and 544 may be inserted into the channel 552c.

FIG. 28 is an eighth embodiment of the intubation assembly rod 560 of the guided introducer intubation assembly 38. The intubation assembly rod 560 is similar to the intubation assembly rod 550 and may include the longitudinally and radially outwardly extending ribs 104, described above. Although not shown in FIG. 28, the intubation assembly rod 560 may also include the threads 105 configured for connecting the rod 560 to the first connecting member 82, described above.

A distal end 560a of the rod 560 may also include a guide system configured as a guide sleeve 562. The guide sleeve 562 includes a closed first or distal end 562a and an open second or proximal end 562b. A longitudinally extending substantially cylindrical channel 562c is formed through the guide sleeve 562 from the closed distal end 562a to the open proximal end 562b, and defining the axis A6. The illustrated guide sleeve 562 is configured such that the receptors 504, 514, 524, 534, and 54 may be inserted into the channel 562c. The distal end 562a of the guide sleeve 562 may be rounded, as illustrated, or tapered, and defines a leading end of the rod 560.

FIG. 29 is a ninth embodiment of the intubation assembly rod 570 of the guided introducer intubation assembly 38. The intubation assembly rod 570 is similar to the intubation assembly rod 560 and may include the longitudinally and radially outwardly extending ribs 104, described above. Although not shown in FIG. 28, the intubation assembly rod 570 may also include the threads 105 configured for connecting the intubation assembly rod 570 to the first connecting member 82, described above.

A distal end 570a of the rod 570 may also include a guide system comprising a first guide sleeve 572 and a second guide sleeve 574. The first guide sleeve 572 includes a closed first or distal end 572a, and an open second or proximal end 572b formed in the rod 570. A longitudinally extending substantially cylindrical channel 572c is formed through the first guide sleeve 572 from the closed distal end 572a to the open proximal end 572b, and defines the axis A6.

The second guide sleeve 574 is includes an open first or distal end 574a, and an open second or proximal end 574b. A longitudinally extending substantially cylindrical channel 574c is formed through the second guide sleeve 574 from the open distal end 574a to the open proximal end 574b, and defines an axis A7.

The illustrated first guide sleeve 572 is configured such that the receptors 504, 514, 524, 534, and 544 may be inserted into the channel 572c. A distal end 572a of the first guide sleeve 572 may be rounded, as illustrated, or tapered, and defines a leading end of the rod 570. Similarly, the second guide sleeve 574 is configured such that the distal ends 502a, 512a, 522a, 532a, and 542a of the flexible member bodies 502, 512, 522, 532, and 542, respectively, may be inserted into the channel 574c. If desired, the distal end 572a of the first guide sleeve 572 may be open.

Figure 30B:
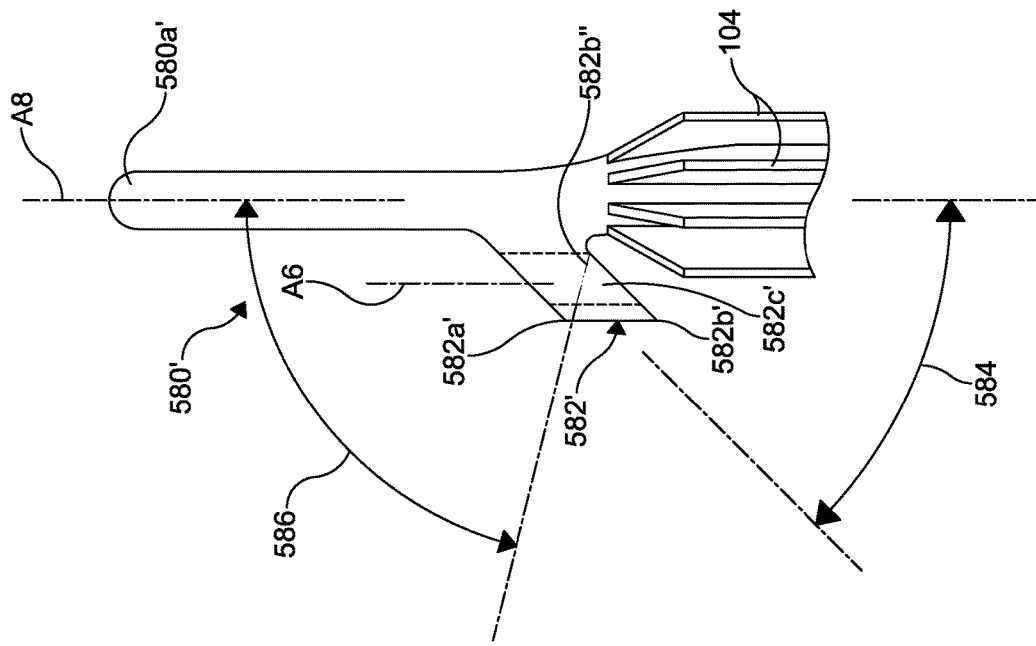
FIG. 30B is a perspective view of a portion of an eleventh embodiment of the intubation assembly rod illustrated in FIGS. 8 and 30A.
Figure 30A:
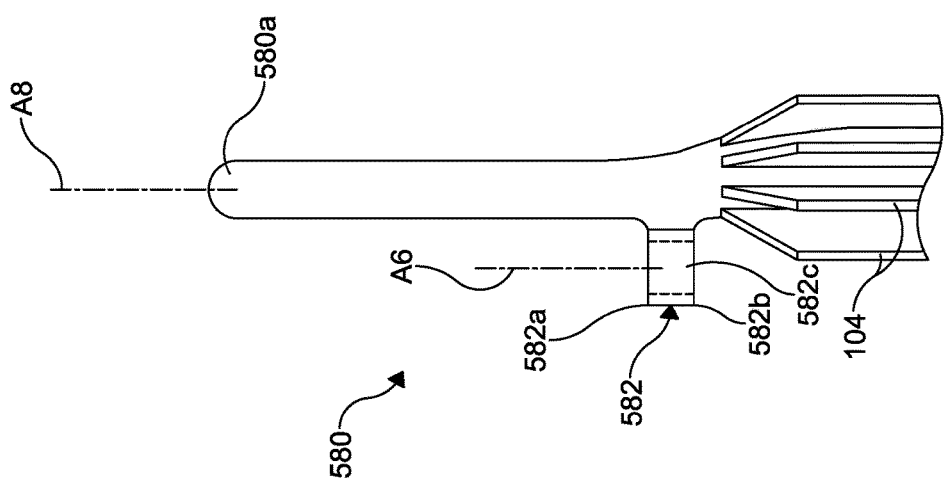
FIG. 30A is a perspective view of a portion of a tenth embodiment of the intubation assembly rod illustrated in FIG. 8.

FIG. 30A is a tenth embodiment of the intubation assembly rod 580 of the guided introducer intubation assembly 38. The intubation assembly rod 580 is similar to the intubation assembly rod 550, described above, has a distal end 580a, and defines an axis A8. The intubation assembly rod 580 may include the longitudinally and radially outwardly extending ribs 104, described above, and may also include the threads 105 configured for connecting the rod 580 to the first connecting member 82. The distal end 580a of the intubation assembly rod 580 may be rounded, as illustrated, or tapered, and defines a leading end of the intubation assembly rod 580.

The intubation assembly rod 580 may also include a guide system comprising a guide sleeve or guide ring 582. The guide ring 582 includes an open first or distal end 582a and an open second or proximal end 582b. A longitudinally extending substantially cylindrical channel 582c is formed through the guide ring 582 from the distal end 582a to the proximal end 582b thereof and defines the axis A6. If desired, one or more guide rings 582 may be formed on the intubation assembly rod 580.

The illustrated guide ring 582 is configured such that the receptors 504, 514, 524, 534, and 544 may be inserted into the channel 582c. Alternatively, the guide ring 582 may be configured such that the distal ends 502a, 512a, 522a, 532a, and 542a of the flexible member bodies 502, 512, 522, 532, and 542, respectively, may be inserted into and through the channel 582c.

FIG. 30B is an eleventh embodiment of the intubation assembly rod 580' of the guided introducer intubation assembly 38. The intubation assembly rod 580' is similar to the intubation assembly rod 580, described above, has a distal end 580a', and defines the axis A8. Like the intubation assembly rod 580, the intubation assembly rod 580' may include the longitudinally and radially outwardly extending ribs 104, described above, and may also include the threads 105 configured for connecting the rod 580' to the first connecting member 82, described above. The distal end 580a' of the intubation assembly rod 580' may be rounded, as illustrated, or tapered, and defines a leading end of the intubation assembly rod 580'.

The intubation assembly rod 580' may also include a guide system comprising a guide sleeve or guide ring 582'. The guide ring 582' includes an open first or distal end 582a' and an open second or proximal end 582b'. A longitudinally extending substantially cylindrical channel 582c' is formed through the guide ring 582' from the distal end 582a' to the proximal end 582b' thereof and defines the axis A6. If desired, one or more guide rings 582' may be formed on the intubation assembly rod 580'.

The guide ring 582' differs from the guide ring 582 in that the distal end 582a' of the guide ring 582', which defines a leading edge during insertion of the intubation assembly rod 580', may be formed at an angle 584 relative to the axis A6. In the illustrated embodiment, the angle 584 is about 45 degrees. Alternatively, the distal end 582a' of the guide ring 582' may be formed at any desired angle 584 relative to the axis A6, such as an angle between about 35 degrees and about 65 degrees. Additionally, the proximal end 582b' of the guide ring 582' may be formed at an angle substantially parallel to the distal end 582a'. Alternatively, the proximal end, as shown by the phantom line 582b", may also be formed at an angle 586 relative to the axis A8. For example, the angle 586 may be any desired angle 584 relative to the axis A8, such as an angle between about 35 degrees and about 65 degrees. It will be understood that the proximal ends 582b' and 582b" define a leading edge during removal of the intubation assembly rod 580'.

The guide ring 582' is configured such that the receptors 504, 514, 524, 534, and 544 may be inserted into the channel 582c'. Alternatively, the guide ring 582' may be configured such that the distal ends 502a, 512a, 522a, 532a, and 542a of the flexible member bodies 502, 512, 522, 532, and 542, respectively, may be inserted into and through the channel 582c'.

Alternatively, the distal ends 550a, 560a, 570a, 580a, and 580a', of the rods 550, 560, 570, 580, and 580' may be formed as a sphere or ball, such as shown at 564 in FIGS. 36 and 37. As shown in FIGS. 36 and 37, the intubation assembly rod 560' is substantially similar to the intubation assembly rod 560, includes the guide sleeve 562', the longitudinally extending substantially cylindrical channel 562c' formed through the guide sleeve 562' from the closed distal end 562a' to the open proximal end 562b'. The distal end of the intubation assembly rod 560' is configured as the ball 564.

Alternatively, the distal ends of the embodiments of the intubation assembly rods illustrated and described herein may be curved. For example, FIG. 38 shows a twelfth embodiment of the intubation assembly rod 630 having a curved distal end 630a. The rod 630 is otherwise similar to the intubation assembly rod 72 described above, and may include the plurality of longitudinally and radially outwardly extending ribs 74. A proximal end (not shown) of the intubation assembly rod 630 may also include the threads 73 configured for connecting the intubation assembly rod 630 to the first connecting member 82, described above.

As shown in FIG. 38, the distal end 630a of the intubation assembly rod 630 terminates in a spherical shaped tip 634, and defines a leading end of the intubation assembly rod 630. Alternatively, the distal end 630a of the intubation assembly rod 630 may be rounded or tapered.

Similarly, FIG. 39 shows a thirteenth embodiment of the intubation assembly rod 640 having a curved distal end 640a. The intubation assembly rod 640 is similar to the rod 560 described above, and may include the plurality of longitudinally and radially outwardly extending ribs 74. A proximal end (not shown) of the intubation assembly rod 630 may also include the threads 73 configured for connecting the intubation assembly rod 630 to the first connecting member 82, described above.

The distal end 640a of the intubation assembly rod 640 may also include a guide system configured as a guide sleeve 642. The guide sleeve 642 includes an open first or distal end 642a, an open second or proximal end 642b, and has an elongated channel 642c formed therethrough. The illustrated guide sleeve 642 is configured such that the receptors 504, 514, 524, 534, and 544 may be inserted into the channel 642c.

FIG. 40 also shows a fourteenth embodiment of the intubation assembly rod 650 having a curved distal end portion. The intubation assembly rod 650 is similar to the intubation assembly rod 640 described above, but includes a guide sleeve 652 having a closed distal end 652a. The intubation assembly rod 650 may include the plurality of longitudinally and radially outwardly extending ribs 74. A proximal end (not shown) of the intubation assembly rod 630 may also include the threads 73 configured for connecting the intubation assembly rod 630 to the first connecting member 82, described above.

As shown in FIG. 40, a distal end 650a of the intubation assembly rod 650 includes a guide system configured as the guide sleeve 652. The guide sleeve 652 includes the closed first or distal end 652a, an open second or proximal end 652b, and has an elongated channel 652c formed therethrough. The illustrated guide sleeve 652 is configured such that the receptors 504, 514, 524, 534, and 544 may be inserted into the channel 652c.

It will be understood that the entire length of any of the embodiments of the intubation assembly rods illustrated and described herein may be curved. Alternatively, any desired portion of the embodiments of the intubation assembly rods illustrated and described herein may be curved, such as the distal ends thereof, as shown in FIGS. 38 through 40. Advantageously, intubation assembly rods having curved distal ends minimize the possibility of the intubation assembly rod distal end from being caught or otherwise hung-up on an anterior wall of the trachea or on other laryngeal structures such as the arytenoids when advancing the intubation assembly, such as the guided introducer intubation assembly 38, into the trachea.

As described above, the intubation assembly rods and their component parts; i.e., the guide systems formed thereon, may be formed from any flexible or semi-flexible material, such as silicon, rubber, wire-reinforced silicon, wire-reinforced rubber, and polymers. Accordingly, in a free state; i.e., prior to insertion into the endotracheal tube 92, the intubation assembly rods may have a curved shape. In addition to providing rods with advantageous flexibility when inserted into a patient's airway, the flexibility of the intubation assembly rods also provides greater control for the user when inserting the rods into the endotracheal tube 92.

Figure 32:
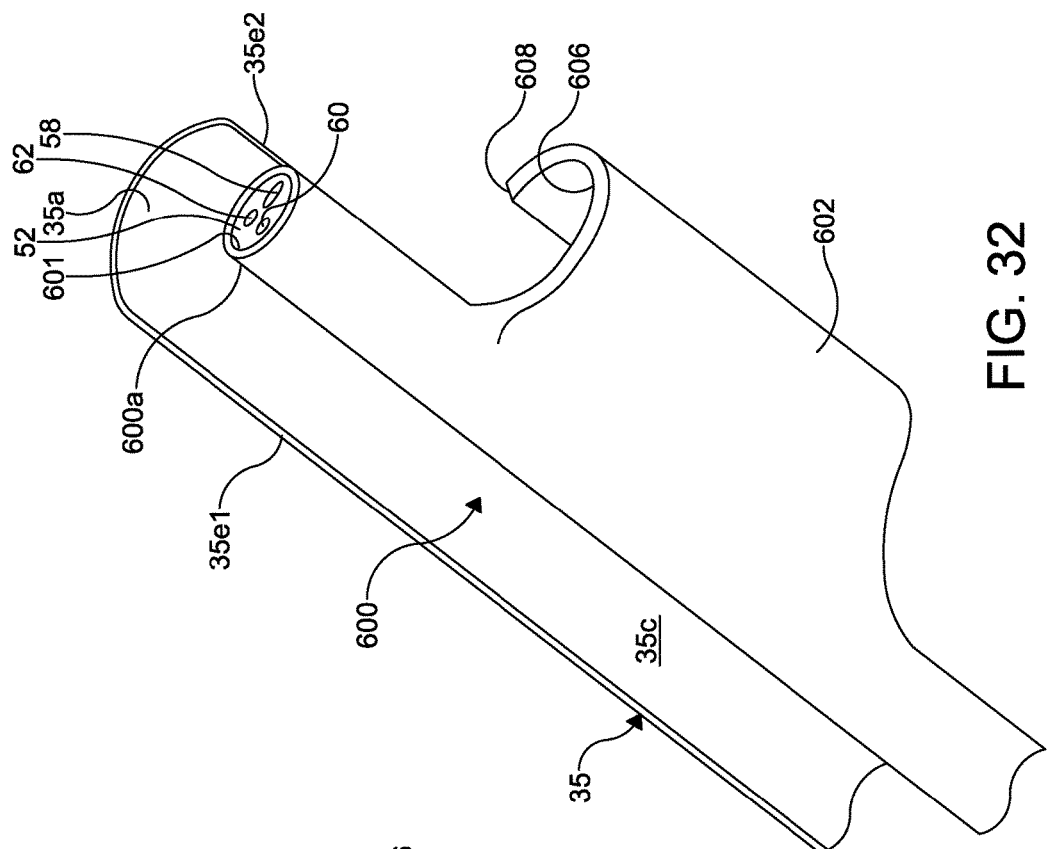
FIG. 32 is a perspective view of the second embodiment of the channel member illustrated in FIG. 31.
Figure 31:
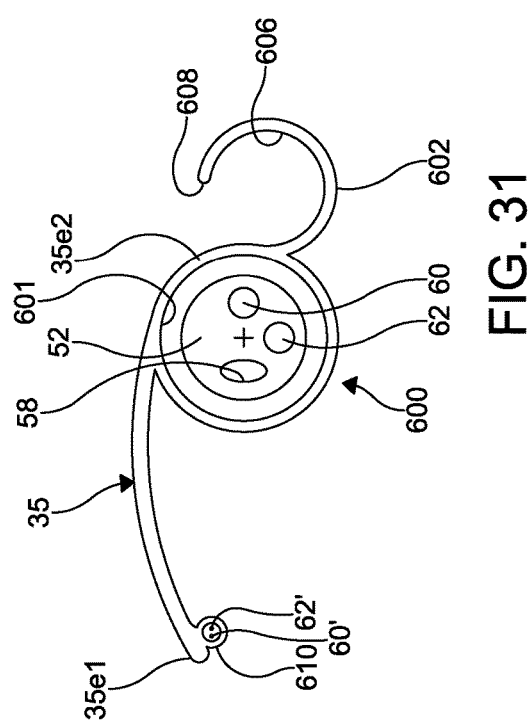
FIG. 31 is an end view of a second embodiment of the channel member illustrated in FIG. 2.

FIGS. 31 and 32 illustrate a second embodiment of the channel member 600 configured for attachment to the blade body 35 and further configured to receive and retain the flexible member 52 of the optical assembly 36, as shown in FIGS. 2 through 4.

As described above and also shown in FIGS. 3 and 4, the blade body 35 is substantially straight in the longitudinal direction and has an arcuate cross-sectional shape. Alternatively, the blade body 35, and each embodiment of the blade body described herein, may be formed with the curved blade body 44, described in detail above and shown in FIG. 11.

The channel member 600 includes a first or distal end 600a, a second or proximal end (not shown), defines a longitudinally extending channel 601, and is attached to the first side 35c (lower side when viewing FIG. 31) of the blade body 35. The illustrated channel member 600 has substantially circular cross-sectional shape. Alternatively, the channel member 600 may have any desired cross-sectional shape, such as substantially oval, substantially rectangular, or other geometric shape.

As shown in FIGS. 31 and 32, the channel member 600 is positioned near the second edge 35e2 of the blade body 35 (the right edge when viewing FIG. 31). Alternatively, the channel member 600 may be positioned near the first edge 35e1 of the blade body 35 (the left edge when viewing FIG. 31), or at any position intermediate the first edge 35e1 and the second edge 35e2.

The channel member 600 may include one or more endotracheal tube retention tabs 602 that extend outwardly from the channel member 600. The endotracheal tube retention tab 602 is configured to allow an endotracheal tube, such as the endotracheal tube 92, to be temporarily positioned and retained thereon or therein.

The retention tab 602 defines a longitudinally extending channel 606, and extends from the second edge 35e2 of the blade body 35 (the right edge when viewing FIG. 31). As also shown in FIG. 31, the retention tab 602 has a substantially circular cross-sectional shape and defines an elongated slot 608 that provides access to the channel 606. When viewed in cross-section, the slot 608 may have any desired size, such as about 120 degrees of the circumference of the retention tab 602. Alternatively, the slot 608 may be within about 90 degrees to about 180 degrees of the circumference of the retention tab 602. The retention tab 602 may additionally have any desired cross-sectional shape, such as substantially oval, substantially rectangular, or other geometric shape.

The retention tabs 602 may have any desired length to help retain, guide, and control the endotracheal tube 92 during its positioning and delivery into the trachea. Additionally, if more than one retention tab 602 is provided, each retention tab 602 may have a different length determined by its relative position on the channel member 600.

It will be understood that any desired number of endotracheal tube retention tabs 602 may be provided. Further, the endotracheal tube retention tabs 602 may be provided at any desired location on the channel member 600, including at or near the proximal end (not shown in FIGS. 31 and 32) and at or near the distal end 35a of the blade body 35, such as shown in FIG. 32.

The retention tab 602 may be formed from any desired substantially rigid or semi-rigid material, such as PVC, wire-reinforced silicon, and stainless steel. Alternatively, the retention tab 602 may be formed from any flexible or semi-flexible material, such as silicon, rubber, wire-reinforced silicon, wire-reinforced rubber, and polymers. In addition to the flexible or semi-flexible material providing the retention tab 602 with advantageous flexibility when inserted into a patient's airway, this flexibility also provides the retention tab 602, and the slot 608 formed therein, with sufficient flexibility to facilitate insertion and removal of the endotracheal tube 92 therefrom.

If desired, the blade body 35 may include a camera channel 610 formed along the first edge 35e1 of the blade body 35 (the left edge when viewing FIG. 31). The camera channel 610 is configured to receive a second video imaging device 60', i.e., a video imaging device in addition to the video imaging device 60 in any of the flexible members described herein, including the flexible members 52, 500, 510, 520, 530, and 540. The camera channel 610 is further configured to receive a second light source 62', i.e., a light source in addition to the light source 62 in any one of the flexible members 52, 500, 510, 520, 530, and 540.

The second video imaging device 60' may be the same as the video imaging device 60 described above, and may therefore be a CMOS camera, a CCD, a fiber optic camera, and any other direct or indirect imaging device. Accordingly, an electrical wire for an imaging device such as the CCD may extend within the camera channel 610.

The second light source 62' may be the same as the light source 62 described above, and may therefore be an LED lamp or an incandescent bulb mounted at the distal end of the flexible member, such as the distal end 52a of the flexible member 52. Alternatively, the second light source 62' may be any other source of light. Additionally, the second light source 62' may be a fiber optic cable connected at its proximal end to a source of illumination (not shown), such as an LED lamp, an incandescent bulb, or any other desired light source. The video imaging devices 60 and 60' and the light sources 62 and 62' are operationally connected to the video monitor 40 and/or the controller 33 by one or more flexible electrical and/or optical connectors, shown at 66 in FIG. 6. The video monitor 40 may be configured to allow images from more than one video imaging device 60 and/or 60' to be viewed on the same screen, such as in a split screen arrangement. Alternatively, more than one video monitor 40 may be provided to allow images from more than one video imaging device 60 and/or 60' to be viewed simultaneously.

Figure 34:
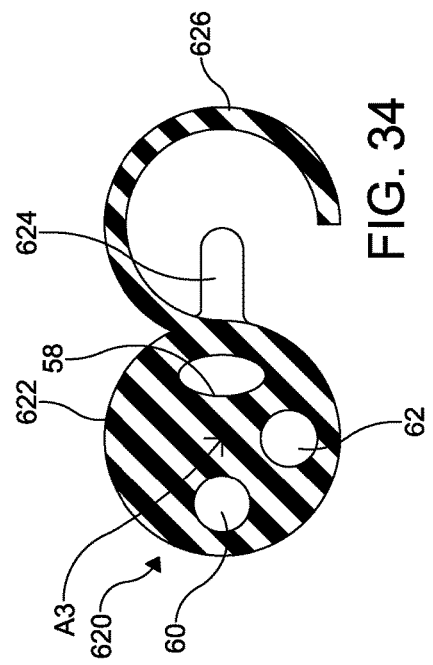
FIG. 34 is a cross-sectional view taken along the line 34-34 of FIG. 33.
Figure 35:
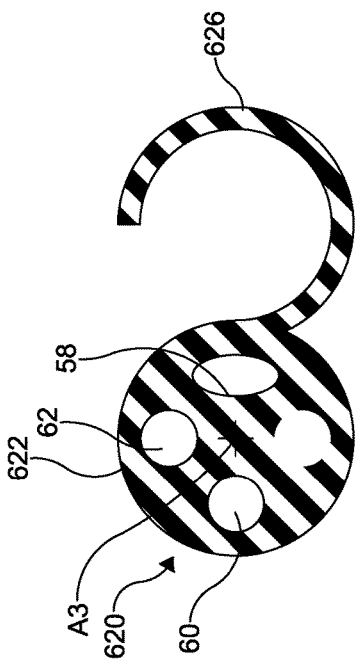
FIG. 35 is a cross-sectional view taken along the line 35-35 of FIG. 33.
Figure 33:
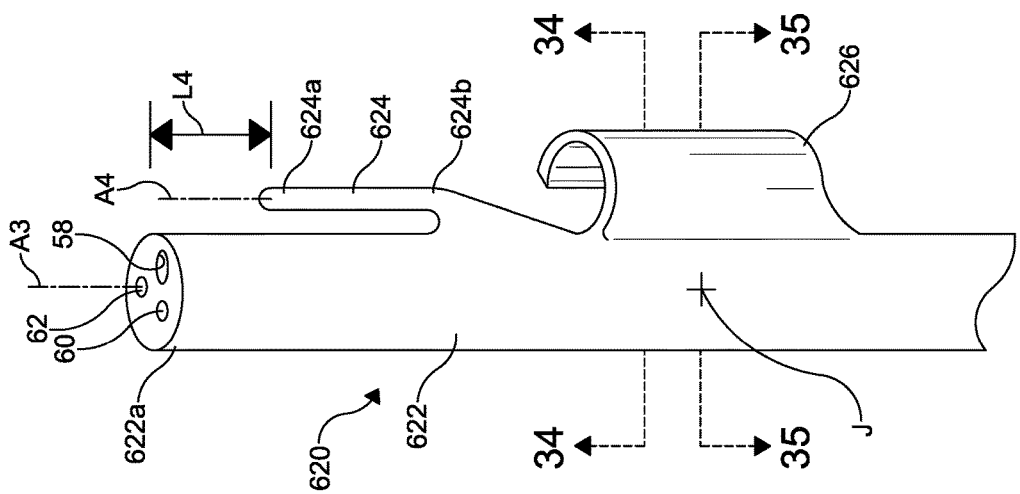
FIG. 33 is a perspective view of a portion of a seventh embodiment of the flexible member illustrated in FIG. 2.

FIGS. 33 through 35 illustrate a seventh embodiment of the flexible member 620. The flexible member 620 is similar to the flexible member 520 shown in FIG. 24. The flexible member 620 includes a body 622 having a substantially cylindrical shape, a first or distal end 622a and a second or proximal end (not shown, but substantially the same as the proximal end 52b of the flexible member 52), and the axis A3. Like the flexible member body 522, the flexible member body 622 may alternatively have any other desired cross-sectional shape, such as substantially oval, substantially hexagonal, and substantially rectangular. The flexible member body 622 includes the video imaging device 60 and the light source 62 disposed in first and second longitudinally extending conduits, described above, and the third longitudinally extending conduit 58 configured as a suction tube.

The flexible member 620 also includes the intubation assembly rod receptor 624. The intubation assembly rod receptor 624 is configured as an elongated member having the axis A4, has a substantially cylindrical shape, any desired length, and includes a first or distal end 624a. A proximal end 624b of the intubation assembly rod receptor 624 extends radially outwardly and longitudinally from the body 622 of the flexible member 620 parallel to the axis A3 of the flexible member body 622. The distal end 624a of the intubation assembly rod receptor 624 does not extend all the way to the distal end 622a of the body 622, but is spaced apart from the distal end 622a of the body 622 the distance L4 within the range of about 0.5 cm to about 2.5 cm. Alternatively, the distal end 624a of the intubation assembly rod receptor 624 may be spaced apart from the distal end 622a of the body 622 any desired distance L4, such as a distance from about 0.1 cm to about 7 cm.

The flexible member body 622 may include one or more endotracheal tube retention tabs 626 that extend outwardly from the flexible member 620. The endotracheal tube retention tab 626 configured to allow an endotracheal tube, such as the endotracheal tube 92, to be temporarily positioned and retained thereon or therein. The endotracheal tube retention tab 626 is substantially the same as the endotracheal tube retention tab 602, and will not be described in detail further. The retention tab 626 may have any desired length to help retain, guide, and control the endotracheal tube 92 during its positioning and delivery into the trachea. Additionally, if more than one retention tab 626 is provided, each retention tab 626 may have a different length determined by its relative position on the flexible member body 622.

The distal end 622a of the body 622 may include the articulating joint J, as described above and also illustrated in FIG. 6. In the embodiment of the flexible member 620 illustrated in FIG. 33, the articulating joint J is preferably located adjacent the retention tab 626, thus allowing the user to more accurately control the endotracheal tube 92 retained on or in the endotracheal tube retention tab 626.

It will be understood that any desired number of endotracheal tube retention tabs 626 may be provided. Further, the endotracheal tube retention tabs 626 may be provided at any desired location on the flexible member 620.

In FIG. 33, the endotracheal tube retention tab 626 is shown formed on the flexible member 620, which is substantially the same as the flexible member 520. It will be understood that one or more endotracheal tube retention tabs 626 may be formed on any of the flexible members described herein, including the flexible members 52, 500, 510, 520, 530, and 540. It will be further understood that the flexible member 620 may be formed with one or more endotracheal tube retention tabs 626, but without the intubation assembly rod receptor 624.

Figure 41:
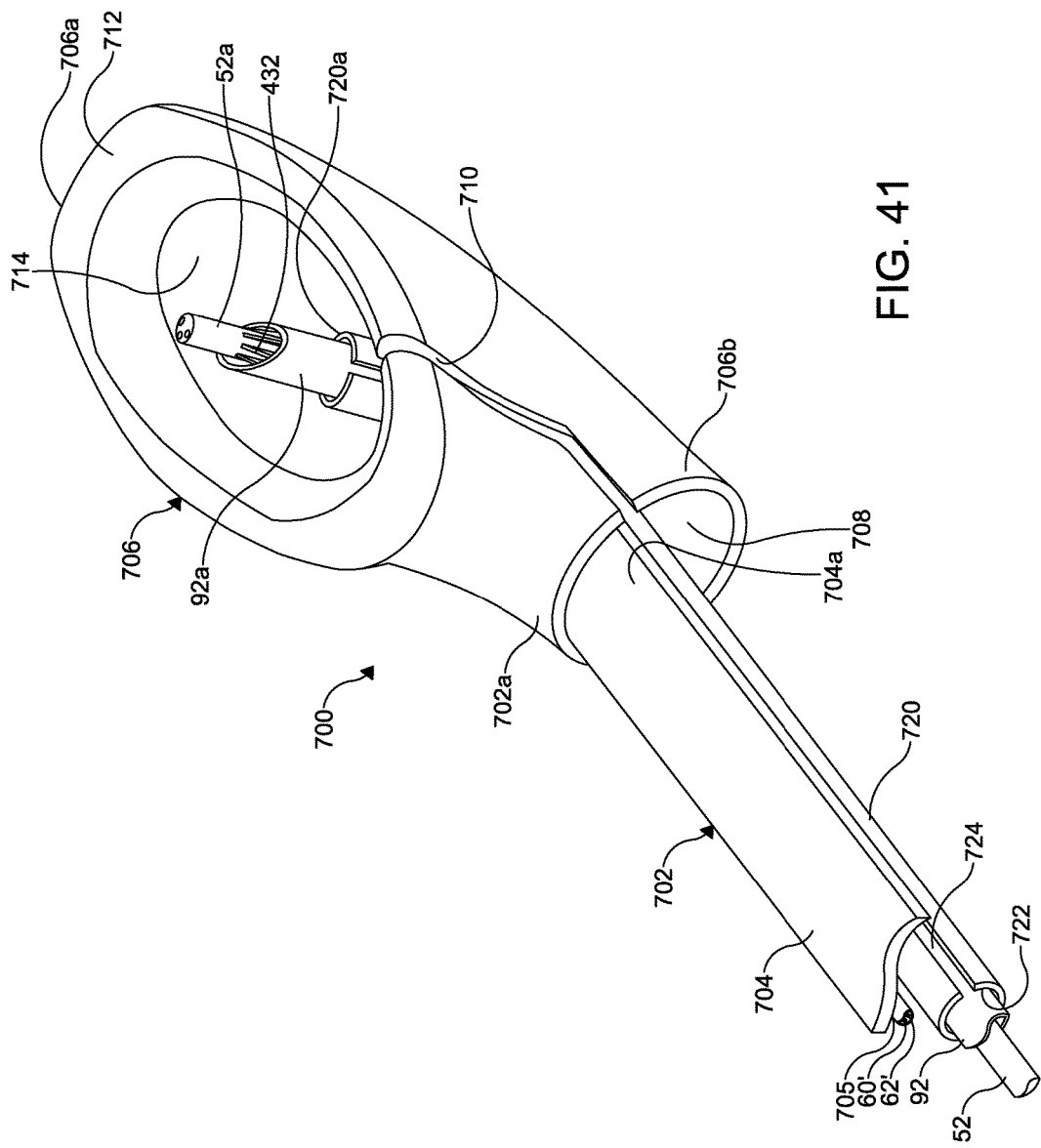
FIG. 41 is a perspective view of a fourth embodiment of the improved endotracheal tube insertion device in accordance with this invention.

A portion of a fourth embodiment of the endotracheal tube insertion device is shown at 700 in FIG. 41. In FIG. 41, the endotracheal tube insertion device 700 is a hybrid of the blade body 35 illustrated in FIGS. 2 through 4 and the endotracheal tube insertion device 230 illustrated in FIGS. 16 through 18.

The endotracheal tube insertion device 700 includes a body 702 having a blade body 704 and a generally bowl-shaped supraglottic cuff 706 formed at a distal end 702a thereof. If desired, the endotracheal tube insertion device 700 may include the handle 32, described above.

The blade body 704 is similar to the blade body 35, and includes a first or distal end 704a, a second or proximal end (not shown), but which may be attached to the handle 32 as shown in FIG. 2. Like the blade body 35, the blade body 704 is substantially straight in the longitudinal direction and has an arcuate cross-sectional shape. As shown in FIG. 41, the blade body 704 may include a third embodiment of the channel member 720 configured for attachment to the blade body 704 and further configured to receive and retain the flexible member 52 and the endotracheal tube 92 therein.

The channel member 720 includes a first or distal end 720a, a second or proximal end (not shown), defines a longitudinally extending channel 722, and is attached to an underside (lower side when viewing FIG. 41) of the blade body 704. The illustrated channel member 720 has substantially circular cross-sectional shape, and may include an elongated slot 724 that provides access to the channel 722 and facilitates removal of the endotracheal tube 92. Alternatively, the channel member 722 may have any desired cross-sectional shape, such as substantially oval, substantially rectangular, or other geometric shape. As shown, the flexible member 52 and endotracheal tube 92 are concentrically arranged wherein the flexible member 52 is inserted within the endotracheal tube 92, and the endotracheal tube 92 is inserted into the passageway channel 722.

The channel member 720 may be formed from any desired substantially rigid or semi-rigid material, such as PVC, wire-reinforced silicon, and stainless steel. Alternatively, the channel member 720 may be formed from any flexible or semi-flexible material, such as silicon, rubber, wire-reinforced silicon, wire-reinforced rubber, and polymers. In addition to the flexible or semi-flexible material providing the channel member 720 with advantageous flexibility when inserted into a patient's airway, this flexibility also provides the channel member 720, and the slot 724 formed therein, with sufficient flexibility to facilitate insertion and removal of the endotracheal tube 92 therefrom.

If desired, the distal end 52a of the flexible member 52 may have retention and transition features such as the ribs 432 (also shown in FIG. 21) having tapered leading edges similar to the ribs 74 on the rod 72, to retain the distal end 92a of the endotracheal tube 92 about the distal end 52a of the flexible member 52 during insertion into the airway. Alternatively, the distal end 52a of the flexible member 52 may have a frusto-conical shape, such as shown in FIG. 15, thus facilitating insertion of the flexible member 52 into the airway. Additionally, the distal end 52a of the flexible member 52, in an area generally the same as the area in which the tapered leading edges of the ribs 432 shown in FIG. 41 are formed, may include a solid or an inflatable portion having a tapered or frusto-conical shaped leading edge.

Significantly, the ribs 432, particularly the shape and tapered leading edges of the ribs 432, or the alternative distal end 52a having the solid or inflatable frusto-conical shaped portion, of the flexible member 52 of the improved endotracheal tube insertion device 700 are configured to prevent the leading edge or distal end 52a of the flexible member 52 from catching on laryngeal structures as the flexible member 52 and surrounding endotracheal tube 92 is advanced into the patient's airway, thus facilitating the delivery of the endotracheal tube 92 between the vocal cords and preventing trauma or injury to the vocal cords and other parts of the airway.

If desired, the blade body 704 may include a camera channel 705 formed along an edge of the blade body 704 (the left edge when viewing FIG. 41). The camera channel 705 is configured to receive the second video imaging device 60', i.e., a video imaging device in addition to the video imaging device 60 in any of the flexible members described herein, including the flexible members 52, 500, 510, 520, 530, and 540. The camera channel 705 is further configured to receive the second light source 62', i.e., a light source in addition to the light source 62 in any one of the flexible members 52, 500, 510, 520, 530, and 540.

The supraglottic cuff 706 is similar to the supraglottic cuff 237 of the supraglottic member 232 described above. The supraglottic cuff 706 includes a first or distal end 706a, a second or proximal end 706b, has a longitudinally extending passageway 708 formed therethrough, and a longitudinally extending slot 710 formed through a wall thereof. The passageway 708 is shown as being much larger than the combined size of the blade body 704, the channel member 720, and the camera channel 705 positioned therein. However, it will be understood that the supraglottic cuff 706 may be formed with a passageway 708 only large enough to position the blade body 704, the channel member 720, and the camera channel 70 therein. The slot 710 may have any desired length and width. In addition to the generally straight shape of the slot 710 shown, the slot 710 may have any other desired shape, such as a generally serpentine or wavy pattern (not shown) to assist in retaining a guided introducer intubation assembly, such as the guided introducer intubation assembly 38 within the passageway 708.

The slot 710 facilitates removal of the guided introducer intubation assembly 38, as described above. In the illustrated embodiment, the passageway 708 has a substantially oval cross-sectional shape, thus providing space, such as for the optical assembly 36 and the guided introducer intubation assembly 38, not shown in FIG. 41.

The supraglottic cuff 706 may be conventional in the art, is generally bowl-shaped, and includes a cuff wall 712 and a cuff opening 714 into which the optical assembly 36 and the guided introducer intubation assembly 38 (not shown in FIG. 41) extend. The illustrated passageway 708 has a substantially oval cross-sectional shape, however the passageway 708 may have any desired cross-sectional shape, such as substantially circular, and substantially rectangular. Additionally, the passageway 708 may have any other desired diameter or cross-sectional size.

The supraglottic cuff 706 may be formed from any of the gel-like or other substantially soft materials described above and designed to provide an anatomical, impression fit over the laryngeal inlet. Additionally the portion of the supraglottic cuff 706 in which the slot 710 is formed may be formed from any desired substantially rigid or semi-rigid material, such as PVC, silicon, rubber, wire-reinforced silicon, wire-reinforced rubber, and polymers. Providing additional rigidity to the slot 710 of the supraglottic cuff 706 provides the slot 710 sufficient rigidity to maintain its shape and retain the endotracheal tube 92 therein, while also providing sufficient flexibility to facilitate insertion and removal of the endotracheal tube 92 from the supraglottic cuff 706.

The supraglottic cuff 706 may be a non-inflatable cuff, such as the i-Gel® supraglottic airway manufactured by Intersurgical Ltd. The non-inflatable supraglottic cuff 706 may be formed of any gel-like or other substantially soft material designed to provide an anatomical, impression fit over the laryngeal inlet. Preferably, the shape, softness, and contours of the supraglottic cuff 706 accurately mirror the perilaryngeal anatomy. Alternatively, the supraglottic cuff 706, or any one or more portions thereof, may be inflatable and therefore include a conventional air inflation tube, such as the air inflation tube 242 shown in FIG. 18. The air inflation tube 242 may be attached to the supraglottic cuff 706 and configured for attachment to a source of air, such as a syringe. It will be understood that the supraglottic cuff 706 may have any desired shape, including a shape configured to displace the epiglottis and laryngeal structures to optimize the user's view of the vocal cords. Advantageously, the inflatable supraglottic cuff 706 allows the user to more easily displace laryngeal structures such as the epiglottis. The supraglottic cuff 706 may be attached to the blade body 704 by any desired method, such as with an adhesive. Alternatively, the supraglottic cuff 706 may be attached to the blade body 704 mechanically, such as with a snap-fit arrangement, or with mechanical fasteners.

FIGS. 42 through 44 illustrate a fifteenth embodiment of the intubation assembly rod 720 having a curved distal end 720*a*. The intubation assembly rod 720 is shown with the flexible member 500 to which the intubation assembly rod 720 may be attached. The flexible member 500 includes the body 502 and the intubation assembly rod receptor 504.

The intubation assembly rod 720 is similar to the intubation assembly rod 650 described above. The intubation assembly rod 720 may include the plurality of longitudinally and radially outwardly extending ribs 74. A proximal end (not shown) of the intubation assembly rod 720 may also include the threads 73 configured for connecting the intubation assembly rod 720 to the first connecting member 82, described above.

As shown in FIGS. 42 through 44, the distal end 720*a* of the intubation assembly rod 720 includes a guide system configured as the guide sleeve 722. The guide sleeve 722 includes the closed first or distal end 722*a*, an open second or proximal end 722*b*, and has an elongated channel 722*c* formed therethrough. The illustrated guide sleeve 722 is configured such that the receptors 504, 514, 524, 534, and 544 may be inserted into the channel 722*c*.

As shown in FIGS. 42 through 44, the distal end 720*a* of the intubation assembly rod 720 is bent or curved in two directions. The distal end 720*a* is curved in the positive x direction (see FIG. 44) toward the body 502 of the flexible member 500 (see FIG. 42). The distal end 720*a* is also curved in the negative y direction (see FIG. 44) away from the body 502 of the flexible member 500 (to the right when viewing FIG. 43).

Referring now to FIG. 45, an alternate embodiment of an optical assembly is shown at 36'. The optical assembly 36' is shown within the endotracheal tube insertion device 230, also shown in FIGS. 16 through 18. In the illustrated embodiment, the optical housing 50' of the optical assembly 36' includes a camera channel 51 formed longitudinally along an outside surface of the optical housing 50'. The camera channel 51 is configured to receive the second video imaging device 60', i.e., a video imaging device in addition to the video imaging device 60 in the flexible member 52. The camera channel 51 is further configured to receive the second light source 62', i.e., a light source in addition to the light source 62 in the flexible member 52.

It will be understood that the camera channel 51 may also be provided on any of the embodiments of the optical assemblies described and illustrated herein. Additionally, the camera channel 51 may be formed or otherwise attached to an inside surface of the passageway 234. The camera channel 51 may be formed from a substantially rigid material, or may be formed from the same material as the supraglottic member 232.

The second video imaging device 60' may be the same as the video imaging device 60 described above, and may therefore be a CMOS camera, a CCD, a fiber optic camera, and any other direct or indirect imaging device. Accordingly, an electrical wire for an imaging device such as the CCD may extend within the camera channel 51.

The second light source 62' may be the same as the light source 62 described above, and may therefore be an LED lamp or an incandescent bulb mounted at the distal end of the flexible member, such as the distal end 52*a* of the flexible member 52. Alternatively, the second light source 62' may be any other source of light. Additionally, the second light source 62' may be a fiber optic cable connected at its proximal end to a source of illumination (not shown), such as an LED lamp, an incandescent bulb, or any other desired light source. The video imaging devices 60 and 60' and the light sources 62 and 62' are operationally connected to the video monitor 40 and/or the controller 33 by one or more flexible electrical and/or optical connectors, shown at 66 in FIG. 6. The video monitor 40 may be configured to allow images from more than one video imaging device 60 and/or 60' to be viewed on the same screen, such as in a split screen arrangement. Alternatively, more than one video monitor 40 may be provided to allow images from more than one video imaging device 60 and/or 60' to be viewed simultaneously.

Referring now to FIG. 46, an end view of a third embodiment of the blade assembly is shown at 800. The blade assembly 800 includes the blade body 35 and a channel member 801 configured to receive and retain the flexible member 52 of the optical assembly 36 and the endotracheal tube 92. As shown, the flexible member 52 and endotracheal tube 92 are concentrically arranged wherein the flexible member 52 is inserted within the endotracheal tube 92, and the endotracheal tube 92 is inserted into a channel 802 of the channel member 801.

As described above and also shown in FIGS. 3 and 4, the blade body 35 is substantially straight in the longitudinal direction and has an arcuate cross-sectional shape. Alternatively, the blade body 35, and each embodiment of the blade body described herein, may be formed with the curved blade body 44, described in detail above and shown in FIG. 11.

The channel member 801 is attached to the first side 35*c* (lower side when viewing FIG. 46) of the blade body 35. The illustrated channel member 801 has substantially circular cross-sectional shape. Alternatively, the channel member 801 may have any desired cross-sectional shape, such as substantially oval, substantially rectangular, or other geometric shape.

As shown in FIG. 46, the channel member 801 is positioned near the second edge 35*e*2 of the blade body 35 (the right edge when viewing FIG. 46). Alternatively, the channel member 801 may be positioned near the first edge 35e1 of the blade body 35 (the left edge when viewing FIG. 46), or at any position intermediate the first edge 35e1 and the second edge 35e2.

The channel member 801 has an elongated and longitudinally extending slot 804 formed therein that provides access to the channel 802.

As shown in FIG. 46, the slot 804 of the channel member 801 opens toward the second edge 35e2 of the blade body 35 (the right edge when viewing FIG. 46). Alternatively, the slot 804 of the channel member 801 may open in any desired direction, such as toward the first edge 35e1 of the blade body 35 (the left edge when viewing FIG. 31). As also shown in FIG. 46, the channel member 801 is positioned near the second edge 35e2 of the blade body 35 (the right edge when viewing FIG. 46). Alternatively, the channel member 801 may be positioned near the first edge 35e1 of the blade body 35 (the left edge when viewing FIG. 46), or at any position intermediate the first edge 35e1 and the second edge 35e2.

Although not shown in FIG. 46, the distal end 52a of the flexible member 52 may have retention features such as the ribs 432 (also shown in FIGS. 21 and 41) having tapered leading edges similar to the ribs 74 on the rod 72, to retain the distal end (not shown in FIG. 46) of the endotracheal tube 92 about the distal end (not shown in FIG. 46) of the flexible member 52 during insertion into the airway. Alternatively, the distal end (not shown in FIG. 46) of the flexible member 52 may have a frusto-conical shape, such as shown in FIG. 15, thus facilitating insertion of the flexible member 52 into the airway. Additionally, the distal end (not shown in FIG. 46) of the flexible member 52, in an area generally the same as the area in which the tapered leading edges of the ribs 432, such as shown in FIG. 41, are formed, may include a solid or an inflatable portion having a tapered or frusto-conical shaped leading edge.

Significantly, the ribs 432, particularly the shape and tapered leading edges of the ribs 432, or the alternative distal end (not shown in FIG. 46) having the solid or inflatable frusto-conical shaped portion, of the flexible member 52 of the improved blade assembly 800 are configured to prevent the leading edge or distal end (not shown in FIG. 46) of the flexible member 52 from catching on laryngeal structures as the flexible member 52 and surrounding endotracheal tube 92 are advanced into the patient's airway, thus facilitating the delivery of the endotracheal tube 92 between the vocal cords and preventing trauma or injury to the vocal cords and other parts of the airway.

Figure 47:
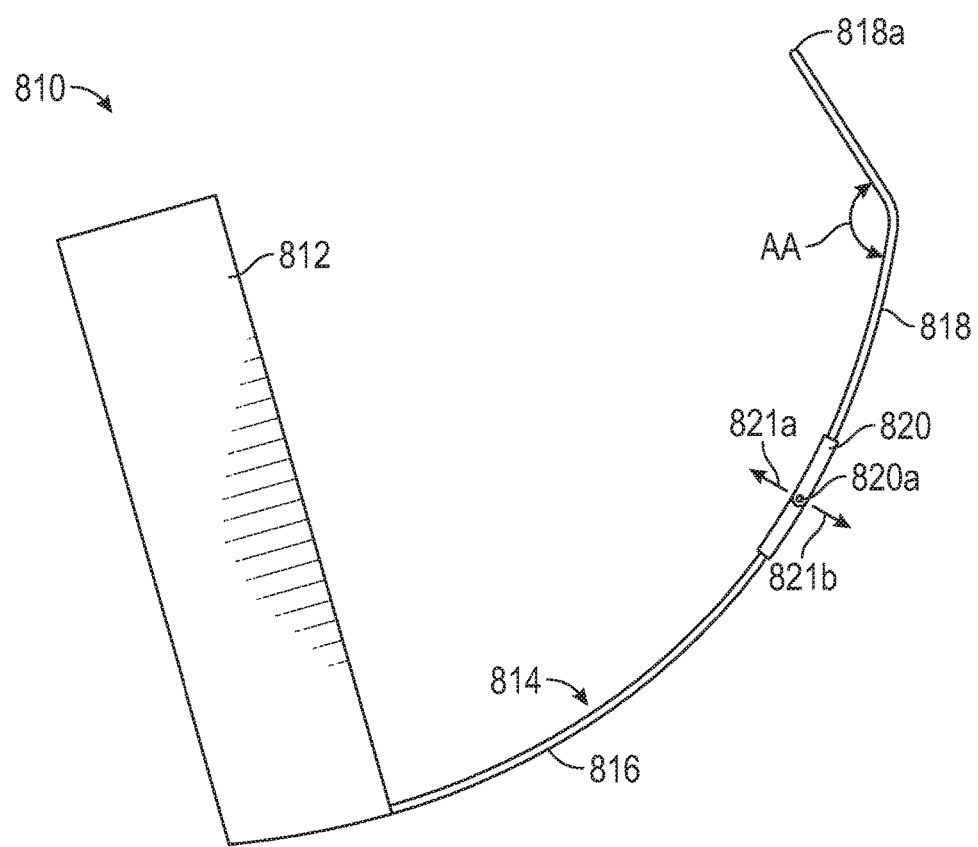
FIG. 47 is a schematic side elevational view of a portion of an endotracheal tube insertion device showing an alternative embodiment of a blade body.

Referring now to FIG. 47, a portion of an endotracheal tube insertion device is shown at 810 and includes a handle 812 and an alternative embodiment of a blade body 814. The handle may be substantially the same as the handle 32. The blade body 814 includes a first blade portion 816 and a second blade portion 818 pivotally connected together by pivot mechanism 820 about a pivot axis 820a. The pivot mechanism 820 is configured to allow the second blade portion 818 to be pivotally moved relative to the first blade portion 816 about the pivot axis 820a in the direction of the arrows 821a and 821b.

The blade body 814 is elongated and upwardly curved, and thus has a shape similar to the blade body 44. If desired, the second blade portion 818 may be bent inwardly, (toward the handle 812 when viewing FIG. 47) at a point intermediate a distal end 818a of the second blade portion 818 and the pivot axis 820a. The second blade portion 818 may be inwardly bent any desired angle AA, such as within the range of about 115 degrees to about 175 degrees. This increased bend angle at the second blade portion 818; i.e., the distal end of the blade body 14, advantageously allows the user, such as a physician to achieve a more pronounced tissue retraction and anterior camera angulation. Alternatively, the blade body 814 may also be straight, such as the blade body 35, and include the pivot mechanism 820 and/or have a distal end portion inwardly bent at the angle AA.

The blade body 814 may be used in lieu of the blades illustrated in any embodiments of the endotracheal tube insertion device described herein. Additionally, the blade body 814 may be used in lieu of the blade body 704 of the endotracheal tube insertion device 700 shown in FIG. 41.

Figure 48:
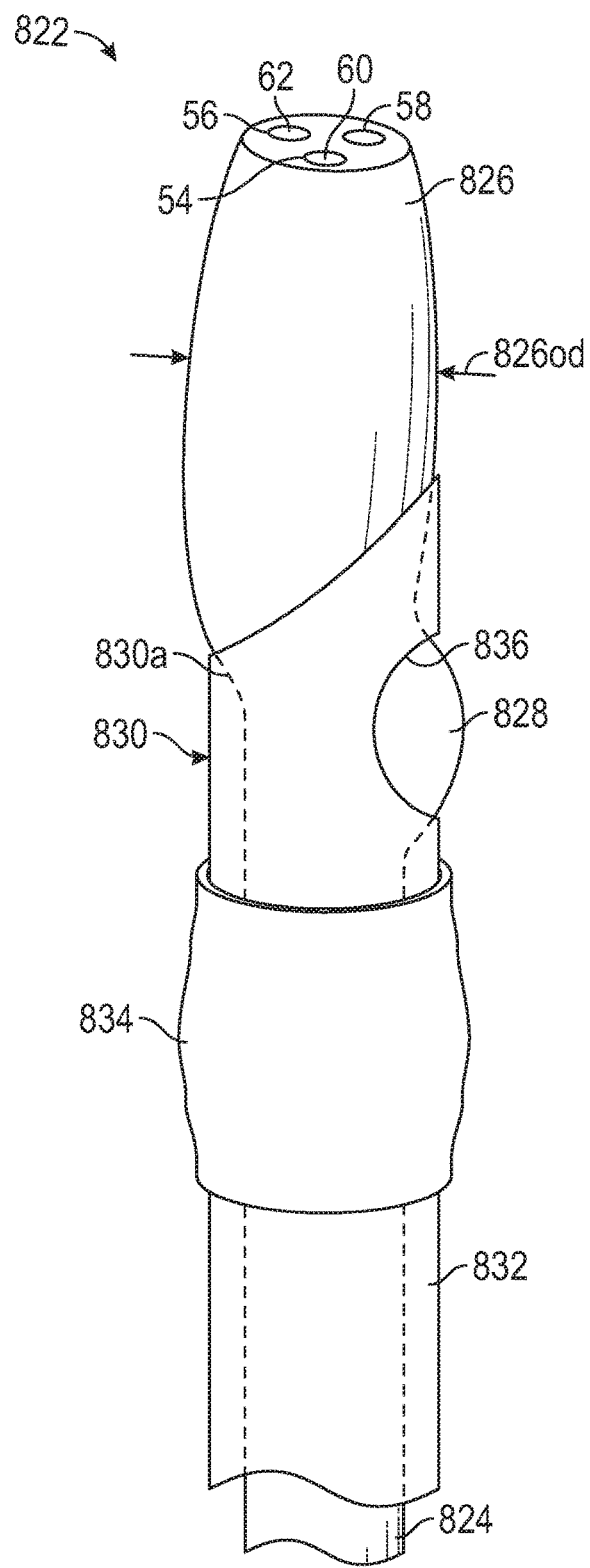
FIG. 48 is a perspective view of a portion of an alternate embodiment of a flexible member according to this invention.

Referring now to FIG. 48, an alternate embodiment of a flexible member is shown at 822. Like the embodiments the flexible member described herein above, the flexible member 822 is an elongated member having an axis A9. The flexible member 822 further includes a body 824 having a substantially cylindrical shape. A first or distal end 826 of the flexible member 822 is enlarged. In the illustrated embodiment, the distal end 826 has a substantially barrel shape. A positioning plug 828 extends radially outward of the flexible member 822 intermediate the body 824 and the distal end 826. Alternatively, the distal end 826 may have other desired shapes, such as football shaped, or spherical. If desired, the barrel shape, football shape, spherical, or other shape structure of the distal end 826 may be configured to be inflatable or compressible.

As also described above, a plurality of longitudinally extending conduits is formed within the flexible member 822. As shown in FIG. 48, the flexible member 822 includes the first longitudinally extending conduit 54, the second longitudinally extending conduit 56, and the third longitudinally extending conduit 58. The video imaging device 60 is disposed in the first longitudinally extending conduit 54. A light source 62 is disposed in the second longitudinally extending conduit 56. The third longitudinally extending conduit 58 is configured as a suction tube and is connected to a vacuum port, such as the vacuum port 59 extending outward of the knob 68a shown in FIG. 5.

In FIG. 48, a conventional endotracheal tube 830 is shown concentrically mounted on the flexible member 822. The endotracheal tube 830 has a first or distal end 830a and a second or proximal end (not shown). The endotracheal tube 830 further includes a tube body 832 having balloon cuff 834 near the distal end 830a. A conventional Murphy eye 836 is formed between the cuff 834 and the distal end 830a. As shown, the positioning plug 828 is configured to extend through the Murphy eye 836 to hold the endotracheal tube 830 in place relative to the flexible member 822 during insertion into the airway. It will be understood that all embodiments of the intubation assembly rods disclosed herein may be formed having the positioning plug 828.

Preferably, the widest outside diameter 826od of the barrel shaped distal end 826 of the flexible member 822 is equal to or slightly larger than an outside diameter of the endotracheal tube 830. If the material forming the distal end 826 of the flexible member 822 is not compressible, only a portion of its outside diameter may be equal to or slightly larger than the outside diameter of the endotracheal tube 830 so the flexible member 822 may fit through and be removed from the inside of the endotracheal tube 830.

Figure 49:
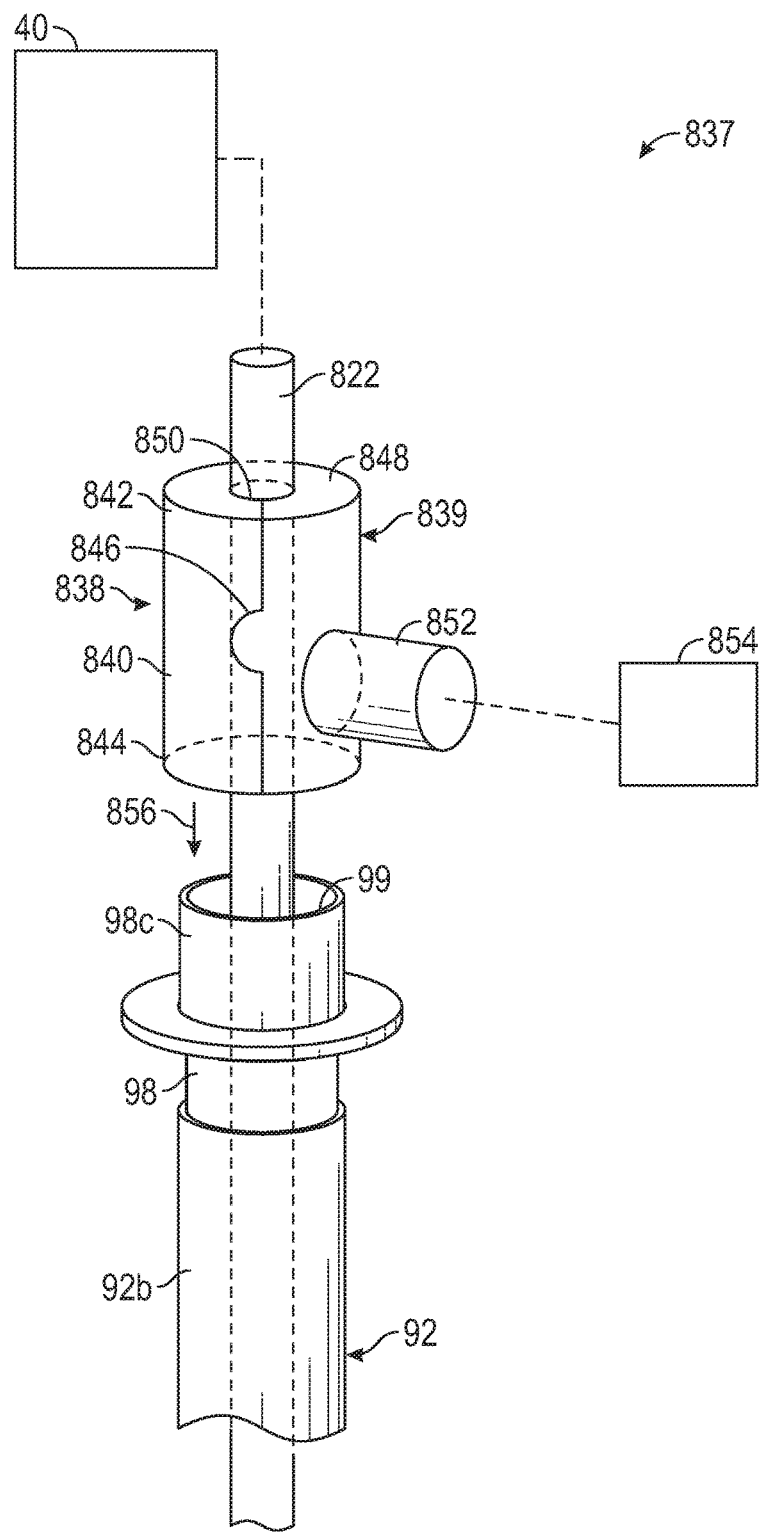
FIG. 49 is a perspective view of a first embodiment of an oxygen source cap according to this invention shown mounted on a flexible member.

Referring now to FIG. 49, a portion of an endotracheal tube insertion device is shown at 837. The endotracheal tube insertion device 837 is similar to the endotracheal tube insertion device 330 in FIG. 21 and the endotracheal tube insertion device 700 in FIG. 41, and includes the endotracheal tube 92 attached to the connector 98, both described in detail above and concentrically mounted on a flexible member, such as the flexible member 822. A video monitor, schematically illustrated at 40 is attached to a proximal end of an optical assembly of which the flexible member 822 is a component and, as described above, is operationally connected to a video imaging device (not shown), such as the video imaging device 60 shown in FIG. 7.

A first embodiment of an oxygen source cap 838 is mounted concentrically about the flexible member 822 between a proximal end 827 thereof and the endotracheal tube connector 98. The oxygen source cap 838 has a body 839 having a circumferentially extending wall 840 defining a generally cylindrical outside surface, a first end 842 (the upper end when viewing FIG. 49), and a second end 844 (the lower end when viewing FIG. 49). A longitudinally extending slit 846 is formed through the wall 840 and defines a closure member. The slit 846 may be opened to allow the oxygen source cap 838 to be mounted on the flexible member 822 and closed to allow the oxygen source cap 838 to be attached to the flexible member 822.

An end wall 848 is formed at the first end 842 and has an aperture 850 formed centrally therethrough. When the oxygen source cap 838 is mounted on the flexible member 822, the end wall 848 provides a fluid-tight seal about the flexible member 822. The second end 844 of the oxygen source cap 838 is open. A generally cylindrical fluid inlet 852 extends radially outward of the wall 840 and is in fluid communication with the open second end 844 of the oxygen source cap 838. The fluid inlet 852 may be connected to source of oxygen, schematically illustrated at 854.

In operation, the oxygen source cap 838 may be urged into contact with the connector 98 such that a proximal end 98*c* of the connector 98 is inserted into the open second end 844 of the oxygen source cap 838. Oxygen from the source of oxygen 854 may then flow through the oxygen source cap 838 into the endotracheal tube 92 via the longitudinally extending channel 99 of the connector 98; i.e., in the direction of the arrow 856.

Figure 50:
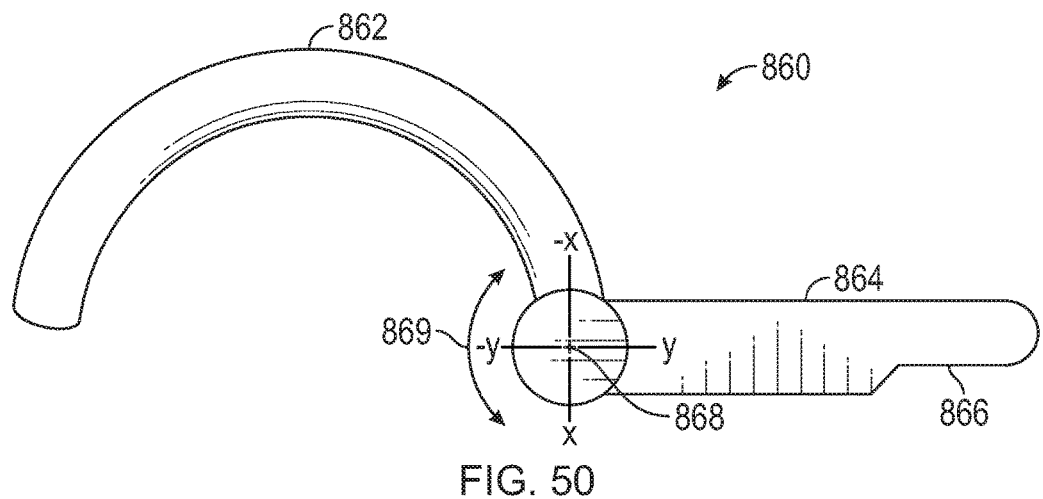
FIG. 50 is a top plan view of a first embodiment of a handle and blade assembly according to this invention.

Referring now to FIG. 50, a first embodiment of a handle and blade assembly is shown at 860. The handle and blade assembly 860 is configured for use with an endotracheal tube insertion device, such as the endotracheal tube insertion device 30 in FIG. 2, and incldes a handle 862 and a blade 864. The blade 864 is similar to the blade body 34, but includes a longitudinally extending notch 866 at distal end thereof.

The blade 864 is elongated and extends in a first direction. The handle 862 is arcuate and extends rearwardly from the blade 864. Alternatively, the handle 862 may have any other desired shape.

If desired, the blade 864 may be pivotally attached to the handle 862 about a pivot axis 868 such that the blade 864 may be pivoted relative to the handle 862 clockwise or counterclockwise (see the arrow 869). The handle and blade assembly 860 may also be provided with a mechanism (not shown) to lock or prevent the blade 864 from pivoting relative to the handle 862, or to otherwise control the pivoting movement of the blade 864 relative to the handle 862.

Figure 51:
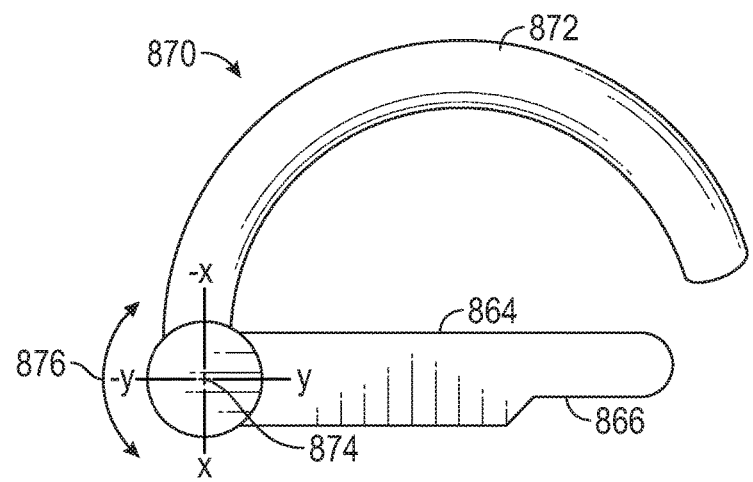
FIG. 51 is a top plan view of a second embodiment of the handle and blade assembly illustrated in FIG. 50.

Referring now to FIG. 51, a second embodiment of a handle and blade assembly is shown at 870. The handle and blade assembly 870 is configured for use with an endotracheal tube insertion device, such as the endotracheal tube insertion device 30 in FIG. 2, and includes a handle 872 and the blade 864 having the notch 866.

The blade 864 is elongated and extends in a first direction. The handle 872 is arcuate, extends forwardly toward a distal end of the blade 864. Alternatively, the handle 872 may have any other desired shape.

If desired, the blade 864 may be pivotally attached to the handle 872 about a pivot axis 874 such that the blade 864 may be pivoted relative to the handle 872 clockwise or counterclockwise (see the arrow 876). The handle and blade assembly 870 may also be provided with the mechanism (not shown) to lock or prevent the blade 864 from pivoting relative to the handle 872, or to otherwise control the pivoting movement of the blade 864 relative to the handle 872.

Figure 52:
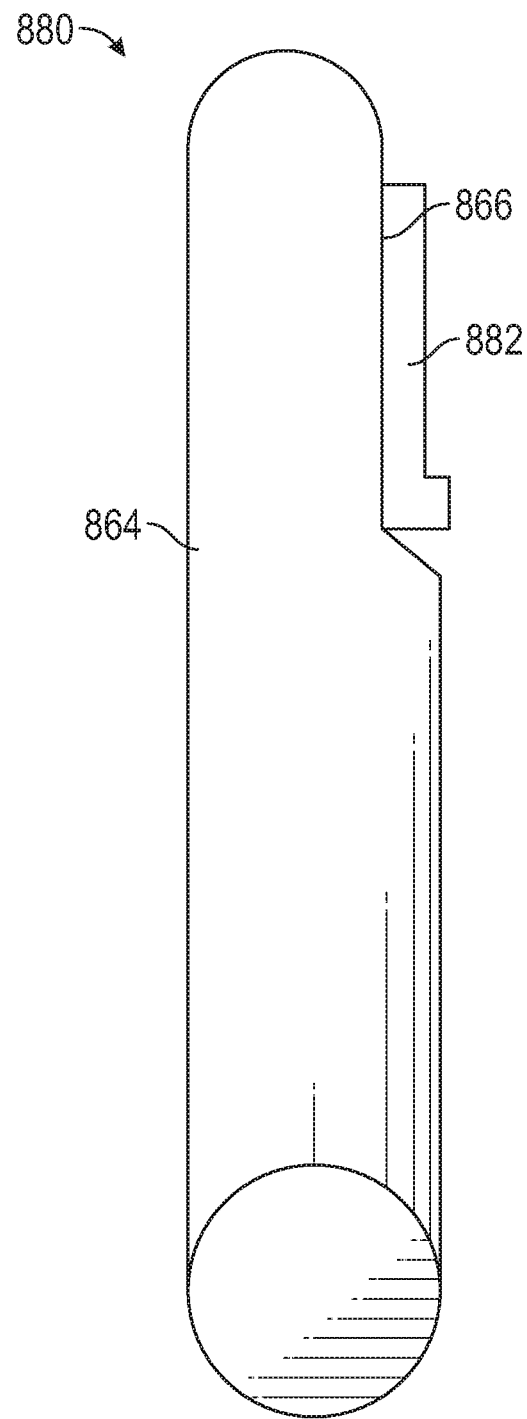
FIG. 52 is an enlarged top plan view of an alternative embodiment of a blade assembly according to this invention.

FIG. 52 is an enlarged top plan view of an alternative embodiment of a blade assembly 880. The blade assembly 880 includes the blade 864 having the notch 866. A channel member 882 is attached to an underside of the blade 864 at the notch 866. The channel member 882 may be any of the channel members described and illustrated herein above, including but not limited to the retention tabs 39*a*, 39*b*, 49*a*, 49*b*, 602, and 626, or any of the optical assembly channel members described and illustrated herein.

Figure 53:
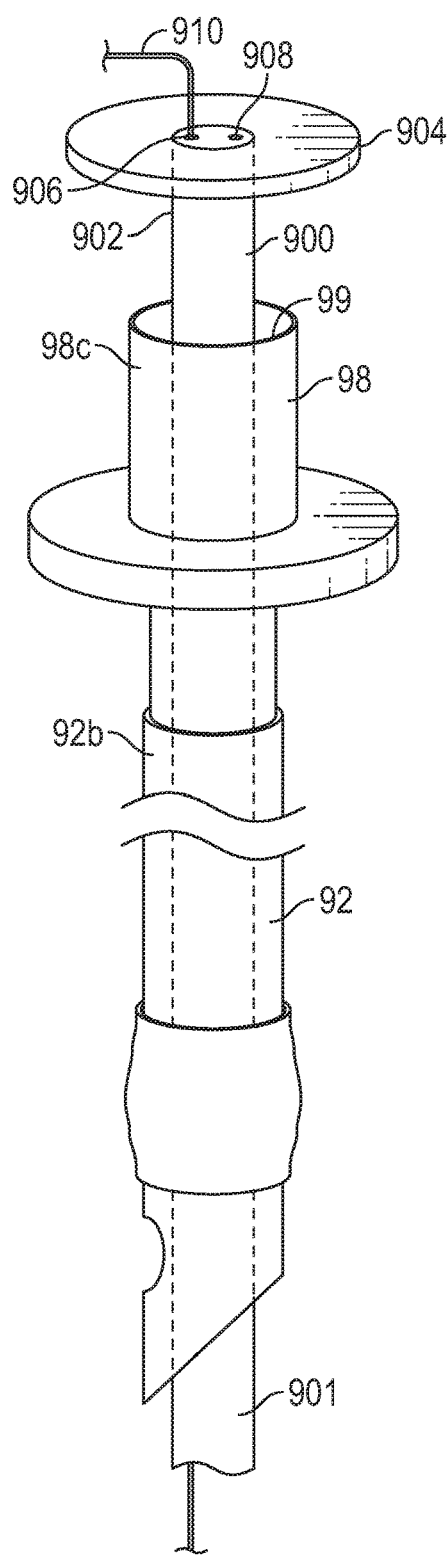
FIG. 53 is a perspective view of a sixteenth embodiment of the intubation assembly rod shown inserted in a conventional endotracheal tube and a conventional endotracheal tube connector.

FIG. 53 illustrates a sixteenth embodiment of the intubation assembly rod 900 shown inserted through the longitudinally extending channel 99 of the conventional endotracheal tube connector 98 and into the conventional endotracheal tube 92. The intubation assembly rod 900 has an elongated body 901 having a proximal end 902 (the upper end when viewing FIG. 53) and a distal end (not shown) opposite the proximal end 902. The proximal end 902 further has a radially extending flange defining a stop 904 extending therefrom.

One or more longitudinally extending conduits may be formed within the intubation assembly rod 900. As shown in FIG. 53, the intubation assembly rod 900 includes two such conduits: a first longitudinally extending conduit 906, and a second longitudinally extending conduit 908. A guidewire 910 is disposed in the first longitudinally extending conduit 906. The second longitudinally extending conduit 908 is configured as a suction tube and thus may be connected to a vacuum port (not shown in FIG. 53), such as the vacuum port 59 extending outward of the knob 68*a*, shown in FIG. 5. Although described as a suction tube, the second longitudinally extending conduit 908 may also be used to provide oxygen to a patient. Alternatively, each of the first longitudinally extending conduit 906 and the second longitudinally extending conduit 908 may be used for any other desired purpose.

The stop 904 is configured to help retain the intubation assembly rod 900 in a desired position within the endotracheal tube 92. The stop 904 may be attached to the proximal end 902 of the intubation assembly rod 900. Alternatively, the stop 904 may be movably mounted to the proximal end 902 of the intubation assembly rod 900 and thus configured to slide along the length of the intubation assembly rod 900. In lieu of the stop 904 being configured as a flange, the proximal end 902 of the intubation assembly rod 900 may include other structures, such as a threaded retainer, a snap close mechanism, a snap sideways mechanism, a resilient stopper, and other similar structures configured to retain the intubation assembly rod 900 in a desired position within the endotracheal tube 92 and to prevent accidental migration into the trachea. It will be understood that the stop 904 and the alternative structures described herein above, may be used with any of the embodiments of the intubation assembly rods described herein and with any of the embodiments of the flexible members describe herein.

The proximal end 902 of the intubation assembly rod 900 may also be configured to be adjustable in length so as to accommodate endotracheal tubes 92 having a plurality of lengths. In an embodiment wherein the stop 904 is movably mounted to the proximal end 902 of the intubation assembly rod 900, the stop may be positioned to allow for endotracheal tubes 92 having a plurality of different lengths.

Figure 54:
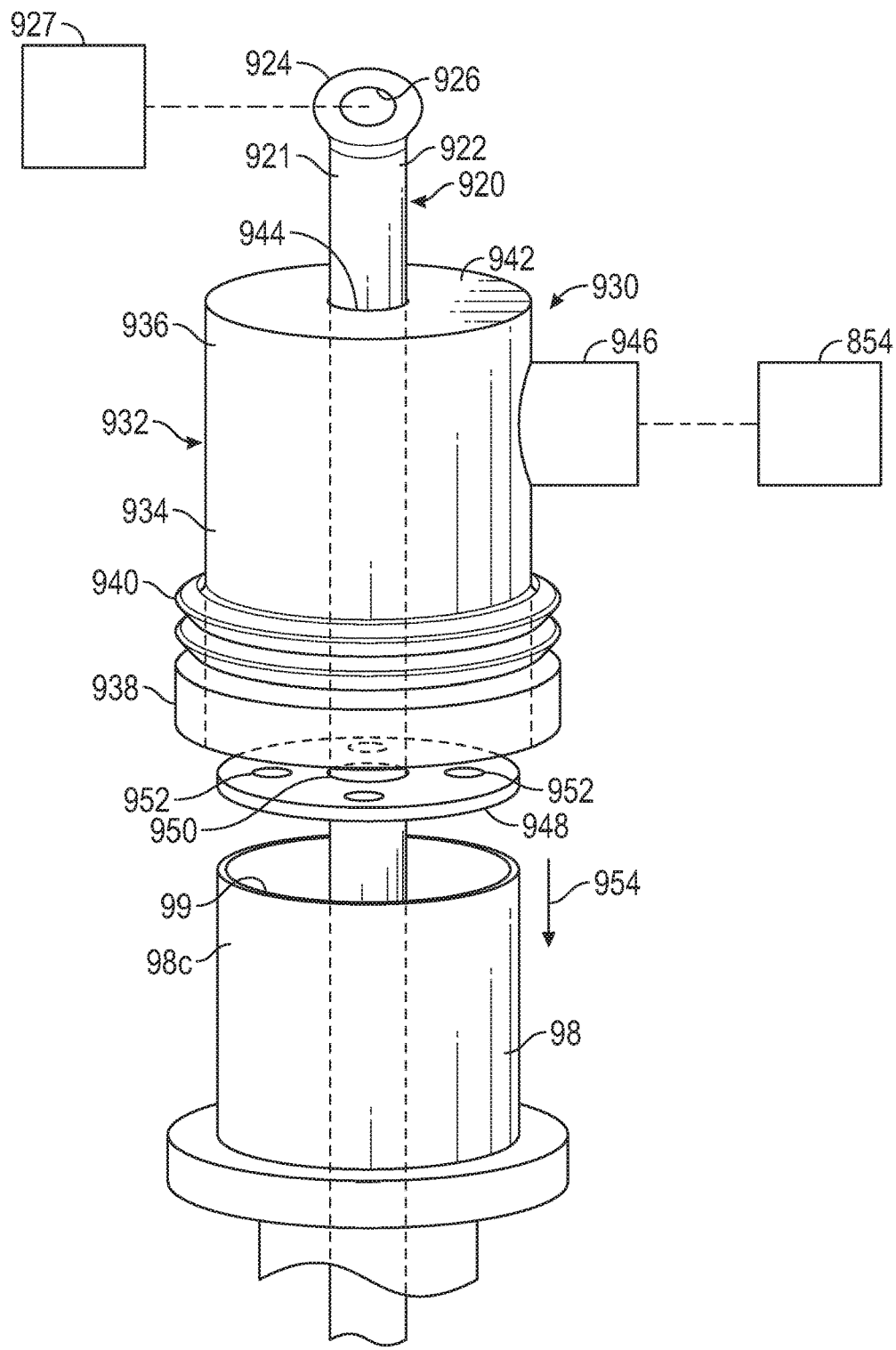
FIG. 54 is a perspective view of a seventeenth embodiment of the intubation assembly rod shown inserted in a conventional endotracheal tube connector and having a second embodiment of the oxygen source cap mounted thereon.

FIG. 54 illustrates a seventeenth embodiment of the intubation assembly rod 920 shown inserted through the longitudinally extending channel 99 of the conventional endotracheal tube connector 98 and into the conventional endotracheal tube 92 (not shown in FIG. 54). The intubation assembly rod 920 has an elongated body 921 having a proximal end 922 (the upper end when viewing FIG. 54) and a distal end (not shown) opposite the proximal end 922. If desired, the proximal end 922 may include an end portion 924 that extends at about a 90 degree angle therefrom. Alternatively, the end portion 924 may extend at any other desired angle relative to an axis of the intubation assembly rod 920, such as within the range of about 0 degrees to about 180 degrees.

A longitudinally extending conduit 926 may be formed within the intubation assembly rod 920. In FIG. 54, the longitudinally extending conduit 926 is configured as a suction tube and thus may be connected to a vacuum port, shown schematically at 927 in FIG. 54, and similar to the vacuum port 59 extending outward of the knob 68a, shown in FIG. 5. Although described as a suction tube, the longitudinally extending conduit 926 may also be used to provide oxygen to a patient. Alternatively, the longitudinally extending conduit 926 may be used for any other desired purpose.

A second embodiment of an oxygen source cap 930 is mounted concentrically about the intubation assembly rod 920 between the proximal end 922 thereof and the endotracheal tube connector 98. The oxygen source cap 930 has a body 932 having a circumferentially extending wall 934 defining a generally cylindrical outside surface, a first end 936 (the upper end when viewing FIG. 54), and a second end (the lower end when viewing FIG. 54) that defines an annular collar 938. A portion of the body 932 adjacent the collar 938 is configured as a bellows 940. Alternatively, the portion of the body 932 adjacent the collar 938 may have any structure configured to allow the body 932 to expand and contract longitudinally. Preferably, the bellows 940 will allow the oxygen source cap 930 to expand up to about 6 cm. Alternatively, the bellows 940 will allow the oxygen source cap 930 to expand within the range of up to about 10 cm from its fixed or unexpanded condition.

An end wall 942 is formed at the first end 936 of the oxygen source cap 930 and has an aperture 944 formed centrally therethrough. When the oxygen source cap 930 is mounted on the intubation assembly rod 920, the end wall 942 provides a fluid-tight seal about the intubation assembly rod 920. The end wall 942 may be attached to the proximal end 922 of the intubation assembly rod 920. Alternatively, the end wall 942 may be movably mounted to the proximal end 922 of the intubation assembly rod 920 and thus configured to slide along the length of the intubation assembly rod 920.

The elongated body 921 may have a proximal end 922 that is closed and mounted flush with the end wall 942. In such an embodiment, the end wall 942 may be formed without the aperture 944, and the intubation assembly rod 920 may be attached thereto. If desired, the intubation assembly rod 920 may be formed without the conduit 926 or may be formed with a plurality of conduits, such as the conduits 906 and 908 described above.

The collar 938 at the second end of the oxygen source cap 930 is open. A generally cylindrical fluid inlet 946 extends radially outward of the wall 934 and is in fluid communication with the open collar 938 of the oxygen source cap 930. An axis of the fluid inlet 946 may be oriented in any desired direction relative to an axis of the oxygen source cap 930. Additionally, the fluid inlet 946 may be formed on the end wall 942 if desired. The fluid inlet 946 may be connected to source of oxygen, schematically illustrated at 854.

An annular stop 948 includes a centrally formed aperture 950 through which the intubation assembly rod 920 may extend, and a plurality of air flow holes 952 formed therethrough. The stop 948 may be fixedly attached to the intubation assembly rod 920 and may be attached within the collar 938. Alternatively, the stop 948 may be movably mounted to the intubation assembly rod 920 and thus configured to slide along a portion of the of the intubation assembly rod 920. In the illustrated embodiment, four air flow holes 952 are shown. Alternatively, any desired number of air flow holes 952 may be formed in the annular stop 948.

If desired, the intubation assembly rod 920 may terminate at a first side of the stop 948 (the upwardly facing side when viewing FIG. 54).

In operation, the oxygen source cap 930 may be urged into contact with the connector 98 such that a proximal end 98c of the connector 98 engages the stop 948 of the oxygen source cap 930. Oxygen from the source of oxygen 854 may then flow through the oxygen source cap 930 into the endotracheal tube 92 via the longitudinally extending channel 99 of the connector 98; i.e., in the direction of the arrow 954.

Additionally, the bellows 940 of the oxygen source cap 930 allows the oxygen source cap 930 to be selectively extended a distance, such as up to about 6 cm to facilitate a secure connection between the oxygen source cap 930 and the proximal end 98c of the connector 98 particularly when the endotracheal tubes 92 are of different lengths.

Figure 59:
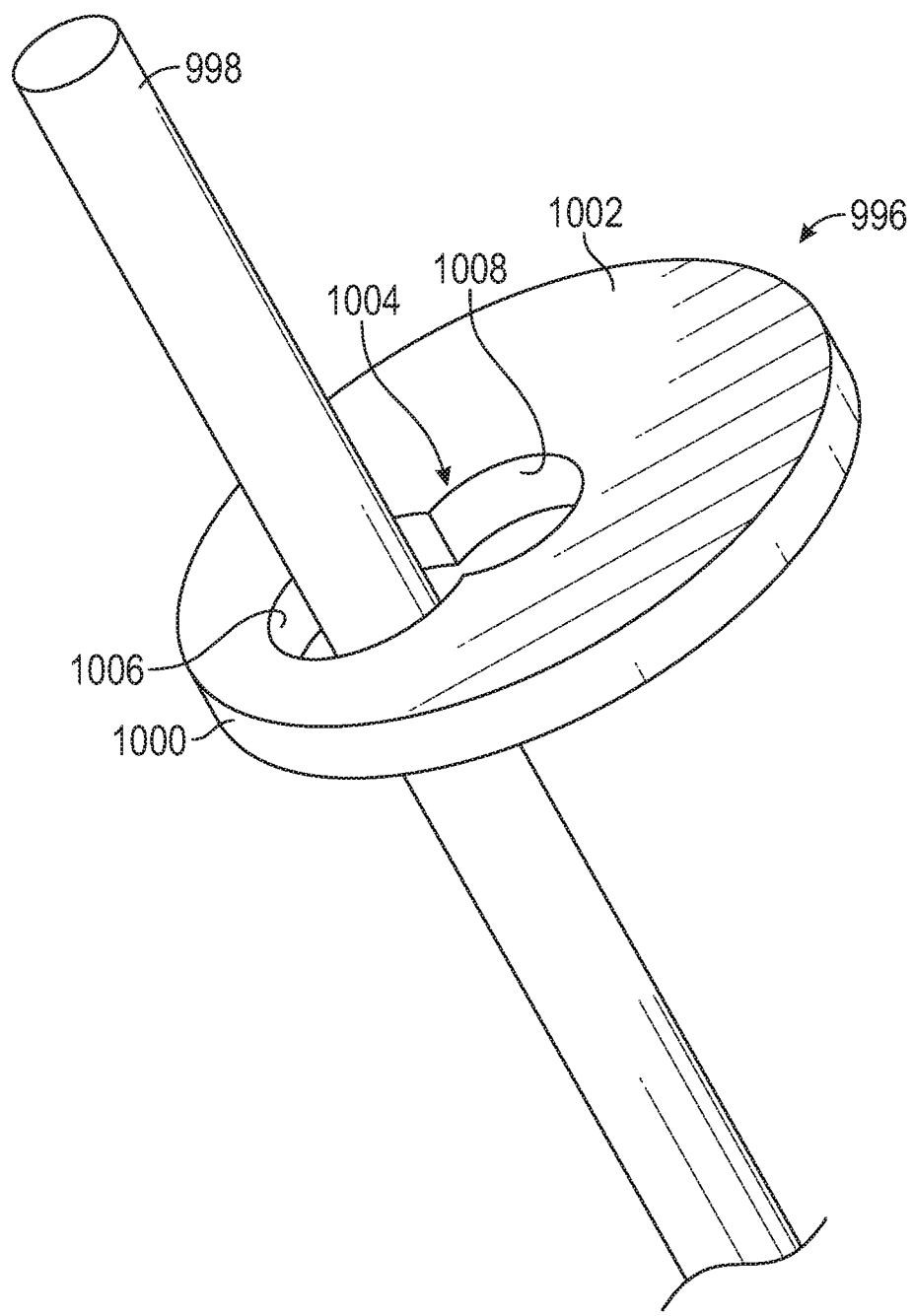
FIG. 59 is a perspective view of a third embodiment of the oxygen source cap mounted shown with an intubation assembly rod.

An alternate embodiment of a stop 996 is shown in FIG. 59 mounted about an intubation assembly rod 998. The stop 996 has a disk-shaped body 1000 and has an aperture 1004 formed therethrough. In FIG. 59, the aperture 1004 is configured as a plurality of connected apertures. The aperture 1004 includes a first aperture portion 1006 and a second aperture portion 1008. Both aperture portions 1006 and 1008 are substantially circular. The diameter of the second aperture portion 1008 is about equal to a diameter of the intubation assembly rod 998, such that when inserted therein, the intubation assembly rod 998 is held within the second aperture portion 1008, such as in a snap-fit arrangement. A diameter of the first aperture portion 1006 is slightly larger than the diameter of the second aperture portion 1008.

The first aperture portion 1006 and the second aperture portion 1008 of the aperture 1004 facilitate the movement of the stop 996 along the intubation assembly rod 998. For example, to move the stop 996 longitudinally along the rod 998, the rod 998 may be positioned in the first aperture portion 1006 and the stop 996 may then be moved longitudinally to a desired position. When the stop 996 is positioned longitudinally in the desired position, the stop 996 may be attached to the rod 998 by moving the stop 996 laterally such that the rod 998 moves from the first aperture portion 1006 to the second aperture portion 1008 and is attached therein, such as in a snap-fit arrangement.

Figures 55, 56:
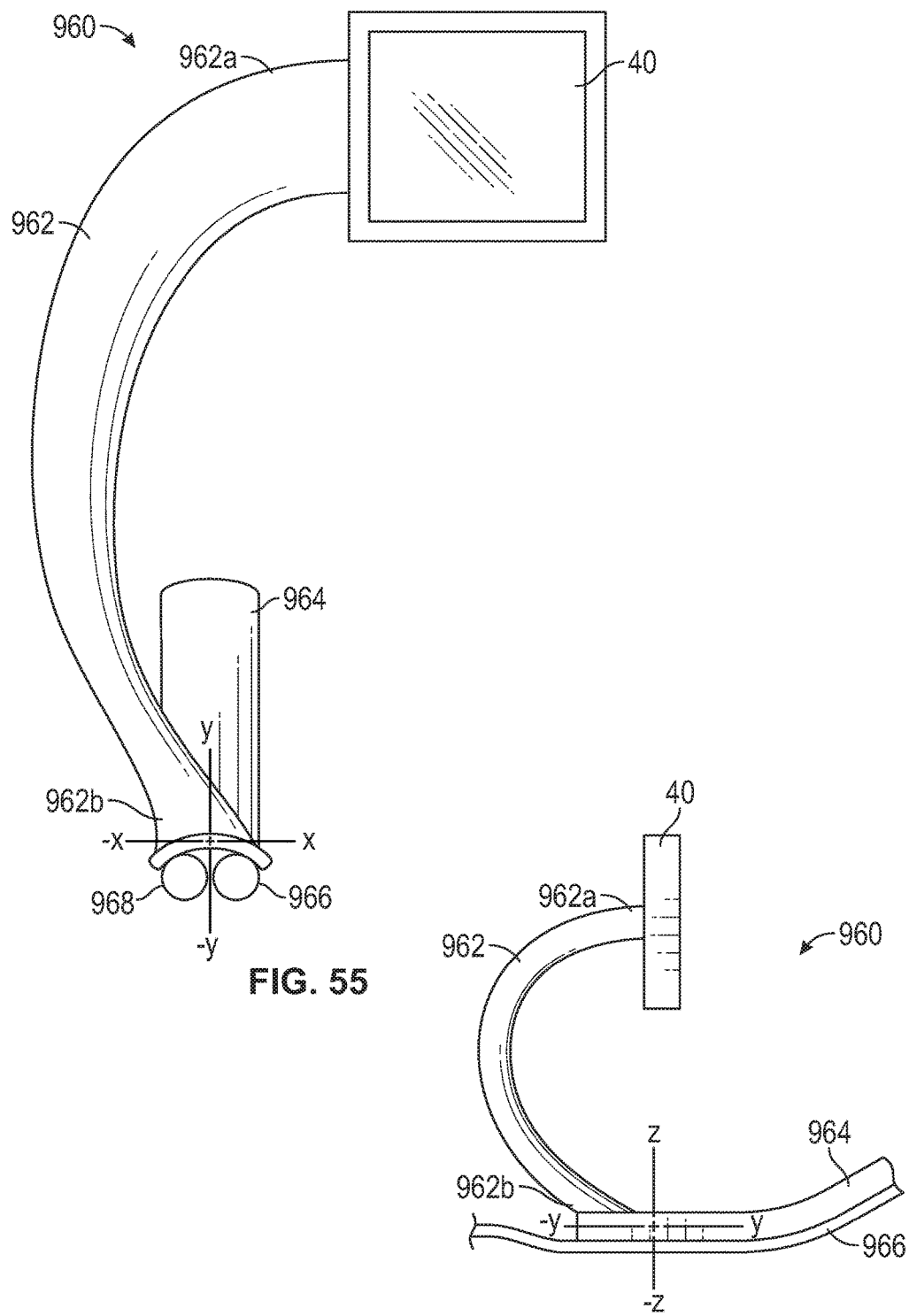
FIG. 55 is a top plan view of a third embodiment of a handle and blade assembly according to this invention.
FIG. 56 is a side elevational view of the handle and blade assembly illustrated in FIG. 55.

Referring now to FIG. 55, a third embodiment of a handle and blade assembly is shown at 960. The handle and blade assembly 960 is configured for use with an endotracheal tube insertion device, such as the endotracheal tube insertion device 30 in FIG. 2, and includes a handle 962 and a blade 964. The handle 962 has a first end 962a and a second end 962b. It will be understood that the handle 962 may be used with any of the embodiments of the insertion members described herein. If desired, the blade 964 may be pivotally attached to the handle 962, as shown in FIGS. 50 and 51.

A video monitor 40 is attached to the first end 962a of the handle 962 and is operationally connected to a video imaging device, such as the video imaging device 60, shown in FIG. 7. A channel member 966 and/or an optical housing 968 may be attached to the blade 964.

As shown in FIGS. 55 and 56, the first end 962a of the handle 962, i.e., the end to which the video monitor 40 is attached, is bent or curved in two directions, wherein each of the two directions define axes different from an axis of the second end 962b of the handle 962. The first end 962a is curved in the negative x direction (see FIG. 55) and is also curved in the negative y direction (see FIG. 56) away from the blade 964.

It will be understood that all embodiments of the portions of the endotracheal tube insertion devices disclosed herein, including all embodiments of insertion members, optical assemblies, optical housings, flexible members, channel members, and intubation assembly rods, that may be inserted into an airway may be shrouded, such as with a shroud formed from nylon, polyurethane, polyester, or silicone, may be encased in a disposable sheath, or may be formed as a one-time use disposable item.

It will be further understood that all embodiments of the intubation assembly rods disclosed herein may be formed curved, i.e., having a slightly arcuate shape that corresponds to the natural curvature of a conventional endotracheal tube. This arcuate shape allows for more intuitive placement into the endotracheal tube and facilitates easier passage in and out of the endotracheal tube.

Figure 57:
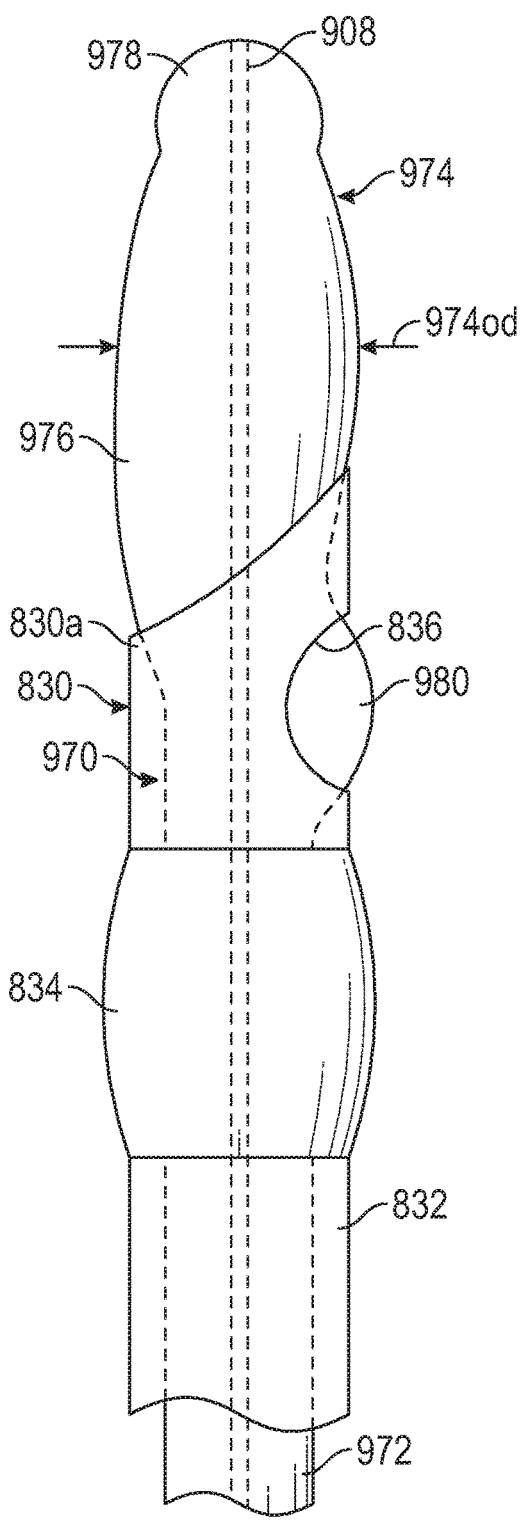
FIG. 57 is a side elevational view of a portion of an eighteenth embodiment of the intubation assembly rod.

Referring now to FIG. 57, a portion of an eighteenth embodiment of an intubation assembly rod is shown at 970. In FIG. 57, the conventional endotracheal tube 830 is shown concentrically mounted on the intubation assembly rod 970. The endotracheal tube 830 has the first or distal end 830a and the second or proximal end (not shown). The endotracheal tube 830 further includes the tube body 832 having the balloon cuff 834 near the distal end 830a. A conventional Murphy eye 836 is formed between the cuff 834 and the distal end 830a.

Like the embodiments the intubation assembly rods described herein above, the intubation assembly rod 970 has an elongated substantially cylindrical body 972 having a distal end 974 (the upper end when viewing FIG. 57) and a proximal end (not shown) opposite the distal end 974. The distal end 974 of the intubation assembly rod 970 is enlarged such that the widest outside diameter 974od of the enlarged distal end 974 is equal to or slightly larger than an outside diameter of the endotracheal tube 830. If the material forming the distal end 974 of the intubation assembly rod 970 is not compressible, only a portion of its outside diameter may be equal to or slightly larger than the outside diameter of the endotracheal tube 830 so the intubation assembly rod 970 may fit through and be removed from the inside of the endotracheal tube 830.

In the embodiment illustrated in FIG. 57, the distal end 974 has a first portion 976 having a substantially barrel shape and a second portion 978 having a substantially semi-spherical shape. A positioning plug 980 extends radially outward of the intubation assembly rod 970 intermediate the body 972 and the distal end 974. As shown, the positioning plug 980 is configured to extend through the Murphy eye 836 to hold the endotracheal tube 830 in place relative to the intubation assembly rod 970 during insertion into the airway. It will be understood that all embodiments of the intubation assembly rods disclosed herein may be formed having the positioning plug 980.

Alternatively, the distal end 974 may have other desired shapes or combinations of shapes, such as football shaped, spherical, semi-spherical, or other rounded shapes. If desired, the barrel shape, football shape, spherical, semi-spherical, or other rounded shaped structure of the distal end 826 may be configured to be inflatable or compressible. Additionally, the distal end 974 of the intubation assembly rod 970 may have only one such enlarged shape.

Advantageously, the barrel shaped first portion 976, such as illustrated in FIG. 57, when formed on the intubation assembly rod 970 (or on any of the intubation assembly rods or flexible members described herein), blocks, deflects, and prevents the leading or distal end 974 of the intubation assembly rod 970 and the leading or distal end 830a of the endotracheal tube 830 from colliding into laryngeal structures such as the right arytenoid as the endotracheal tube 830 is passed forward toward the vocal cords and trachea.

If desired, the intubation assembly rod 970 may also include one or more longitudinally extending conduits, such as the conduits 906 (not shown in FIG. 57) and 908, formed therethrough for any of the purposes described above, including but not limited to one or more conduits for the video imaging device 60, the light source 62, a suction tube, or an oxygen supply tube.

It will be understood that the distal end 826 of the flexible member 822 shown in FIG. 48, may also have the shape of the distal end 974 shown in FIG. 57. Similarly, the distal end 974 of the intubation assembly rod 970 may have the shape of the distal end 826 shown in FIG. 48.

Figure 58:
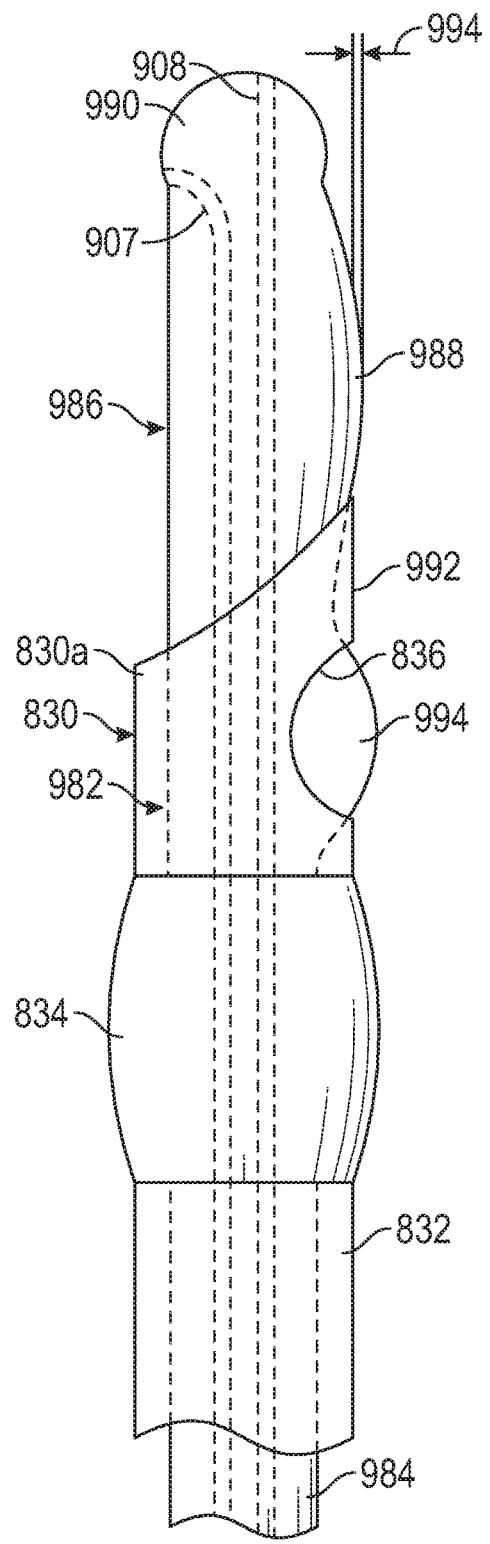
FIG. 58 is a side elevational view of a portion of a nineteenth embodiment of the intubation assembly rod.

Referring now to FIG. 58, a portion of a nineteenth embodiment of an intubation assembly rod is shown at 982. In FIG. 58, the conventional endotracheal tube 830 is shown concentrically mounted on the intubation assembly rod 970.

Like the embodiments of the intubation assembly rods described herein above, the intubation assembly rod 982 has an elongated substantially cylindrical body 984 having a distal end 986 (the upper end when viewing FIG. 58) and a proximal end (not shown) opposite the distal end 986. The distal end 986 of the intubation assembly rod 982 is also enlarged and has a first portion 988 and a second portion 990. As shown, the first portion 988 is configured as a rounded protruding portion, the widest point of which, i.e., the portion that extends the greatest distance transversely from an axis of the intubation assembly rod 982, extends transversely outward of or overhangs, an outside surface 992 of the endotracheal tube 830 (the right half of the distal end 986 when viewing FIG. 58).

The second portion 990 is also rounded and has a substantially semi-spherical shape. Advantageously, the rounded protruding first portion 988, such as illustrated in FIG. 58, when formed on the intubation assembly rod 982 (or on any of the intubation assembly rods or flexible members described herein), blocks, deflects, and prevents the leading or distal end 986 of the intubation assembly rod 982 and the leading or distal end 830a of the endotracheal tube 830 from colliding into laryngeal structures such as the right arytenoid as the endotracheal tube 830 is passed forward toward the vocal cords and trachea.

A positioning plug 994 extends radially outward of the intubation assembly rod 982 intermediate the body 984 and the distal end 986. As shown, the positioning plug 994 is configured to extend through the Murphy eye 836 to hold the endotracheal tube 830 in place relative to the intubation assembly rod 982 during insertion into the airway.

It will be understood that the distal end 826 of the flexible member 822 shown in FIG. 48, may also have a shape similar to the distal end 986 of the intubation assembly rod 982 shown in FIG. 58 and thus may include the first portion 988 and the second portion 990 having the shapes shown at 986 in FIG. 58.

If desired, the intubation assembly rod 982 may also include one or more longitudinally extending conduits, such as the conduits 906 (not shown in FIG. 58), 907, and 908, formed therethrough for any of the purposes described above, including but not limited to one or more conduits for the video imaging device 60, the light source 62, a suction tube, or an oxygen supply tube.

The principle and mode of operation of this invention have been explained and illustrated in its preferred embodiments. However, it must be understood that this invention may be practiced otherwise than as specifically explained and illustrated without departing from its spirit or scope.

What is claimed is:

1. An intubation assembly rod in combination with an endotracheal tube insertion device having an elongated insertion member, the intubation assembly rod movably attached to the endotracheal tube insertion device and configured for insertion into an endotracheal tube, such that the endotracheal tube is carried thereon, the intubation assembly rod comprising an elongated body having a distal end, a proximal end, and defining a first axis, wherein the distal end of the intubation assembly rod body is one of tapered, rounded, and spherical and defines a leading end of the intubation assembly rod, and wherein the intubation assembly rod includes a longitudinally extending channel defining a second axis parallel to the first axis and further defining a guide sleeve that extends radially outwardly from the intubation assembly rod body, the guide sleeve positioned intermediate the distal and the proximal ends of the intubation assembly rod body, the channel configured such that an elongated member of a flexible optical assembly may be inserted into the channel;

wherein the flexible optical assembly member has an elongated body having a substantially cylindrical shape and a plurality of longitudinally extending conduits formed therein, the longitudinally extending conduits configured to have one or more of a first video imaging device and first light source disposed therein.

2. The intubation assembly rod according to claim 1, wherein the longitudinally extending channel is a substantially cylindrical channel formed through the distal end of the body.

3. The intubation assembly rod according to claim 1, wherein the distal end of the intubation assembly rod body is tapered, and wherein the tapered distal end of the intubation assembly rod body defines an open end of the longitudinally extending channel.

4. The intubation assembly rod according to claim 1, wherein a distal end of the intubation assembly rod is curved.

5. The intubation assembly rod according to claim 1, wherein a distal end surface of the guide sleeve is disposed at an angle relative to an axis of the intubation assembly rod.

6. The intubation assembly rod according to claim 5, wherein a proximal end surface of the guide sleeve is disposed at the angle relative to an axis of the intubation assembly rod.

7. The intubation assembly rod according to claim 4, wherein the distal end of the intubation assembly rod is curved in two directions, each of the two directions defining axes different from an axis of the proximal end of the intubation assembly rod.

8. The intubation assembly rod according to claim 7, wherein a distal end of the channel is closed.

9. The intubation assembly rod according to claim 1, wherein a distal end of the channel is closed.

10. An intubation assembly rod configured to have an endotracheal tube carried thereon comprising:
    an elongated body having a distal end including a distal-most tip and a proximal end; and
    a longitudinally extending conduit formed within the intubation assembly rod body;
    wherein the proximal end has a substantially cylindrical shape, wherein the distal-most tip of the distal end has an enlarged portion, and wherein at least a portion of the enlarged portion of the distal-most tip is configured to extend transversely outward of an outside surface of the an endotracheal tube carried by the intubation assembly rod; and
    wherein the intubation assembly rod is configured to be removed from the endotracheal tube after the endotracheal tube is introduced into a patient.

11. The intubation assembly rod according to claim 10, further including a radially extending flange defining a stop formed at the proximal end of the body, wherein the stop is configured to retain the intubation assembly rod in a desired position within an endotracheal tube mounted on the intubation assembly rod.

12. The intubation assembly rod according to claim 11, wherein the longitudinally extending conduit is configured as one of a suction tube, as a conduit for providing oxygen to a patient, and a guidewire receiving conduit.

13. The intubation assembly rod according to claim 10, wherein the longitudinally extending conduit is a first longitudinally extending conduit, the intubation assembly rod further including a second longitudinally extending conduit, wherein each of the first and the second longitudinally extending conduits are configured as one of a suction tube, as a conduit for providing oxygen to a patient, and a guidewire receiving conduit.

14. The intubation assembly rod according to claim 10, wherein the body of the intubation assembly rod is configured to be adjustable in length so as to accommodate endotracheal tubes having a plurality of lengths.

15. An intubation assembly rod configured to have an endotracheal tube carried thereon comprising:
    an elongated body having a distal end and a proximal end; and
    a stop attached at the proximal end of the body, wherein the stop is configured to retain the intubation assembly rod in a desired position within an endotracheal tube mounted on the intubation assembly rod; and
    an oxygen source cap having:
      a body having a circumferentially extending wall defining a generally cylindrical outside surface, a first end, and an open second end defining a collar;
      an end wall formed at the first end; and
      a generally cylindrical fluid inlet extending radially outward of the wall, in fluid communication with the open second end, and configured for connection to source of oxygen;
    wherein the intubation assembly rod is mounted within the body and extending one of to and through the end wall;

wherein when the oxygen source cap is one of movably and fixedly mounted to the intubation assembly rod; and wherein the oxygen source cap is further configured to be urged into contact with an endotracheal tube connector such that oxygen from the source of oxygen may then flow through the oxygen source cap into the endotracheal tube.

16. The intubation assembly rod according to claim 15, wherein the intubation assembly rod includes an annular stop having a plurality of air flow holes formed therethrough, the annular stop one of movably and fixedly mounted to the intubation assembly rod between the second end of the body and the endotracheal tube connector.

17. The intubation assembly rod according to claim 15, further including a wall portion adjacent the collar configured as a bellows to allow the body to expand and contract longitudinally.

18. The intubation assembly rod according to claim 15, wherein the intubation assembly rod includes an annular stop positioned between the second end of the body and the endotracheal tube connector and has a plurality of air flow holes formed therethrough, and wherein the intubation assembly rod extends one of to and through the annular stop.

19. The intubation assembly rod according to claim 15, wherein the end wall includes a centrally formed aperture through which the intubation assembly rod extends.

20. The intubation assembly rod according to claim 15, wherein the intubation assembly rod has an elongated body having a proximal end and a distal end, and wherein the proximal end includes an end portion that extends at an angle from an axis thereof.

21. The intubation assembly rod according to claim 15, wherein the intubation assembly rod has a longitudinally extending conduit formed therethrough.

22. An intubation assembly rod configured to have an endotracheal tube carried thereon comprising:
an elongated body having a distal end and a proximal end; and
a stop attached at the proximal end of the body, wherein the stop is configured to retain the intubation assembly rod in a desired position within an endotracheal tube mounted on the intubation assembly rod, wherein the stop includes an aperture formed therethrough, the aperture configured as a plurality of connected aperture portions comprising a first aperture portion and a second aperture portion, wherein a diameter of the first aperture portion is larger than a diameter of the second aperture portion, wherein the stop is configured to move longitudinally along the intubation assembly rod when the intubation assembly rod is positioned in the first aperture portion, wherein the stop is configured for lateral movement of the intubation assembly rod between the first aperture portion and the second aperture portion, and wherein the stop is configured for attachment to the intubation assembly rod when the intubation assembly rod is positioned in the second aperture portion.

23. The intubation assembly rod according to claim 22, wherein the stop is movably mounted to the body.

24. The intubation assembly rod according to claim 22, wherein the body of the intubation assembly rod is configured to be adjustable in length so as to accommodate endotracheal tubes having a plurality of lengths.

25. The intubation assembly rod according to claim 15, wherein the intubation assembly rod has an elongated body having a distal end and a proximal end, wherein the proximal end has a substantially cylindrical shape, wherein the distal end has an enlarged portion, and wherein at least a portion of the enlarged portion of the distal end extends transversely outward of an outside surface of the endotracheal tube carried by the intubation assembly rod.

26. The endotracheal tube insertion device according to claim 25, wherein the intubation assembly rod further includes a positioning plug extending radially outward from the body, and wherein the positioning plug is configured to extend through a Murphy eye formed in the endotracheal tube to hold the endotracheal tube in place relative to the intubation assembly rod during insertion of the endotracheal tube into an airway.

27. An intubation assembly rod configured to have an endotracheal tube carried thereon comprising:
an elongated body having a distal end and a proximal end; and
a positioning plug extending radially outward from the elongated body, wherein the positioning plug is configured to extend through a Murphy eye formed in the endotracheal tube to hold the endotracheal tube in place relative to the intubation assembly rod during insertion of an endotracheal tube into an airway;
wherein the intubation assembly rod is configured to be removed from the endotracheal tube after the endotracheal tube is introduced into the airway.

28. The intubation assembly rod according to claim 27, wherein the proximal end of the elongated body has a substantially cylindrical shape, wherein the distal end of the elongated body has an enlarged portion, and wherein at least a portion of the enlarged portion of the distal end extends transversely outward of an outside surface of the endotracheal tube carried by the intubation assembly rod.

29. The intubation assembly rod according to claim 27, wherein the distal end of the elongated body includes an articulating joint configured for articulating movement of the distal end of the elongated body relative to a portion of the elongated body proximal to the distal end such that movement of the endotracheal tube retained thereon may be controlled.

30. An intubation assembly rod configured to have an endotracheal tube carried thereon comprising:
an elongated body having a distal end and a proximal end;
a longitudinally extending conduit formed within the intubation assembly rod body; and
a positioning plug extending radially outward from the elongated body, wherein the positioning plug is configured to extend through a Murphy eye formed in the endotracheal tube to hold the endotracheal tube in place relative to the intubation assembly rod during insertion of an endotracheal tube into an airway;
wherein the intubation assembly rod is configured to be removed from the endotracheal tube after the endotracheal tube is introduced into the airway.

31. The intubation assembly rod according to claim 30, wherein the proximal end of the elongated body has a substantially cylindrical shape, wherein the distal end of the elongated body has an enlarged portion, and wherein at least a portion of the enlarged portion of the distal end extends transversely outward of an outside surface of the endotracheal tube carried by the intubation assembly rod.

32. The intubation assembly rod according to claim 30, wherein the distal end of the elongated body includes an articulating joint configured for articulating movement of the distal end of the elongated body relative to a portion of the elongated body proximal to the distal end such that movement of the endotracheal tube retained thereon may be controlled.

* * * * *